United States Patent
Sachsenmeier et al.

(10) Patent No.: US 10,864,269 B2
(45) Date of Patent: Dec. 15, 2020

(54) THERAPEUTIC COMBINATIONS COMPRISING ANTI-CD73 ANTIBODIES AND USES THEREOF

(71) Applicant: MedImmune Limited, Cambridge (GB)

(72) Inventors: Kris Sachsenmeier, Gaithersburg, MD (US); Erin Sult, Gaithersburg, MD (US); Carl Hay, Gaithersburg, MD (US); Edmund Poon, Cambridge (GB)

(73) Assignee: MedImmune Limited, Cambridge (GB)

( * ) Notice: Subject to any disclaimer, the term of this patent is extended or adjusted under 35 U.S.C. 154(b) by 0 days.

(21) Appl. No.: 15/714,536

(22) Filed: Sep. 25, 2017

(65) Prior Publication Data
US 2018/0125973 A1 May 10, 2018

Related U.S. Application Data

(63) Continuation of application No. 14/937,565, filed on Nov. 10, 2015, now abandoned.

(60) Provisional application No. 62/078,243, filed on Nov. 11, 2014.

(51) Int. Cl.
| | |
|---|---|
| *C07K 16/40* | (2006.01) |
| *C07K 16/30* | (2006.01) |
| *A61K 39/395* | (2006.01) |
| *C07K 16/28* | (2006.01) |
| *A61K 31/519* | (2006.01) |
| *A61K 39/00* | (2006.01) |

(52) U.S. Cl.
CPC ...... *A61K 39/39558* (2013.01); *A61K 31/519* (2013.01); *C07K 16/2818* (2013.01); *C07K 16/2896* (2013.01); *C07K 16/40* (2013.01); *A61K 2039/505* (2013.01); *A61K 2039/507* (2013.01); *C07K 2317/21* (2013.01); *C07K 2317/33* (2013.01); *C07K 2317/622* (2013.01); *C07K 2317/73* (2013.01); *C07K 2317/76* (2013.01); *C07K 2317/77* (2013.01); *C07K 2317/92* (2013.01)

(58) Field of Classification Search
CPC .......... A61K 39/39558; C07K 16/2818; C07K 16/40

USPC ........................................... 424/133.1, 139.1
See application file for complete search history.

(56) References Cited

U.S. PATENT DOCUMENTS

| | | | |
|---|---|---|---|
| 2016/0108123 A1 | 4/2016 | Freeman et al. | |
| 2016/0122707 A1 | 5/2016 | Swee et al. | |
| 2016/0194407 A1 | 7/2016 | Hay et al. | |
| 2019/0161553 A1* | 5/2019 | Sather | A61K 39/395 |
| 2019/0284293 A1* | 9/2019 | Lonberg | A61K 9/0019 |

FOREIGN PATENT DOCUMENTS

WO   WO 2008147482 A2   4/2015

OTHER PUBLICATIONS

Allard, B., et al., "Targeting CD73 Enhances the Antitumor Activity of Anti-PD-1 and Anti-CTLA-4 mAbs," Clin Cancer Res., 19(20): 5626-5635 (2013).
Stagg, J., et al., "Anti-CD73 antibody therapy inhibits breast tumor growth and matastasis," PNAS 107(4): 1547-1552 (2010).
Hausler, S., et al., "Anti-CD39 and anti-CD73 antibodies A1 and 7G2 improve targeted therapy in ovarian cancer by blocking adenosine-dependent immune evasion," Am. J. Transl. Res. 6(2): 129-139 (2014).
Sitkovsky, M., et al., "Hostile, Hypoxia-A2-Adenosinergic Tumor Biology as the Next Barrier to the Tumor Immunologists," Cancer Immunol. Res. 2(7): 598-605 (2014).
International Search Report dated Mar. 15, 2016, in corresponding International Application No. PCT/EP2015/076271.
Young, et al., Sep. 12, 2016, Cancer Cell 30, 391-403.
Allard, et al., Curr Opin Pharmacol/ Aug. 2016; 29:7-16.
Clinicaltrials.gov (search results "CD73 and A2AR"; Mar. 23, 2017; p. 1).
Allard B. et al., "Targeting CD73 receptor and downstream adenosine signalling in triple-negative breast cancer", Expert Opinion on Therapeutic Targets, vol. 18 No. 8, 2014, pp. 863-881.

* cited by examiner

*Primary Examiner* — Lynn A Bristol
(74) *Attorney, Agent, or Firm* — Xiaoxiao Xue

(57) ABSTRACT

The present invention provides therapeutic combinations featuring anti-CD73 antibodies (e.g., MEDI9447) and A2A receptor inhibitors and methods of using such combinations for reducing tumor-mediated immunosuppression.

15 Claims, 16 Drawing Sheets
Specification includes a Sequence Listing.

| Kabat position: | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | a | b | c | d |
|---|---|---|---|---|---|---|---|---|---|---|---|---|---|---|---|---|---|---|---|---|---|---|---|---|---|---|---|---|---|---|---|---|---|---|---|---|---|---|---|
| IGHV3-23*01 / IGHJ2*01 | E | V | Q | L | L | E | S | G | G | G | L | V | Q | P | G | G | S | L | R | L | S | C | A | A | S | G | F | T | F | S | S | Y | A | M | S | - | - | - | - |
| MED19447 VH            | E | V | Q | L | L | E | S | G | G | G | L | V | Q | P | G | G | S | L | R | L | S | C | A | A | S | G | F | T | F | S | S | Y | A | Y | S | - | - | - | - |

CDR 1

| Kabat position: | 36 | 37 | 38 | 39 | 40 | 41 | 42 | 43 | 44 | 45 | 46 | 47 | 48 | 49 | 50 | 51 | 52 | a | b | c | d | e | f | 53 | 54 | 55 | 56 | 57 | 58 | 59 | 60 | 61 | 62 | 63 | 64 | 65 | 66 | 67 | 68 |
|---|---|---|---|---|---|---|---|---|---|---|---|---|---|---|---|---|---|---|---|---|---|---|---|---|---|---|---|---|---|---|---|---|---|---|---|---|---|---|---|
| IGHV3-23*01 / IGHJ2*01 | W | V | R | Q | A | P | G | K | G | L | E | W | V | S | A | I | S | G | - | - | - | - | - | S | G | G | S | T | Y | Y | A | D | S | V | K | G | R | F | T |
| MED19447 VH            | W | V | R | Q | A | P | G | K | G | L | E | W | V | S | A | I | S | G | - | - | - | - | - | S | G | G | R | T | Y | Y | A | D | S | V | K | G | R | F | T |

CDR 2

| Kabat position: | 69 | 70 | 71 | 72 | 73 | 74 | 75 | 76 | 77 | 78 | 79 | 80 | 81 | 82 | a | b | c | 83 | 84 | 85 | 86 | 87 | 88 | 89 | 90 | 91 | 92 | 93 | 94 | 95 | 96 | 97 | 98 | 99 | 100 | a | b | - | - |
|---|---|---|---|---|---|---|---|---|---|---|---|---|---|---|---|---|---|---|---|---|---|---|---|---|---|---|---|---|---|---|---|---|---|---|---|---|---|---|---|
| IGHV3-23*01 / IGHJ2*01 | I | S | R | D | N | S | K | N | T | L | Y | L | Q | M | N | S | L | - | - | R | A | E | D | T | A | V | Y | Y | C | A | K | - | - | Y | W | Y | F | - | - |
| MED19447 VH            | I | S | R | D | N | S | K | N | T | L | Y | L | Q | M | N | S | L | - | - | R | A | E | D | T | A | V | Y | Y | C | A | R | L | G | Y | G | R | V | - | - |

CDR 3

| Kabat position: | c | d | e | f | g | h | i | j | k | l | m | n | o | p | q | 101 | 102 | 103 | 104 | 105 | 106 | 107 | 108 | 109 | 110 | 111 | 112 | 113 |
|---|---|---|---|---|---|---|---|---|---|---|---|---|---|---|---|---|---|---|---|---|---|---|---|---|---|---|---|---|
| IGHV3-23*01 / IGHJ2*01 | - | - | - | - | - | - | - | - | - | - | - | - | - | - | - | D | L | W | G | R | G | T | L | V | T | V | S | S |
| MED19447 VH            | - | - | - | - | - | - | - | - | - | - | - | - | - | - | - | D | E | W | G | R | G | T | L | V | T | V | S | S |

Figure 1D

| Kabat position: | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | a | b | c | d | e | f | g | h | 28 | 29 | 30 | 31 | 32 | 33 | 34 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | | | | | | | | | | | | CDR 1 |
| IGLV1-44*01 / IGLJ3*01 | Q | S | V | L | T | Q | P | P | S | - | A | S | G | T | P | G | Q | R | V | T | I | S | C | S | G | S | S | S | N | , | , | , | , | , | , | I | G | S | N | T | V | N |
| MED19447 VL | Q | S | V | L | T | Q | P | P | S | - | A | S | G | T | P | G | Q | R | V | T | I | S | C | S | G | S | S | S | L | , | , | , | , | , | , | I | G | R | N | P | V | N |

| Kabat position: | 35 | 36 | 37 | 38 | 39 | 40 | 41 | 42 | 43 | 44 | 45 | 46 | 47 | 48 | 49 | 50 | 51 | a | b | c | d | e | 52 | 53 | 54 | 55 | 56 | 57 | 58 | 59 | 60 | 61 | 62 | 63 | 64 | 65 | 66 | 67 | 68 | 69 |
|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | CDR 2 | | | | | | | | | | | | | | | | | |
| IGLV1-44*01 / IGLJ3*01 | W | Y | Q | Q | L | P | G | T | A | P | K | L | L | I | Y | S | N | , | , | , | , | , | N | Q | R | P | S | G | V | P | D | R | F | S | G | S | K | S | G | T |
| MED19447 VL | W | Y | Q | Q | L | P | G | T | A | P | K | L | L | I | Y | L | D | , | , | , | , | , | N | L | R | L | S | G | V | P | D | R | F | S | G | S | K | S | G | T |

| Kabat position: | 70 | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | a | b | c | d | e | f | g | h | i | 96 | 97 | 98 | 99 | 100 | 101 | 102 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | CDR 3 | | | | | | | | | | | | | | | | | |
| IGLV1-44*01 / IGLJ3*01 | S | A | S | L | A | I | S | G | L | Q | S | E | D | E | A | D | Y | Y | C | A | A | W | D | D | S | L | , | , | , | , | , | , | , | , | , | V | V | F | G | G | G | T |
| MED19447 VL | S | A | S | L | A | I | S | G | L | Q | S | E | D | E | A | D | Y | Y | C | A | T | W | D | D | S | H | P | G | , | , | , | , | , | , | , | W | T | F | G | G | G | T |

| Kabat position: | 103 | 104 | 105 | 106 | a | b | c | 107 |
|---|---|---|---|---|---|---|---|---|
| IGLV1-44*01 / IGLJ3*01 | K | L | T | V | - | - | - | L |
| MED19447 VL | K | L | T | V | - | - | - | L |

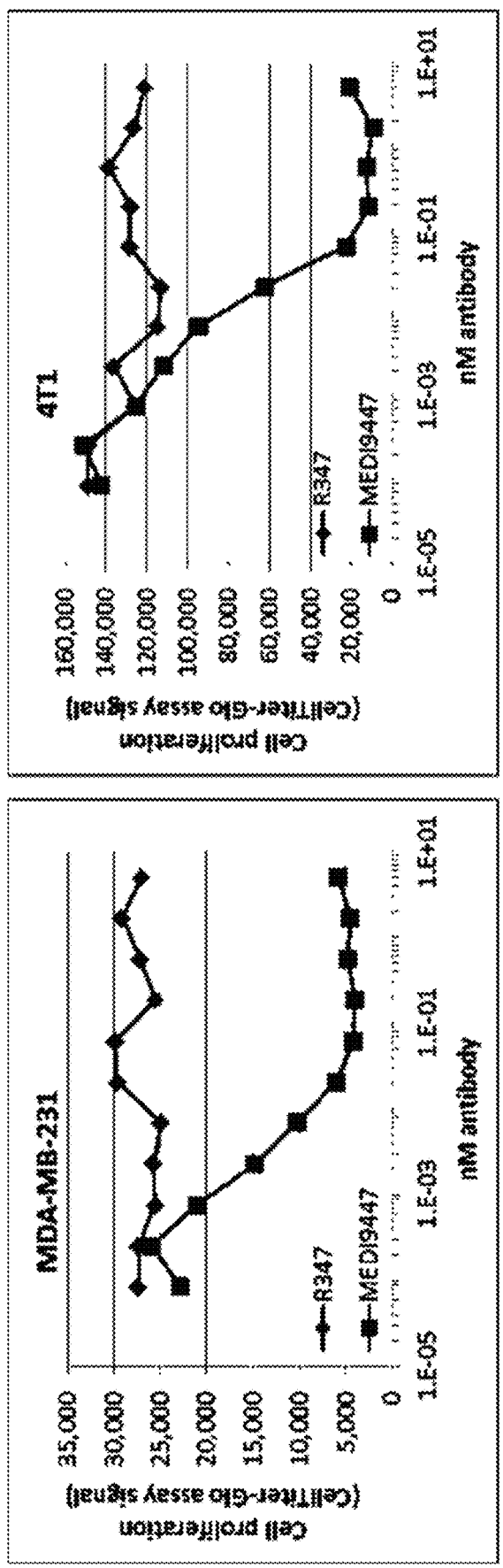
Figure 2: Antibody-mediated Internalization of Cytotoxic FabZAP Reagent into MDA-MB-231 Cells and 4T1 Cells

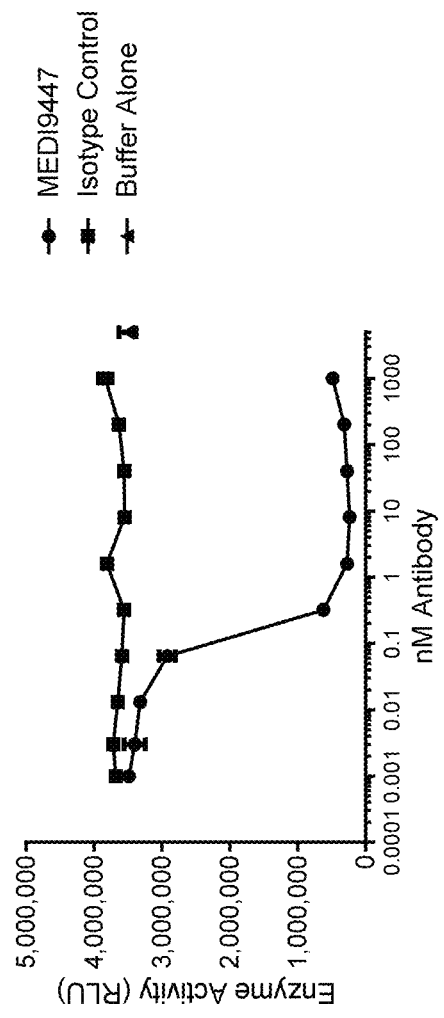
Figure 3A: Inhibition of 5' ectonucleotidase by an Anti-CD73 Antibody

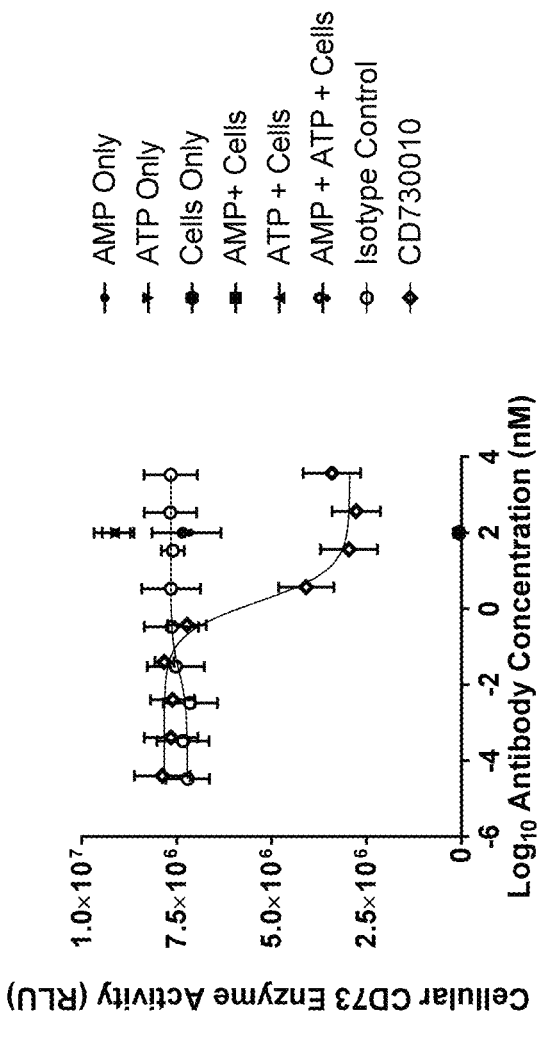

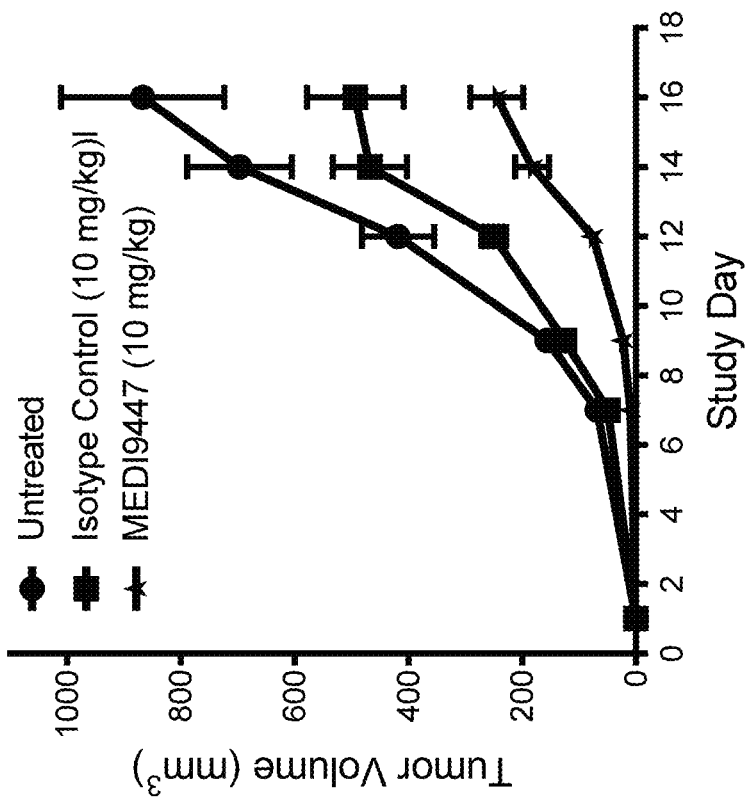
Figure 4: MEDI9447 Inhibited Tumor Growth

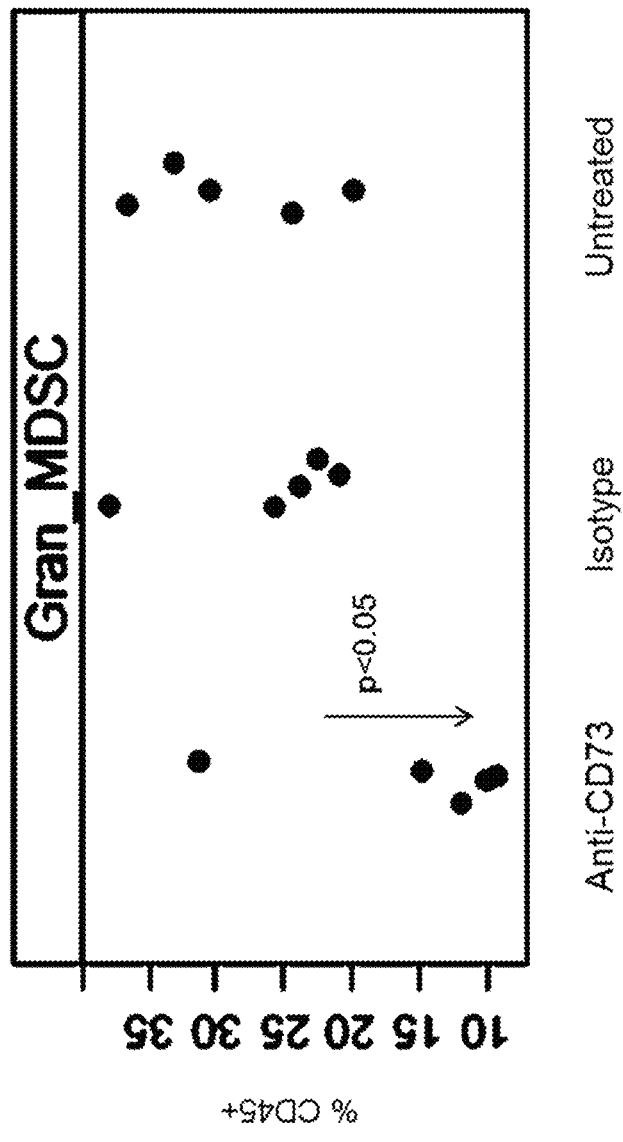

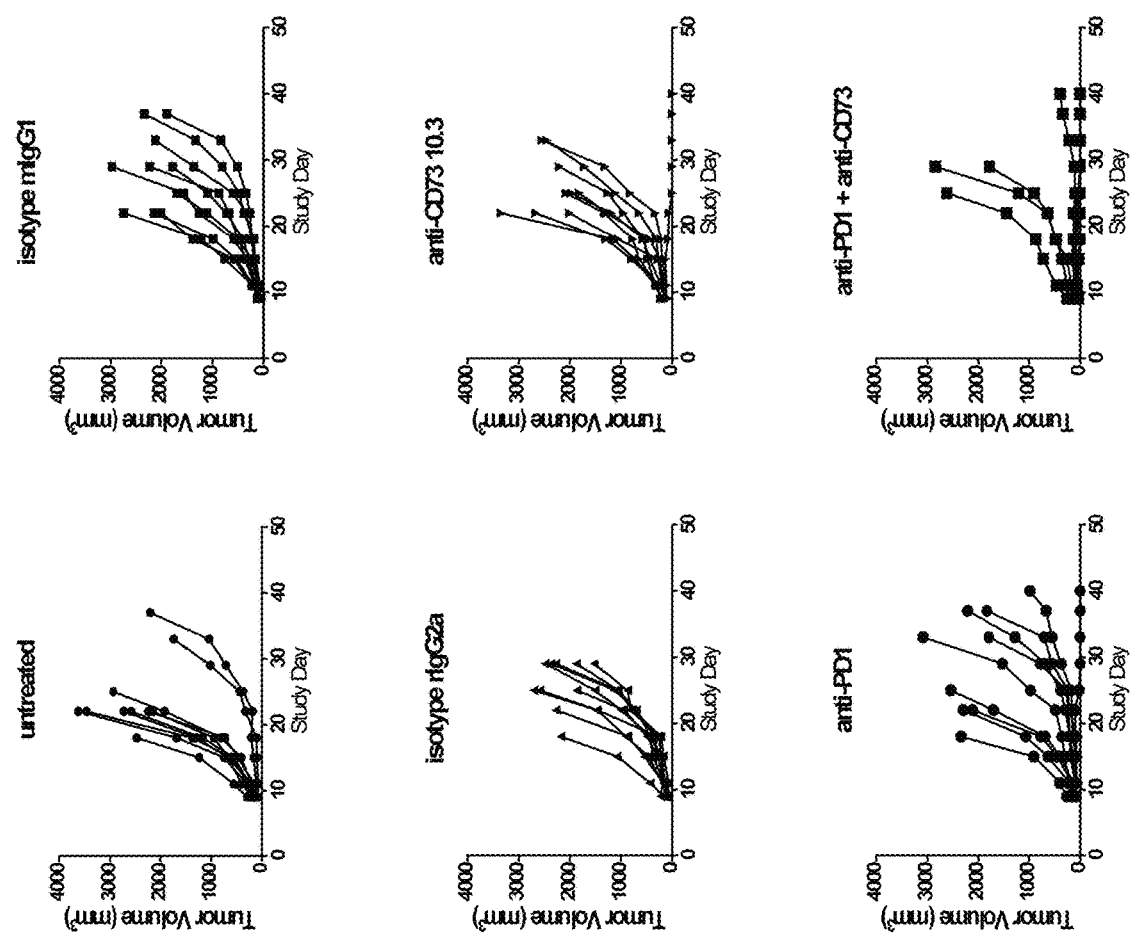
Figure 6: MEDI9447 mIgG1 combination with anti-PD1 *in vivo* tumor volume spider plots

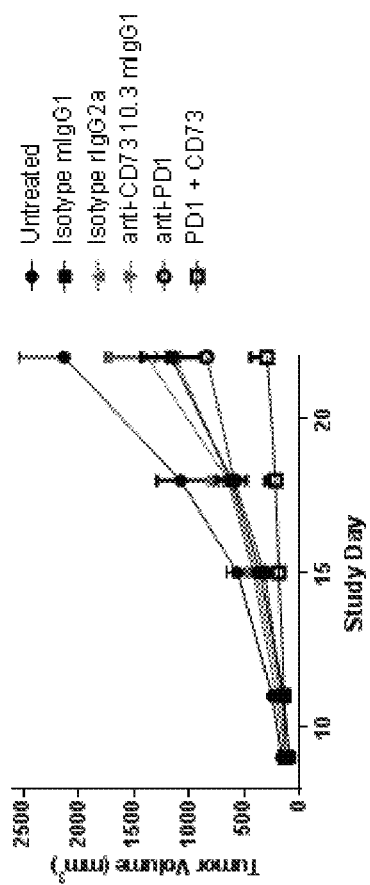
Figure 7: MEDI9447 mIgG1 combination with anti-PD1 inhibits *in vivo* mean tumor volume.

Figure 9: Effect of Phen0203 hIgG1 Antibody on AMP-mediated Suppression of $CD4^+CD25^-$ T-cell Proliferation

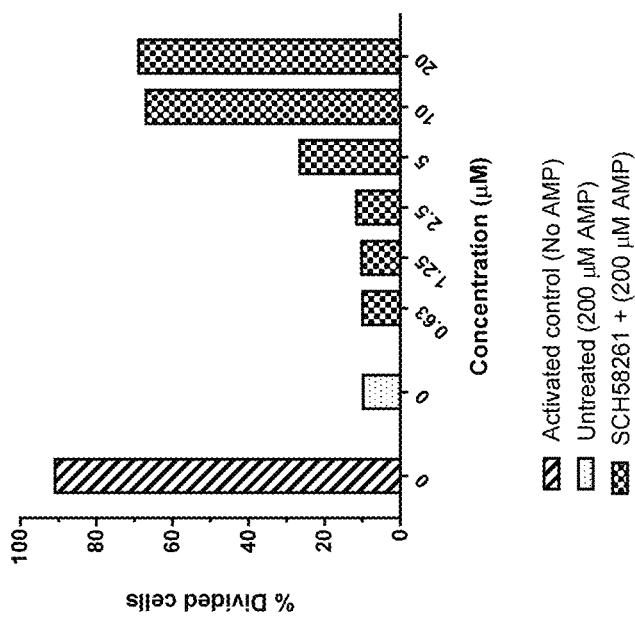
Figure 10: Effect of SCH58261 on AMP-mediated suppression of CD4⁺CD25⁻ T cell proliferation

```
SEQUENCE LISTING

<160> NUMBER OF SEQ ID NOS: 148

<210> SEQ ID NO 1
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Ser Val Leu Thr Gln Pro Pro Ser Val Ser Val Ser Pro Gly Gln
1               5                   10                  15

Thr Ala Thr Ile Thr Cys Ser Gly Asp Lys Val Gly Asp Lys Tyr Ala
                20                  25                  30

Ser Trp Tyr Gln Gln Lys Pro Gly Gln Ser Pro Val Leu Val Ile Tyr
            35                  40                  45
```

```
Glu Asp Thr Lys Arg Pro Ser Arg Ile Pro Glu Arg Phe Ser Gly Ser
 50                  55                  60

Asn Ser Gly Asn Thr Ala Thr Leu Thr Ile Ser Gly Thr Gln Ala Leu
 65                  70                  75                  80

Asp Glu Ala Asp Tyr Phe Cys Gln Ala Trp Asp Thr Ser Phe Trp Val
                 85                  90                  95

Phe Gly Gly Gly Thr Lys Leu Thr Val Leu
            100                 105

<210> SEQ ID NO 2
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Lys Gly Tyr Tyr Tyr Met Asp Val Trp Gly Gln Gly
            100                 105                 110

Thr Met Val Thr Val Ser Ser
        115

<210> SEQ ID NO 3
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Leu Pro Val Leu Thr Gln Pro Pro Ser Val Ser Gly Thr Pro Gly Gln
 1               5                  10                  15

Arg Val Thr Ile Ser Cys Ser Gly Ser Leu Ser Asn Ile Gly Arg Asn
             20                  25                  30

Pro Val Asn Trp Tyr Lys Gln Val Pro Gly Thr Ala Pro Lys Leu Leu
         35                  40                  45

Ile Tyr Leu Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Thr Trp Asp Asp Ser Leu
                 85                  90                  95

Asn Gly Trp Leu Phe Gly Gly Gly Thr Lys Leu Thr Val Leu
            100                 105                 110
```

```
<210> SEQ ID NO 4
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Ser Thr Ile Asp Tyr Trp Gly Arg Gly Thr Leu
            100                 105                 110

Val Thr Val Ser Ser
        115

<210> SEQ ID NO 5
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Lys
            20                  25                  30

Tyr Val Gln Trp Tyr Gln Gln Arg Pro Gly Ser Ser Pro Met Ala Val
        35                  40                  45

Ile Tyr Lys Asp Asn Gln Arg Ser Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Pro Glu Asp Glu Ala Asp Tyr Tyr Cys Gln Ser Tyr Asp Ala
                85                  90                  95

Ser Asn Tyr Tyr Val Phe Gly Thr Gly Thr Lys Val Thr Val Leu
            100                 105                 110

<210> SEQ ID NO 6
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Val Gln Leu Leu Glu Ser Gly Gly Gly Leu Val Gln Pro Gly Gly
```

```
                1               5                   10                  15
Ser Leu Arg Leu Ser Cys Ala Ala Ser Gly Phe Thr Phe Ser Ser Tyr
                    20                  25                  30

Ala Met Ser Trp Val Arg Gln Ala Pro Gly Lys Gly Leu Glu Trp Val
                    35                  40                  45

Ser Ala Ile Ser Gly Ser Gly Gly Ser Thr Tyr Tyr Ala Asp Ser Val
                50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Arg Arg Gly His Gly Leu Tyr Phe Asp Leu Trp Gly Gln Gly Thr
                    100                 105                 110

Thr Val Thr Val Ser Ser
                115
```

<210> SEQ ID NO 7
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Gln Ser Val Leu Thr Gln Pro Pro Ser Ala Ser Gly Thr Pro Gly Gln
1               5                   10                  15

Arg Val Thr Ile Ser Cys Ser Gly Ser Arg Pro Asn Ile Gly Gly Asn
                    20                  25                  30

Thr Val Asn Trp Tyr Gln Gln Leu Pro Gly Ala Ala Pro Lys Leu Leu
                    35                  40                  45

Ile Tyr Ser Asn Ser Gln Arg Pro Ser Gly Val Pro Asp Arg Phe Ser
                50                  55                  60

Gly Ser Lys Tyr Gly Thr Ser Ala Ser Leu Ala Ile Ser Gly Leu Gln
65                  70                  75                  80

Ser Asp Asp Glu Ala Asp Tyr Tyr Cys Gly Thr Trp Asp Asp Ser Leu
                    85                  90                  95

Asn Gly Pro Val Phe Gly Arg Gly Thr Lys Leu Thr Val Leu
                    100                 105                 110
```

<210> SEQ ID NO 8
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Gln Val Gln Leu Gln Glu Ser Gly Pro Gly Leu Val Arg Pro Ser Glu
1               5                   10                  15

Thr Leu Ser Leu Thr Cys Thr Val Ser Gly Gly Ser Ile Ser Ser Ser
                    20                  25                  30

Ser Tyr Tyr Trp Ala Trp Val Arg Gln Ser Pro Gly Lys Gly Leu Glu
                    35                  40                  45

Trp Ile Gly Asn Ile Tyr Tyr Arg Gly Ser Thr Tyr Tyr Asn Pro Ser
                50                  55                  60

Leu Lys Ser Arg Val Thr Met Ser Val Asp Met Ser Lys His Gln Phe
```

```
                    65                  70                  75                  80
Ser Leu Lys Leu Ser Ser Leu Asn Ala Ala Asp Thr Ala Val Tyr Tyr
                85                  90                  95

Cys Ala Ser Leu Tyr Ser Gly Thr Tyr Val Phe Asp Tyr Trp Gly Arg
                100                 105                 110

Gly Thr Leu Val Thr Val Ser Ser
            115                 120
```

<210> SEQ ID NO 9
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Gln Ser Val Leu Thr Gln Pro Ala Ser Val Ser Gly Ser Pro Gly Gln
1               5                   10                  15

Ser Ile Thr Ile Ser Cys Ala Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Glu Gly Ser Lys Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Thr Arg
                85                  90                  95

Ser Thr Arg Val Phe Gly Gly Gly Thr Lys Leu Thr Val Leu
                100                 105                 110
```

<210> SEQ ID NO 10
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Gly Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Ile Lys Tyr Tyr Ala Asp Ser Val
        50                  55                  60

Lys Gly Arg Phe Thr Ile Ser Arg Asp Asp Ser Lys Asn Ala Leu Tyr
65                  70                  75                  80

Leu Gln Met Asn Ser Leu Arg Ala Glu Asp Thr Ala Val Tyr Tyr Cys
                85                  90                  95

Ser Thr Leu Ser Gly Ser Tyr Gly Tyr Phe Asp Tyr Trp Gly Arg Gly
                100                 105                 110

Thr Leu Val Thr Val Ser Ser
            115
```

```
<210> SEQ ID NO 11
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Ser Trp Tyr Gln His Leu Pro Gly Thr Ala Pro Gln Leu Leu
        35                  40                  45

Ile Tyr Thr Asn Asn His Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Ser Gly Tyr Val Phe Gly Thr Gly Thr Lys Val Thr Val Leu
            100                 105                 110

<210> SEQ ID NO 12
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Ile Lys Tyr Tyr Ala Asp Ser Val
    50                  55                  60

Lys Gly Arg Phe Thr Ile Ser Arg Asp Asn Ser Lys Asn Ser Leu Phe
65                  70                  75                  80

Leu Gln Met Asn Ser Leu Arg Asp Asp Thr Ala Thr Tyr Tyr Cys
                85                  90                  95

Ala Arg Gly His Leu Leu Arg Ile Gly Asp Ile Phe Tyr Tyr Ser Leu
            100                 105                 110

Asp Val Trp Gly Gln Gly Thr Leu Val Thr Val Ser Ser
        115                 120                 125

<210> SEQ ID NO 13
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Ser Val Leu Thr Gln Pro Pro Ser Ala Ser Gly Ala Pro Gly Gln
1               5                   10                  15
```

```
Arg Val Thr Ile Ser Cys Ser Gly Ser Ser Asn Ile Gly Ser Asn
            20                  25                  30

Thr Val Asn Trp Tyr Gln Arg Leu Pro Gly Ala Ala Pro Gln Leu Leu
         35                  40                  45

Ile Tyr Asn Asn Asp Gln Arg Pro Ser Gly Ile Pro Asp Arg Phe Ser
 50                  55                  60

Gly Ser Lys Ser Gly Thr Ser Gly Ser Leu Val Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Ser Gly Asn Val Phe Gly Thr Gly Thr Lys Val Thr Val Leu
            100                 105                 110

<210> SEQ ID NO 14
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
         35                  40                  45

Ala Val Ile Ser Tyr Asp Gly Ser Ile Lys Tyr Tyr Ala Asp Ser Val
 50                  55                  60

Lys Gly Arg Phe Ala Ile Ser Arg Asp Asn Ala Lys Asn Thr Leu Tyr
 65                  70                  75                  80

Leu Gln Met Asn Ser Leu Arg Arg Glu Asp Thr Ala Met Tyr Tyr Cys
                 85                  90                  95

Ala Ser Gly Leu Thr Gly Val Ala Gly Ala Leu Gly Val Trp Gly Arg
            100                 105                 110

Gly Thr Leu Val Thr Val Ser Ser
         115                 120

<210> SEQ ID NO 15
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Ser Val Leu Thr Gln Pro Pro Ser Val Ser Val Ser Pro Gly Gln
1               5                   10                  15

Thr Ala Thr Ile Thr Cys Ser Gly Asp Arg Leu Arg Asn Glu Phe Val
            20                  25                  30

Ser Trp Tyr Gln Gln Arg Pro Gly Gln Ser Pro Val Val Val Ile Tyr
         35                  40                  45

Gln Asp Ile Tyr Arg Pro Ser Gly Ile Pro Asp Arg Phe Ser Gly Ser
 50                  55                  60

Lys Ser Gly Asn Thr Ala Thr Leu Thr Ile Ser Gly Pro Gln Thr Val
 65                  70                  75                  80
```

Asp Glu Ala Asp Tyr Tyr Cys Gln Ala Trp Asp Ser Asn Thr Val Val
                85                  90                  95

Phe Gly Gly Gly Thr Lys Leu Thr Val Leu
            100                 105

<210> SEQ ID NO 16
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Leu Gln Leu Gln Glu Ser Gly Ser Gly Leu Val Lys Pro Ser Gln
1               5                   10                  15

Thr Leu Ser Leu Ile Cys Ala Val Ser Gly Ser Ile Thr Ser Gly
            20                  25                  30

Gly Asn Ala Trp Asn Trp Ile Arg Gln Ser Pro Gly Ala Gly Leu Glu
        35                  40                  45

Trp Ile Gly Tyr Ile Phe Ser Asn Gly Ala Thr Tyr Tyr Asn Pro Ser
    50                  55                  60

Leu Glu Ser Arg Val Thr Ile Ser Ala Asp Thr Ser Lys Asn Gln Phe
65                  70                  75                  80

Ser Leu Thr Leu Thr Ser Val Thr Ala Ala Asp Thr Ala Val Tyr Tyr
                85                  90                  95

Cys Ala Arg Gly Asp Phe Trp Thr Gly Lys Gly Val Phe Asp Pro Trp
            100                 105                 110

Gly Gln Gly Thr Leu Val Thr Val Ser Ser
        115                 120

<210> SEQ ID NO 17
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Tyr Ser Trp Val Arg Gln Ala Pro Gly Lys Gly Leu Glu Trp Val
        35                  40                  45

Ser Ala Ile Ser Gly Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Gly Arg Val Asp Glu Trp Gly Arg Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
210                 215                 220

Thr Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 18
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
gaggtgcagc tgttggagtc tgggggaggc ttggtacagc ctgggggtc cctgagactc      60 tcctgtgcag cctctggatt caccttagc agctatgcct atagctgggt ccgccaggct    120
ccagggaagg ggctggagtg ggtctcagct attagtggta gtggtggtag aacatactac    180
gcagactccg tgaagggccg gttcaccatc tccagagaca attccaagaa cacgctgtat    240
ctgcaaatga acagcctgag agccgaggac acggccgtgt attactgtgc gagattaggg    300

```
tatgggcggg tggacgagtg gggcagggga accctggtca ccgtctcgag tgcgtcgacc    360
aagggcccat ccgtcttccc cctggcaccc tcctccaaga gcacctctgg ggcacagcg     420
gccctgggct gcctggtcaa ggactacttc cccgaaccgg tgacggtgtc ctggaactca    480
ggcgctctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga gagttgagcc caaatcttgt    660
gacaaaactc acacatgccc accgtgccca gcacctgaat tcgagggggg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc tccatcgaga aaaccatctc caaagccaaa   1020
gggcagcccc gagaaccaca ggtctacacc ctgcccccat cccgggagga gatgaccaag   1080
aaccaggtca gcctgacctg cctggtcaaa ggcttctatc ccagcgacat cgccgtggag   1140
tgggagagca atgggcagcc ggagaacaac tacaagacca cgcctcccgt gctggactcc   1200
gacggctcct tcttcctcta tagcaagctc accgtggaca agagcaggtg gcagcagggg   1260
aacgtcttct catgctccgt gatgcatgag gctctgcaca accactacac gcagaagagc   1320
ctctccctgt ctccgggtaa a                                              1341
```

<210> SEQ ID NO 19
<211> LENGTH: 216
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 19

Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Arg Asn
            20                  25                  30

Pro Val Asn Trp Tyr Gln Gln Leu Pro Gly Thr Ala Pro Lys Leu Leu
        35                  40                  45

Ile Tyr Leu Asp Asn Leu Arg Leu Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser His
                85                  90                  95

Pro Gly Trp Thr Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 20
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
cagtctgtgc tgactcagcc accctcagcg tctgggaccc ccgggcagag ggtcaccatc      60
tcttgttctg gaagcctctc caacatcgga aggaatcctg ttaactggta tcagcagctc     120
ccagggacgg cccccaaact cctcatctat cttgataatc tacggctaag tggggtccct     180
gaccgattct ctggctccaa gtctggaacc tcagcctccc tggccatcag tgggctccag     240
tctgaggatg aggctgatta ttactgtgca acatgggatg acagccaccc cggggtggacg     300 ttcggcggag ggaccaagct gaccgtccta ggtcagccca aggcggcgcc ctcggtcact     360
ctgttcccgc cctcctctga ggagcttcaa gccaacaagg ccacactggt gtgtctcata     420
agtgacttct acccgggagc cgtgacagtg gcctggaagg cagatagcag ccccgtcaag     480
gcgggagtgg agaccaccac accctccaaa caaagcaaca caagtacgc ggccagcagc     540 tacctgagcc tgacgcctga gcagtggaag tcccacagaa gctacagctg ccaggtcacg     600
catgaaggga gcaccgtgga agacagtg gcccctacag aatgttca                     648

<210> SEQ ID NO 21
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Tyr Ser Trp Val Arg Gln Ala Pro Gly Lys Gly Leu Glu Trp Val
        35                  40                  45

Ser Ala Ile Ser Gly Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Gly Arg Val Asp Glu Trp Gly Arg Gly Thr Leu
            100                 105                 110

Val Thr Val Ser Ser
        115

```
<210> SEQ ID NO 22
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(351)

<400> SEQUENCE: 22 gag gtg cag ctg ttg gag tct ggg gga ggc ttg gta cag cct ggg ggg      48
Glu Val Gln Leu Leu Glu Ser Gly Gly Gly Leu Val Gln Pro Gly Gly
1               5                   10                  15 tcc ctg aga ctc tcc tgt gca gcc tct gga ttc acc ttt agc agc tat      96
Ser Leu Arg Leu Ser Cys Ala Ala Ser Gly Phe Thr Phe Ser Ser Tyr
            20                  25                  30 gcc tat agc tgg gtc cgc cag gct cca ggg aag ggg ctg gag tgg gtc     144
Ala Tyr Ser Trp Val Arg Gln Ala Pro Gly Lys Gly Leu Glu Trp Val
        35                  40                  45 tca gct att agt ggt agt ggt ggt aga aca tac tac gca gac tcc gtg     192
Ser Ala Ile Ser Gly Ser Gly Gly Arg Thr Tyr Tyr Ala Asp Ser Val
    50                  55                  60 aag ggc cgg ttc acc atc tcc aga gac aat tcc aag aac acg ctg tat     240
Lys Gly Arg Phe Thr Ile Ser Arg Asp Asn Ser Lys Asn Thr Leu Tyr
65                  70                  75                  80 ctg caa atg aac agc ctg aga gcc gag gac acg gcc gtg tat tac tgt     288
Leu Gln Met Asn Ser Leu Arg Ala Glu Asp Thr Ala Val Tyr Tyr Cys
                85                  90                  95 gcg aga tta ggg tat ggg cgg gtg gac gag tgg ggc agg gga acc ctg     336
Ala Arg Leu Gly Tyr Gly Arg Val Asp Glu Trp Gly Arg Gly Thr Leu
            100                 105                 110 gtc acc gtc tcg agt                                                 351
Val Thr Val Ser Ser
            115

<210> SEQ ID NO 23
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Arg Asn
            20                  25                  30

Pro Val Asn Trp Tyr Gln Gln Leu Pro Gly Thr Ala Pro Lys Leu Leu
        35                  40                  45

Ile Tyr Leu Asp Asn Leu Arg Leu Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser His
                85                  90                  95

Pro Gly Trp Thr Phe Gly Gly Gly Thr Lys Leu Thr Val Leu
            100                 105                 110

<210> SEQ ID NO 24
```

```
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(330)

<400> SEQUENCE: 24 cag tct gtg ctg act cag cca ccc tca gcg tct ggg acc ccc ggg cag       48
Gln Ser Val Leu Thr Gln Pro Pro Ser Ala Ser Gly Thr Pro Gly Gln
1               5                  10                  15 agg gtc acc atc tct tgt tct gga agc ctc tcc aac atc gga agg aat       96
Arg Val Thr Ile Ser Cys Ser Gly Ser Leu Ser Asn Ile Gly Arg Asn
            20                  25                  30 cct gtt aac tgg tat cag cag ctc cca ggg acg gcc ccc aaa ctc ctc      144
Pro Val Asn Trp Tyr Gln Gln Leu Pro Gly Thr Ala Pro Lys Leu Leu
        35                  40                  45 atc tat ctt gat aat cta cgg cta agt ggg gtc cct gac cga ttc tct      192
Ile Tyr Leu Asp Asn Leu Arg Leu Ser Gly Val Pro Asp Arg Phe Ser
    50                  55                  60 ggc tcc aag tct gga acc tca gcc tcc ctg gcc atc agt ggg ctc cag      240
Gly Ser Lys Ser Gly Thr Ser Ala Ser Leu Ala Ile Ser Gly Leu Gln
65                  70                  75                  80 tct gag gat gag gct gat tat tac tgt gca aca tgg gat gac agc cac      288
Ser Glu Asp Glu Ala Asp Tyr Tyr Cys Ala Thr Trp Asp Asp Ser His
                85                  90                  95 ccc ggg tgg acg ttc ggc gga ggg acc aag ctg acc gtc cta              330
Pro Gly Trp Thr Phe Gly Gly Gly Thr Lys Leu Thr Val Leu
            100                 105                 110

<210> SEQ ID NO 25
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Leu Pro Val Leu Thr Gln Pro Pro Ser Val Ser Gly Thr Pro Gly Gln
1               5                  10                  15

Arg Val Thr Ile Ser Cys
            20

<210> SEQ ID NO 26
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Ser Val Leu Thr Gln Pro Pro Ser Ala Ser Gly Thr Pro Gly Gln
1               5                  10                  15

Arg Val Thr Ile Ser Cys
            20

<210> SEQ ID NO 27
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 27

Trp Tyr Lys Gln Val Pro Gly Thr Ala Pro Lys Leu Leu Ile Tyr
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Trp Tyr Gln Gln Leu Pro Gly Thr Ala Pro Lys Leu Leu Ile Tyr
1               5                   10                  15

<210> SEQ ID NO 29
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gly Val Pro Asp Arg Phe Ser Gly Ser Lys Ser Gly Thr Ser Ala Ser
1               5                   10                  15

Leu Ala Ile Ser Gly Leu Gln Ser Glu Asp Glu Ala Asp Tyr Tyr Cys
                20                  25                  30

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Phe Gly Gly Gly Thr Lys Leu Thr Val Leu
1               5                   10

<210> SEQ ID NO 31
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
                20                  25                  30

<210> SEQ ID NO 32
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 32

Trp Val Arg Gln Ala Pro Gly Lys Gly Leu Glu Trp Val Ser
1               5                   10

<210> SEQ ID NO 33
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Trp Gly Arg Gly Thr Leu Val Thr Val Ser Ser
1               5                   10

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ser Tyr Ala Met Ser
1               5

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ser Tyr Ala Tyr Ser
1               5

<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ala Ile Ser Gly Ser Gly Gly Ser Thr Tyr Tyr Ala Asp Ser Val Lys
1               5                   10                  15
```

Gly

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Leu Ile Trp Gly Ser Trp Gly Ser Thr Tyr Tyr Ala Asp Ser Val Lys
1               5                   10                  15

Gly

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Ile Ser Gly Ser Gly Gly Arg Thr Tyr Tyr Ala Asp Ser Val Lys
1               5                   10                  15

Gly

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Ile Ser Gly Ser Trp Gly Arg Thr Tyr Tyr Ala Asp Ser Val Lys
1               5                   10                  15

Gly

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Leu Gly Tyr Ser Thr Ile Asp Tyr
1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Leu Gly Tyr Ser Thr Ile Asp Lys
1               5

```
<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Leu Gly Tyr Ser Thr Ile Asp Met
1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Leu Gly Tyr Ser Thr Ile Asp Leu
1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Leu Gly Tyr Gly Arg Val Asp Glu
1               5

<210> SEQ ID NO 46
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ser Gly Ser Leu Ser Asn Ile Gly Arg Asn Pro Val Asn
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ser Gly Ser Leu Ser Asn Ile Gly Arg Asn Glu Val Asn
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48
```

```
Ser Gly Ser Leu Ser Asn Ile Gly Arg Asn Asp Val Asn
1               5                   10
```

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

```
Leu Asn Asn Gln Arg Pro Ser
1               5
```

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

```
Leu Asp Asn Leu Arg Leu Gly
1               5
```

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

```
Leu Asp Asn Leu Arg Leu Ser
1               5
```

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

```
Leu Asn Asn Gln Arg Leu Gly
1               5
```

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

```
Ala Thr Trp Asp Asp Ser Leu Asn Gly Trp Leu
1               5                   10
```

<210> SEQ ID NO 54
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 54

Ala Thr Trp Asp Asp Ser Leu Lys Gly Trp Leu
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ala Thr Trp Asp Asp Ser Leu Ile Gly Trp Leu
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ala Thr Trp Asp Asp Ser His Pro Gly Trp Thr
1               5                   10

<210> SEQ ID NO 57
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Leu Pro Val Leu Thr Gln Pro Pro Ser Val Ser Gly Thr Pro Gly Gln
1               5                   10                  15

Arg Val Thr Ile Ser Cys Ser Gly Ser Leu Ser Asn Ile Gly Arg Asn
            20                  25                  30

Pro Val Asn Trp Tyr Lys Gln Val Pro Gly Thr Ala Pro Lys Leu Leu
        35                  40                  45

Ile Tyr Leu Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Asn Gly Trp Leu Phe Gly Gly Gly Thr Lys Leu Thr Val Leu
            100                 105                 110

<210> SEQ ID NO 58
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58
```

Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Arg Asn
            20                  25                  30

Pro Val Asn Trp Tyr Gln Gln Leu Pro Gly Thr Ala Pro Lys Leu Leu
        35                  40                  45

Ile Tyr Leu Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Asn Gly Trp Leu Phe Gly Gly Gly Thr Lys Leu Thr Val Leu
            100                 105                 110

<210> SEQ ID NO 59
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Arg Asn
            20                  25                  30

Glu Val Asn Trp Tyr Gln Gln Leu Pro Gly Thr Ala Pro Lys Leu Leu
        35                  40                  45

Ile Tyr Leu Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Asn Gly Trp Leu Phe Gly Gly Gly Thr Lys Leu Thr Val Leu
            100                 105                 110

<210> SEQ ID NO 60
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Arg Asn
            20                  25                  30

Glu Val Asn Trp Tyr Gln Gln Leu Pro Gly Thr Ala Pro Lys Leu Leu
        35                  40                  45

Ile Tyr Leu Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

```
Ser Glu Asp Glu Ala Asp Tyr Tyr Cys Ala Thr Trp Asp Asp Ser Leu
                85                  90                  95

Lys Gly Trp Leu Phe Gly Gly Gly Thr Lys Leu Thr Val Leu
            100                 105                 110

<210> SEQ ID NO 61
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Arg Asn
            20                  25                  30

Pro Val Asn Trp Tyr Gln Gln Leu Pro Gly Thr Ala Pro Lys Leu Leu
        35                  40                  45

Ile Tyr Leu Asp Asn Leu Arg Leu Gly Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Lys Gly Trp Leu Phe Gly Gly Gly Thr Lys Leu Thr Val Leu
            100                 105                 110

<210> SEQ ID NO 62
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Arg Asn
            20                  25                  30

Pro Val Asn Trp Tyr Gln Gln Leu Pro Gly Thr Ala Pro Lys Leu Leu
        35                  40                  45

Ile Tyr Leu Asp Asn Leu Arg Leu Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Ile Gly Trp Leu Phe Gly Gly Gly Thr Lys Leu Thr Val Leu
            100                 105                 110

<210> SEQ ID NO 63
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 63

Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Arg Asn
            20                  25                  30

Asp Val Asn Trp Tyr Gln Gln Leu Pro Gly Thr Ala Pro Lys Leu Leu
        35                  40                  45

Ile Tyr Leu Asn Asn Gln Arg Leu Gly Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Lys Gly Trp Leu Phe Gly Gly Gly Thr Lys Leu Thr Val Leu
            100                 105                 110

<210> SEQ ID NO 64
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Arg Asn
            20                  25                  30

Pro Val Asn Trp Tyr Gln Gln Leu Pro Gly Thr Ala Pro Lys Leu Leu
        35                  40                  45

Ile Tyr Leu Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser His
                85                  90                  95

Pro Gly Trp Thr Phe Gly Gly Gly Thr Lys Leu Thr Val Leu
            100                 105                 110

<210> SEQ ID NO 65
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Arg Asn
            20                  25                  30

Pro Val Asn Trp Tyr Gln Gln Leu Pro Gly Thr Ala Pro Lys Leu Leu
        35                  40                  45

Ile Tyr Leu Asn Asn Gln Arg Pro Ser Gly Val Pro Asp Arg Phe Ser
50                  55                  60

```
Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Thr Trp Asp Asp Ser Leu
                 85                  90                  95

Asn Gly Trp Leu Phe Gly Gly Gly Thr Lys Leu Thr Val Leu
            100                 105                 110

<210> SEQ ID NO 66
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Ser Val Leu Thr Gln Pro Pro Ser Ala Ser Gly Thr Pro Gly Gln
  1               5                  10                  15

Arg Val Thr Ile Ser Cys Ser Gly Ser Leu Ser Asn Ile Gly Arg Asn
                 20                  25                  30

Glu Val Asn Trp Tyr Gln Gln Leu Pro Gly Thr Ala Pro Lys Leu Leu
            35                  40                  45

Ile Tyr Leu Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Thr Trp Asp Asp Ser His
                 85                  90                  95

Pro Gly Trp Thr Phe Gly Gly Gly Thr Lys Leu Thr Val Leu
            100                 105                 110

<210> SEQ ID NO 67
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Ser Val Leu Thr Gln Pro Pro Ser Ala Ser Gly Thr Pro Gly Gln
  1               5                  10                  15

Arg Val Thr Ile Ser Cys Ser Gly Ser Leu Ser Asn Ile Gly Arg Asn
                 20                  25                  30

Pro Val Asn Trp Tyr Gln Gln Leu Pro Gly Thr Ala Pro Lys Leu Leu
            35                  40                  45

Ile Tyr Leu Asp Asn Leu Arg Leu Gly Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Thr Trp Asp Asp Ser His
                 85                  90                  95

Pro Gly Trp Thr Phe Gly Gly Gly Thr Lys Leu Thr Val Leu
            100                 105                 110

<210> SEQ ID NO 68
<211> LENGTH: 110
<212> TYPE: PRT
<213> ORGANISM: Artificial Sequence
<220> FEATURE:
```

<223> OTHER INFORMATION: Description of Artificial Sequence: Synthetic
    polypeptide

<400> SEQUENCE: 68

Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Arg Asn
            20                  25                  30

Pro Val Asn Trp Tyr Gln Gln Leu Pro Gly Thr Ala Pro Lys Leu Leu
        35                  40                  45

Ile Tyr Leu Asp Asn Leu Arg Leu Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser His
                85                  90                  95

Pro Gly Trp Thr Phe Gly Gly Gly Thr Lys Leu Thr Val Leu
            100                 105                 110

<210> SEQ ID NO 69
<211> LENGTH: 110
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 69

Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Arg Asn
            20                  25                  30

Asp Val Asn Trp Tyr Gln Gln Leu Pro Gly Thr Ala Pro Lys Leu Leu
        35                  40                  45

Ile Tyr Leu Asn Asn Gln Arg Leu Gly Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser His
                85                  90                  95

Pro Gly Trp Thr Phe Gly Gly Gly Thr Lys Leu Thr Val Leu
            100                 105                 110

<210> SEQ ID NO 70
<211> LENGTH: 110
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 70

Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Arg Asn
            20                  25                  30

Pro Val Asn Trp Tyr Gln Gln Leu Pro Gly Thr Ala Pro Lys Leu Leu
        35                  40                  45

Ile Tyr Leu Asn Asn Gln Arg Pro Ser Gly Val Pro Asp Arg Phe Ser

```
                  50                  55                  60
Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Thr Trp Asp Asp Ser His
                 85                  90                  95

Pro Gly Trp Thr Phe Gly Gly Gly Thr Lys Leu Thr Val Leu
            100                 105                 110
```

<210> SEQ ID NO 71
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 71

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Leu Gly Tyr Ser Thr Ile Asp Tyr Trp Gly Arg Gly Thr Leu
            100                 105                 110

Val Thr Val Ser Ser
        115
```

<210> SEQ ID NO 72
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 72

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Leu Gly Tyr Ser Thr Ile Asp Tyr Trp Gly Arg Gly Thr Leu
            100                 105                 110

Val Thr Val Ser Ser
```

<210> SEQ ID NO 73
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Ser Thr Ile Asp Tyr Trp Gly Arg Gly Thr Leu
            100                 105                 110

Val Thr Val Ser Ser
        115

<210> SEQ ID NO 74
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Tyr Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Ser Thr Ile Asp Lys Trp Gly Arg Gly Thr Leu
            100                 105                 110

Val Thr Val Ser Ser
        115

<210> SEQ ID NO 75
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 75

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Tyr Ser Trp Val Arg Gln Ala Pro Gly Lys Gly Leu Glu Trp Val
        35                  40                  45
Ser Leu Ile Trp Gly Ser Trp Gly Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Leu Gly Tyr Ser Thr Ile Asp Met Trp Gly Arg Gly Thr Leu
            100                 105                 110
Val Thr Val Ser Ser
        115
```

<210> SEQ ID NO 76
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 76

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Tyr Ser Trp Val Arg Gln Ala Pro Gly Lys Gly Leu Glu Trp Val
        35                  40                  45
Ser Ala Ile Ser Gly Ser Gly Gly Arg Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Leu Gly Tyr Ser Thr Ile Asp Leu Trp Gly Arg Gly Thr Leu
            100                 105                 110
Val Thr Val Ser Ser
        115
```

<210> SEQ ID NO 77
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 77

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
```

Ala Tyr Ser Trp Val Arg Gln Ala Pro Gly Lys Gly Leu Glu Trp Val
            35                  40                  45

Ser Ala Ile Ser Gly Ser Trp Gly Arg Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Ser Thr Ile Asp Leu Trp Gly Arg Gly Thr Leu
            100                 105                 110

Val Thr Val Ser Ser
        115

<210> SEQ ID NO 78
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Ser Thr Ile Asp Tyr Trp Gly Arg Gly Thr Leu
            100                 105                 110

Val Thr Val Ser Ser
        115

<210> SEQ ID NO 79
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Gly Arg Val Asp Glu Trp Gly Arg Gly Thr Leu
            100                 105                 110

Val Thr Val Ser Ser
        115

<210> SEQ ID NO 80
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Tyr Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Gly Arg Val Asp Glu Trp Gly Arg Gly Thr Leu
            100                 105                 110

Val Thr Val Ser Ser
        115

<210> SEQ ID NO 81
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Tyr Ser Trp Val Arg Gln Ala Pro Gly Lys Gly Leu Glu Trp Val
        35                  40                  45

Ser Leu Ile Trp Gly Ser Trp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Gly Arg Val Asp Glu Trp Gly Arg Gly Thr Leu
            100                 105                 110

Val Thr Val Ser Ser
        115

<210> SEQ ID NO 82
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Tyr Ser Trp Val Arg Gln Ala Pro Gly Lys Gly Leu Glu Trp Val
        35                  40                  45

Ser Ala Ile Ser Gly Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Gly Arg Val Asp Glu Trp Gly Arg Gly Thr Leu
            100                 105                 110

Val Thr Val Ser Ser
        115

<210> SEQ ID NO 83
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Tyr Ser Trp Val Arg Gln Ala Pro Gly Lys Gly Leu Glu Trp Val
        35                  40                  45

Ser Ala Ile Ser Gly Ser Trp Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Gly Arg Val Asp Glu Trp Gly Arg Gly Thr Leu
            100                 105                 110

Val Thr Val Ser Ser
        115

<210> SEQ ID NO 84
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Gly Arg Val Asp Glu Trp Gly Arg Gly Thr Leu
            100                 105                 110

Val Thr Val Ser Ser
        115

<210> SEQ ID NO 85
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Lys Gly Tyr Tyr Trp Tyr Met Asp Val Trp Gly Gln Gly
            100                 105                 110

Thr Met Val Thr Val Ser Ser
        115

<210> SEQ ID NO 86
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Gln Ser Val Leu Thr Gln Pro Pro Ser Val Ser Val Ser Pro Gly Gln
1               5                   10                  15

Thr Ala Thr Ile Thr Cys Ser Gly Asp Lys Val Gly Asp Lys Tyr Ala
            20                  25                  30

```
Ser Trp Tyr Gln Gln Lys Pro Gly Gln Ser Pro Val Leu Val Ile Tyr
        35                  40                  45

Glu Asp Thr Lys Arg Pro Ser Arg Ile Pro Glu Arg Phe Ser Gly Ser
 50                  55                  60

Asn Ser Gly Asn Thr Ala Thr Leu Thr Ile Ser Gly Thr Gln Ala Leu
 65                  70                  75                  80

Asp Glu Ala Asp Tyr Phe Cys Gln Ala Trp Asp Thr Ser Phe Trp Val
                 85                  90                  95

Phe Gly Gly Gly Thr Lys Leu Thr Val Leu
            100                 105

<210> SEQ ID NO 87
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
 50                  55                  60

Lys Arg Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Lys Gly Tyr Tyr Trp Tyr Met Asp Val Trp Gly Gln Gly
            100                 105                 110

Thr Met Val Thr Val Ser Ser
        115

<210> SEQ ID NO 88
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Gln Ser Val Leu Thr Gln Pro Pro Ser Val Ser Val Ser Pro Gly Gln
 1               5                  10                  15

Thr Ala Ser Ile Thr Cys Ser Gly Asp Lys Val Gly Asp Lys Tyr Ala
                 20                  25                  30

Ser Trp Tyr Gln Gln Lys Pro Gly Gln Ser Pro Val Leu Val Ile Tyr
            35                  40                  45

Glu Asp Thr Lys Arg Leu Ser Gly Ile Pro Glu Arg Phe Ser Gly Ser
 50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Thr Ser Phe Trp Val
                 85                  90                  95
```

```
Phe Gly Gly Gly Thr Lys Leu Thr Val Leu
            100                 105

<210> SEQ ID NO 89
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Trp Gly Gln Gly Thr Met Val Thr Val Ser Ser
1               5                   10

<210> SEQ ID NO 90
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gln Ser Val Leu Thr Gln Pro Pro Ser Val Ser Val Ser Pro Gly Gln
1               5                   10                  15

Thr Ala Thr Ile Thr Cys
            20

<210> SEQ ID NO 91
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gln Ser Val Leu Thr Gln Pro Pro Ser Val Ser Val Ser Pro Gly Gln
1               5                   10                  15

Thr Ala Ser Ile Thr Cys
            20

<210> SEQ ID NO 92
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Trp Tyr Gln Gln Lys Pro Gly Gln Ser Pro Val Leu Val Ile Tyr
1               5                   10                  15

<210> SEQ ID NO 93
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Arg Ile Pro Glu Arg Phe Ser Gly Ser Asn Ser Gly Asn Thr Ala Thr
1               5                   10                  15
```

```
Leu Thr Ile Ser Gly Thr Gln Ala Leu Asp Glu Ala Asp Tyr Phe Cys
            20                  25                  30
```

<210> SEQ ID NO 94
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

```
Gly Ile Pro Glu Arg Phe Ser Gly Ser Asn Ser Gly Asn Thr Ala Thr
1               5                   10                  15

Leu Thr Ile Ser Gly Thr Gln Ala Met Asp Glu Ala Asp Tyr Tyr Cys
            20                  25                  30
```

<210> SEQ ID NO 95
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

```
Ala Ile Ser Gly Ser Gly Gly Ser Thr Tyr Tyr Ala Asp Ser Val Lys
1               5                   10                  15

Arg
```

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

```
Asp Lys Gly Tyr Tyr Trp Tyr Met Asp Val
1               5                   10
```

<210> SEQ ID NO 97
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

```
Ser Gly Asp Lys Val Gly Asp Lys Tyr Ala Ser
1               5                   10
```

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

```
Glu Asp Thr Lys Arg Pro Ser
1               5
```

```
<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Glu Asp Thr Lys Arg Leu Ser
1               5

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gln Ala Trp Asp Thr Ser Phe Trp Val
1               5

<210> SEQ ID NO 101
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Arg Phe Ser Asp Phe
            20                  25                  30

Ala Met His Trp Val Arg Gln Ala Pro Gly Lys Gly Leu Glu Trp Val
        35                  40                  45

Ala Gly Ile Ser Tyr Asp Gly Gly Asn Lys Tyr Tyr Ala Asp Ser Val
    50                  55                  60

Lys Gly Arg Phe Thr Ile Ser Arg Asp Asn Ser Asn Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp His Gly Tyr Ser Gly Tyr Tyr Gly His Leu Asp Tyr Trp
            100                 105                 110

Gly Arg Gly Thr Leu Val Thr Val Ser Ser
        115                 120

<210> SEQ ID NO 102
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Gln Ser Val Val Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30
```

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                85                  90                  95

Asn Gly Arg Val Phe Gly Thr Gly Thr Lys Leu Thr Val Leu
            100                 105                 110

<210> SEQ ID NO 103
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Asp Arg Pro Asn Tyr Tyr Gly Ala Ser Gly Ser Tyr Tyr Lys
            100                 105                 110

Gln Gly Gly Asp His Trp Gly Gln Gly Thr Met Val Thr Val Ser Ser
            115                 120                 125

<210> SEQ ID NO 104
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Asn Phe Met Leu Thr Gln Pro His Ser Val Ser Glu Ser Pro Gly Gln
 1               5                  10                  15

Thr Val Thr Ile Ser Cys Thr Arg Ser Ser Gly Ser Ile Ala Ser Lys
            20                  25                  30

Tyr Val Gln Trp Tyr Gln Lys Arg Pro Gly Ser Ser Pro Thr Thr Val
            35                  40                  45

Ile Tyr Glu Asp Thr Gln Arg Pro Ser Gly Val Pro Asp Arg Phe Ser
 50                  55                  60

Gly Ser Ile Asp Ile Ser Ser Asn Ser Ala Ser Leu Thr Ile Ser Gly
 65                  70                  75                  80

Leu Arg Thr Glu Asp Glu Ala Asp Tyr Tyr Cys Gln Ser Tyr Asp Ser
                85                  90                  95

```
Thr Asn Trp Val Phe Gly Gly Gly Thr Lys Val Thr Val Leu
            100                 105                 110
```

<210> SEQ ID NO 105
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

```
Glu Val Gln Leu Leu Glu Thr Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Asn Tyr Gly Asn Leu Asp His Trp Gly Lys Gly Thr Leu
            100                 105                 110

Val Thr Val Ser Ser
        115
```

<210> SEQ ID NO 106
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

```
Gln Ser Val Leu Thr Gln Pro Pro Ser Val Ser Val Ser Pro Gly Gln
1               5                   10                  15

Thr Ala Ser Ile Thr Cys Ser Gly Asp Lys Val Gly Asp Lys Tyr Ala
            20                  25                  30

Ser Trp Tyr Gln Gln Lys Pro Gly Gln Ser Pro Val Leu Val Ile Tyr
        35                  40                  45

Gln Asp Arg Lys Arg Pro Ser Gly Ile Pro Glu Arg Phe Ser Gly Ser
50                  55                  60

Asn Ser Gly Asn Thr Ala Thr Leu Thr Ile Ser Gly Thr Gln Pro Met
65                  70                  75                  80

Asp Glu Ala Asp Tyr Tyr Cys Gln Ala Trp Asp Ser Ser His Trp Val
                85                  90                  95

Phe Gly Gly Gly Thr Lys Leu Thr Val Leu
            100                 105
```

<210> SEQ ID NO 107
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 107

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ile Met Gly Trp Val Arg Gln Ala Pro Gly Lys Gly Leu Glu Trp Val
        35                  40                  45

Ser Ser Ile Ser Ser Ser Gly Gly Ala Thr Ile Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Met Ala Val Tyr Tyr Cys
                85                  90                  95

Ala Lys Asp His Leu Gly Gly His Gly Met Asp Val Trp Gly Gln Gly
            100                 105                 110

Thr Thr Val Thr Val Ser Ser
            115

<210> SEQ ID NO 108
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Phe Gln Gln Lys Pro Gly Lys Ala Pro Lys Ser Leu Ile
        35                  40                  45

Phe Ala Ala Ser Ser Leu Glu Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 109
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Glu Tyr
            20                  25                  30

Gln Met Gly Trp Val Arg Gln Ala Pro Gly Lys Gly Leu Glu Trp Val
        35                  40                  45

Ser Tyr Ile Arg Ser Ser Gly Gly Gln Thr Ile Tyr Ala Asp Ser Val
```

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Arg Thr Tyr Ser Ser Gly Trp His Ile Asp Tyr Trp Gly Gln
                100                 105                 110

Gly Thr Leu Val Thr Val Ser Ser
            115                 120

<210> SEQ ID NO 110
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Asp Ile Gln Met Thr Gln Ser Pro Asp Ser Leu Ser Ala Ser Val Gly
  1               5                  10                  15

Asp Arg Val Thr Ile Thr Cys Arg Ala Ser Gln Ser Ile Ser Arg Tyr
                 20                  25                  30

Leu Asn Trp Tyr Gln Gln Lys Pro Gly Lys Ala Pro Lys Leu Leu Ile
             35                  40                  45

Tyr Gly Ala Ser Ser Leu Gln Ser Gly Val Pro Ser Arg Phe Ser Gly
         50                  55                  60

Ser Gly Ser Gly Thr Asp Phe Ser Leu Thr Ile Ser Ser Leu Gln Leu
 65                  70                  75                  80

Glu Asp Phe Ala Thr Tyr Tyr Cys Gln Gln Ser Tyr Arg Thr Pro Leu
                 85                  90                  95

Thr Phe Gly Gly Gly Thr Lys Val Glu Ile Gln
                100                 105

<210> SEQ ID NO 111
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Lys Gly Tyr Tyr Trp Tyr Met Asp Val Trp Gly Gln Gly
                100                 105                 110

Thr Met Val Thr Val Ser Ser
```

```
<210> SEQ ID NO 112
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Gln Ser Val Leu Thr Gln Pro Pro Ser Val Ser Val Ser Pro Gly Gln
1               5                   10                  15

Thr Ala Ser Ile Thr Cys Ser Gly Asp Lys Val Gly Asp Lys Tyr Ala
            20                  25                  30

Ser Trp Tyr Gln Gln Lys Pro Gly Gln Ser Pro Val Leu Val Ile Tyr
        35                  40                  45

Glu Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Thr Ser Phe Trp Val
                85                  90                  95

Phe Gly Gly Gly Thr Lys Leu Thr Val Leu
            100                 105

<210> SEQ ID NO 113
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Val
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Lys Gly Tyr Tyr Trp Tyr Met Asp Val Trp Gly Gln Gly
            100                 105                 110

Thr Met Val Thr Val Ser Ser
        115

<210> SEQ ID NO 114
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Arg Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Lys Gly Tyr Tyr Trp Tyr Met Asp Val Trp Gly Gln Gly
                100                 105                 110

Thr Met Val Thr Val Ser Ser
        115

<210> SEQ ID NO 115
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Pro Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Lys Gly Tyr Tyr Trp Tyr Met Asp Val Trp Gly Gln Gly
                100                 105                 110

Thr Met Val Thr Val Ser Ser
        115

<210> SEQ ID NO 116
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

```
Ser Ala Ile Ser Gly Ser Gly Gly Ser Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Lys Gly Tyr Tyr Trp Tyr Met Asp Val Trp Gly Gln Gly
                100                 105                 110

Thr Met Val Thr Val Ser Ser
            115

<210> SEQ ID NO 117
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
    50                  55                  60

Lys Arg Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Lys Gly Tyr Tyr Trp Tyr Met Asp Val Trp Gly Gln Gly
                100                 105                 110

Thr Met Val Thr Val Ser Ser
            115

<210> SEQ ID NO 118
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Gln Ser Val Leu Thr Gln Pro Pro Ser Val Ser Val Ser Pro Gly Gln
1               5                   10                  15

Thr Ala Ser Ile Thr Cys Ser Gly Asp Lys Val Gly Asp Lys Tyr Ala
                20                  25                  30

Ser Trp Tyr Gln Gln Lys Pro Gly Gln Ser Pro Val Leu Val Ile Tyr
            35                  40                  45

Glu Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Thr Ser Phe Trp Val
                85                  90                  95
```

```
Phe Gly Gly Gly Thr Lys Leu Thr Val Leu Leu
            100                 105
```

<210> SEQ ID NO 119
<211> LENGTH: 108
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 119

```
Gln Ser Val Leu Thr Gln Pro Pro Ser Val Ser Val Ser Pro Gly Gln
1               5                   10                  15

Thr Ala Ser Ile Thr Cys Ser Gly Asp Lys Val Gly Asp Lys Tyr Ala
            20                  25                  30

Ser Trp Tyr Gln Gln Lys Pro Gly Gln Ser Pro Val Leu Val Ile Tyr
        35                  40                  45

Glu Asp Thr Lys Tyr Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Thr Ser Phe Trp Val
                85                  90                  95

Phe Gly Gly Gly Thr Lys Leu Thr Val Leu Val Leu
            100                 105
```

<210> SEQ ID NO 120
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 120

```
Gln Ser Val Leu Thr Gln Pro Pro Ser Val Ser Val Ser Pro Gly Gln
1               5                   10                  15

Thr Ala Ser Ile Thr Cys Ser Gly Asp Lys Val Gly Asp Lys Tyr Ala
            20                  25                  30

Ser Trp Tyr Gln Gln Lys Pro Gly Gln Ser Val Leu Val Ile Tyr Glu
        35                  40                  45

Asp Thr Lys Arg His Ser Gly Ile Pro Glu Arg Phe Ser Gly Ser Asn
    50                  55                  60

Ser Gly Asn Thr Ala Thr Leu Thr Ile Ser Gly Thr Gln Ala Met Asp
65                  70                  75                  80

Glu Ala Asp Tyr Tyr Cys Gln Ala Trp Asp Thr Ser Phe Trp Val Phe
                85                  90                  95

Gly Gly Gly Thr Lys Leu Thr Val Leu Val Leu
            100                 105
```

<210> SEQ ID NO 121
<211> LENGTH: 108
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 121

```
Gln Ser Val Leu Thr Gln Pro Pro Ser Val Ser Val Ser Pro Gly Gln
1               5                   10                  15

Thr Ala Ser Ile Thr Cys Ser Gly Asp Lys Val Gly Asp Lys Tyr Ala
            20                  25                  30

Ser Trp Tyr Gln Gln Lys Pro Gly Gln Ser Pro Val Leu Val Ile Tyr
        35                  40                  45

Glu Asp Thr Lys Arg Leu Ser Gly Ile Pro Glu Arg Phe Ser Gly Ser
    50                  55                  60

Asn Arg Gly Asn Thr Ala Thr Leu Thr Ile Ser Gly Thr Gln Ala Met
65                  70                  75                  80

Asp Glu Ala Asp Tyr Tyr Cys Gln Ala Trp Asp Thr Ser Phe Trp Val
                85                  90                  95

Phe Gly Gly Gly Thr Lys Leu Thr Val Leu Val Leu
            100                 105

<210> SEQ ID NO 122
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Gly Ile Pro Glu Arg Phe Ser Gly Ser Asn Arg Gly Asn Thr Ala Thr
1               5                   10                  15

Leu Thr Ile Ser Gly Thr Gln Ala Met Asp Glu Ala Asp Tyr Tyr Cys
            20                  25                  30

<210> SEQ ID NO 123
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ser Val Ala Met Ser
1               5

<210> SEQ ID NO 124
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Ser Tyr Ala Arg Ser
1               5

<210> SEQ ID NO 125
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Ala Ile Ser Gly Ser Gly Gly Ser Pro Tyr Tyr Ala Asp Ser Val Lys
1               5                   10                  15
```

Gly

<210> SEQ ID NO 126
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Ala Ile Ser Gly Ser Gly Gly Ser Thr Tyr Tyr Gly Asp Ser Val Lys
1               5                   10                  15

Gly

<210> SEQ ID NO 127
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Glu Asp Ser Lys Arg Pro Ser
1               5

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Glu Asp Thr Lys Tyr Pro Ser
1               5

<210> SEQ ID NO 129
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Glu Asp Thr Lys Arg Leu Ser
1               5

<210> SEQ ID NO 130
<211> LENGTH: 574
<212> TYPE: PRT
<213> ORGANISM: Homo sapiens

<400> SEQUENCE: 130

Met Cys Pro Arg Ala Ala Arg Ala Pro Ala Thr Leu Leu Ala Leu
1               5                   10                  15

Gly Ala Val Leu Trp Pro Ala Ala Gly Ala Trp Glu Leu Thr Ile Leu
                20                  25                  30

His Thr Asn Asp Val His Ser Arg Leu Glu Gln Thr Ser Glu Asp Ser
            35                  40                  45

Ser Lys Cys Val Asn Ala Ser Arg Cys Met Gly Gly Val Ala Arg Leu

```
            50                  55                  60
Phe Thr Lys Val Gln Gln Ile Arg Arg Ala Glu Pro Asn Val Leu Leu
 65                      70                  75                  80

Leu Asp Ala Gly Asp Gln Tyr Gln Gly Thr Ile Trp Phe Thr Val Tyr
                     85                  90                  95

Lys Gly Ala Glu Val Ala His Phe Met Asn Ala Leu Arg Tyr Asp Ala
                100                 105                 110

Met Ala Leu Gly Asn His Glu Phe Asp Asn Gly Val Glu Gly Leu Ile
                115                 120                 125

Glu Pro Leu Leu Lys Glu Ala Lys Phe Pro Ile Leu Ser Ala Asn Ile
130                 135                 140

Lys Ala Lys Gly Pro Leu Ala Ser Gln Ile Ser Gly Leu Tyr Leu Pro
145                 150                 155                 160

Tyr Lys Val Leu Pro Val Gly Asp Glu Val Gly Ile Val Gly Tyr
                165                 170                 175

Thr Ser Lys Glu Thr Pro Phe Leu Ser Asn Pro Gly Thr Asn Leu Val
                180                 185                 190

Phe Glu Asp Glu Ile Thr Ala Leu Gln Pro Glu Val Asp Lys Leu Lys
                195                 200                 205

Thr Leu Asn Val Asn Lys Ile Ile Ala Leu Gly His Ser Gly Phe Glu
210                 215                 220

Met Asp Lys Leu Ile Ala Gln Lys Val Arg Gly Val Asp Val Val
225                 230                 235                 240

Gly Gly His Ser Asn Thr Phe Leu Tyr Thr Gly Asn Pro Pro Ser Lys
                245                 250                 255

Glu Val Pro Ala Gly Lys Tyr Pro Phe Ile Val Thr Ser Asp Asp Gly
                260                 265                 270

Arg Lys Val Pro Val Val Gln Ala Tyr Ala Phe Gly Lys Tyr Leu Gly
                275                 280                 285

Tyr Leu Lys Ile Glu Phe Asp Glu Arg Gly Asn Val Ile Ser Ser His
                290                 295                 300

Gly Asn Pro Ile Leu Leu Asn Ser Ser Ile Pro Glu Asp Pro Ser Ile
305                 310                 315                 320

Lys Ala Asp Ile Asn Lys Trp Arg Ile Lys Leu Asp Asn Tyr Ser Thr
                325                 330                 335

Gln Glu Leu Gly Lys Thr Ile Val Tyr Leu Asp Gly Ser Ser Gln Ser
                340                 345                 350

Cys Arg Phe Arg Glu Cys Asn Met Gly Asn Leu Ile Cys Asp Ala Met
                355                 360                 365

Ile Asn Asn Asn Leu Arg His Thr Asp Glu Met Phe Trp Asn His Val
370                 375                 380

Ser Met Cys Ile Leu Asn Gly Gly Gly Ile Arg Ser Pro Ile Asp Glu
385                 390                 395                 400

Arg Asn Asn Gly Thr Ile Thr Trp Glu Asn Leu Ala Ala Val Leu Pro
                405                 410                 415

Phe Gly Gly Thr Phe Asp Leu Val Gln Leu Lys Gly Ser Thr Leu Lys
                420                 425                 430

Lys Ala Phe Glu His Ser Val His Arg Tyr Gly Gln Ser Thr Gly Glu
                435                 440                 445

Phe Leu Gln Val Gly Gly Ile His Val Val Tyr Asp Leu Ser Arg Lys
                450                 455                 460

Pro Gly Asp Arg Val Val Lys Leu Asp Val Leu Cys Thr Lys Cys Arg
465                 470                 475                 480
```

```
Val Pro Ser Tyr Asp Pro Leu Lys Met Asp Glu Val Tyr Lys Val Ile
            485                 490                 495

Leu Pro Asn Phe Leu Ala Asn Gly Gly Asp Gly Phe Gln Met Ile Lys
            500                 505                 510

Asp Glu Leu Leu Arg His Asp Ser Gly Asp Gln Asp Ile Asn Val Val
            515                 520                 525

Ser Thr Tyr Ile Ser Lys Met Lys Val Ile Tyr Pro Ala Val Glu Gly
    530                 535                 540

Arg Ile Lys Phe Ser Thr Gly Ser His Cys His Gly Ser Phe Ser Leu
545                 550                 555                 560

Ile Phe Leu Ser Leu Trp Ala Val Ile Phe Val Leu Tyr Gln
                565                 570

<210> SEQ ID NO 131
<211> LENGTH: 411
<212> TYPE: PRT
<213> ORGANISM: Homo sapiens

<400> SEQUENCE: 131

Met Pro Ile Met Gly Ser Ser Val Tyr Ile Thr Val Glu Leu Ala Ile
1               5                   10                  15

Ala Val Leu Ala Ile Leu Gly Asn Val Leu Val Cys Trp Ala Val Trp
            20                  25                  30

Leu Asn Ser Asn Leu Gln Asn Val Thr Asn Tyr Phe Val Val Ser Leu
        35                  40                  45

Ala Ala Ala Asp Ile Ala Val Gly Val Leu Ala Ile Pro Phe Ala Ile
    50                  55                  60

Thr Ile Thr Gly Phe Cys Ala Ala Cys His Gly Cys Leu Phe Ile Ala
65                  70                  75                  80

Cys Phe Val Leu Val Leu Thr Gln Ser Ser Ile Phe Ser Leu Leu Ala
                85                  90                  95

Ile Ala Ile Asp Arg Tyr Ile Ala Ile Arg Ile Pro Leu Arg Tyr Asn
            100                 105                 110

Gly Leu Val Thr Gly Thr Arg Ala Lys Gly Ile Ile Ala Ile Cys Trp
        115                 120                 125

Val Leu Ser Phe Ala Ile Gly Leu Thr Pro Met Leu Gly Trp Asn Asn
    130                 135                 140

Cys Gly Gln Pro Lys Glu Gly Lys Asn His Ser Gln Gly Cys Gly Glu
145                 150                 155                 160

Gly Gln Val Ala Cys Leu Phe Glu Asp Val Val Pro Met Asn Tyr Met
                165                 170                 175

Val Tyr Phe Asn Phe Phe Ala Cys Val Leu Val Pro Leu Leu Leu Met
            180                 185                 190

Leu Gly Val Tyr Leu Arg Ile Phe Leu Ala Ala Arg Arg Gln Leu Lys
        195                 200                 205

Gln Met Glu Ser Gln Pro Leu Pro Gly Glu Arg Ala Arg Ser Thr Leu
    210                 215                 220

Gln Lys Glu Val His Ala Ala Lys Ser Leu Ala Ile Ile Val Gly Leu
225                 230                 235                 240

Phe Ala Leu Cys Trp Leu Pro Leu His Ile Ile Asn Cys Phe Thr Phe
                245                 250                 255

Phe Cys Pro Asp Cys Ser His Ala Pro Leu Trp Leu Met Tyr Leu Ala
            260                 265                 270

Ile Val Leu Ser His Thr Asn Ser Val Val Asn Pro Phe Ile Tyr Ala
```

```
                275                 280                 285
Tyr Arg Ile Arg Glu Phe Arg Gln Thr Phe Arg Lys Ile Ile Arg Ser
    290                 295                 300

His Val Leu Arg Gln Gln Glu Pro Phe Lys Ala Ala Gly Thr Ser Ala
305                 310                 315                 320

Arg Val Leu Ala Ala His Gly Ser Asp Gly Glu Gln Val Ser Leu Arg
                325                 330                 335

Leu Asn Gly His Pro Pro Gly Val Trp Ala Asn Gly Ser Ala Pro His
            340                 345                 350

Pro Glu Arg Arg Pro Asn Gly Tyr Ala Leu Gly Leu Val Ser Gly Gly
                355                 360                 365

Ser Ala Gln Glu Ser Gln Gly Asn Thr Gly Leu Pro Asp Val Glu Leu
    370                 375                 380

Leu Ser His Glu Leu Lys Gly Val Cys Pro Glu Pro Pro Gly Leu Asp
385                 390                 395                 400

Asp Pro Leu Ala Gln Asp Gly Ala Gly Val Ser
                405                 410

<210> SEQ ID NO 132
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Pro, Glu or Asp

<400> SEQUENCE: 132

Ser Gly Ser Leu Ser Asn Ile Gly Arg Asn Xaa Val Asn
1               5                   10

<210> SEQ ID NO 133
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Asn or Asp
<220> FEATURE:
<221> NAME/KEY: MOD_RES
<222> LOCATION: (4)..(4)
<223> OTHER INFORMATION: Gln or Leu
<220> FEATURE:
<221> NAME/KEY: MOD_RES
<222> LOCATION: (6)..(6)
<223> OTHER INFORMATION: Leu or Pro
<220> FEATURE:
<221> NAME/KEY: MOD_RES
<222> LOCATION: (7)..(7)
<223> OTHER INFORMATION: Gly or Ser

<400> SEQUENCE: 133

Leu Xaa Asn Xaa Arg Xaa Xaa
1               5

<210> SEQ ID NO 134
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Leu or His
<220> FEATURE:
<221> NAME/KEY: MOD_RES
<222> LOCATION: (8)..(8)
<223> OTHER INFORMATION: Lys, Pro, Ile or Asn
<220> FEATURE:
<221> NAME/KEY: MOD_RES
<222> LOCATION: (11)..(11)
<223> OTHER INFORMATION: Leu or Thr

<400> SEQUENCE: 134

Ala Thr Trp Asp Asp Ser Xaa Xaa Gly Trp Xaa
1               5                   10

<210> SEQ ID NO 135
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Met or Tyr

<400> SEQUENCE: 135

Ser Tyr Ala Xaa Ser
1               5

<210> SEQ ID NO 136
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Leu or Ala
<220> FEATURE:
<221> NAME/KEY: MOD_RES
<222> LOCATION: (3)..(3)
<223> OTHER INFORMATION: Trp or Ser
<220> FEATURE:
<221> NAME/KEY: MOD_RES
<222> LOCATION: (6)..(6)
<223> OTHER INFORMATION: Trp or Gly
<220> FEATURE:
<221> NAME/KEY: MOD_RES
<222> LOCATION: (8)..(8)
<223> OTHER INFORMATION: Ser or Arg

<400> SEQUENCE: 136

Xaa Ile Xaa Gly Ser Xaa Gly Xaa Thr Tyr Tyr Ala Asp Ser Val Lys
1               5                   10                  15
Gly

<210> SEQ ID NO 137
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (4)..(4)
<223> OTHER INFORMATION: Gly or Ser
<220> FEATURE:
<221> NAME/KEY: MOD_RES
<222> LOCATION: (5)..(5)
<223> OTHER INFORMATION: Arg or Thr
<220> FEATURE:
<221> NAME/KEY: MOD_RES
<222> LOCATION: (6)..(6)
<223> OTHER INFORMATION: Val or Ile
<220> FEATURE:
<221> NAME/KEY: MOD_RES
<222> LOCATION: (8)..(8)
<223> OTHER INFORMATION: Tyr, Lys, Met, Leu or Glu

<400> SEQUENCE: 137

Leu Gly Tyr Xaa Xaa Xaa Asp Xaa
1               5

<210> SEQ ID NO 138
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(22)
<223> OTHER INFORMATION: This region may encompass
      'LPVLTQPPSVSGTPGQRVTISC' or 'QSVLTQPPSASGTPGQRVTISC'
<220> FEATURE:
<221> NAME/KEY: MOD_RES
<222> LOCATION: (1)..(1)
<223> OTHER INFORMATION: Leu or Gln
<220> FEATURE:
<221> NAME/KEY: MOD_RES
<222> LOCATION: (2)..(2)
<223> OTHER INFORMATION: Pro or Ser
<220> FEATURE:
<221> NAME/KEY: MOD_RES
<222> LOCATION: (10)..(10)
<223> OTHER INFORMATION: Val or Ala
<220> FEATURE:
<221> NAME/KEY: MOD_RES
<222> LOCATION: (33)..(33)
<223> OTHER INFORMATION: Pro, Glu or Asp
<220> FEATURE:
<221> NAME/KEY: MISC_FEATURE
<222> LOCATION: (36)..(50)
<223> OTHER INFORMATION: This region may encompass 'WYKQVPGTAPKLLIY' or
      'WYQQLPGTAPKLLIY'
<220> FEATURE:
<221> NAME/KEY: MOD_RES
<222> LOCATION: (38)..(38)
<223> OTHER INFORMATION: Lys or Gln
<220> FEATURE:
<221> NAME/KEY: MOD_RES
<222> LOCATION: (40)..(40)
<223> OTHER INFORMATION: Val or Leu
<220> FEATURE:
<221> NAME/KEY: MOD_RES
<222> LOCATION: (52)..(52)
<223> OTHER INFORMATION: Asn or Asp
<220> FEATURE:
<221> NAME/KEY: MOD_RES
<222> LOCATION: (54)..(54)
<223> OTHER INFORMATION: Gln or Leu
<220> FEATURE:
<221> NAME/KEY: MOD_RES
<222> LOCATION: (56)..(56)
<223> OTHER INFORMATION: Leu or Pro
<220> FEATURE:
<221> NAME/KEY: MOD_RES
<222> LOCATION: (57)..(57)
```

-continued

```
<223> OTHER INFORMATION: Gly or Ser
<220> FEATURE:
<221> NAME/KEY: MOD_RES
<222> LOCATION: (96)..(96)
<223> OTHER INFORMATION: Leu or His
<220> FEATURE:
<221> NAME/KEY: MOD_RES
<222> LOCATION: (97)..(97)
<223> OTHER INFORMATION: Lys, Pro, Ile or Asn
<220> FEATURE:
<221> NAME/KEY: MOD_RES
<222> LOCATION: (100)..(100)
<223> OTHER INFORMATION: Leu or Thr

<400> SEQUENCE: 138

Xaa Xaa Val Leu Thr Gln Pro Pro Ser Xaa Ser Gly Thr Pro Gly Gln
1               5                   10                  15

Arg Val Thr Ile Ser Cys Ser Gly Ser Leu Ser Asn Ile Gly Arg Asn
            20                  25                  30

Xaa Val Asn Trp Tyr Xaa Gln Xaa Pro Gly Thr Ala Pro Lys Leu Leu
        35                  40                  45

Ile Tyr Leu Xaa Asn Xaa Arg Xaa Xaa Gly Val Pro Asp Arg Phe Ser
    50                  55                  60

Gly Ser Lys Ser Gly Thr Ser Ala Ser Leu Ala Ile Ser Gly Leu Gln
65              70                  75                  80

Ser Glu Asp Glu Ala Asp Tyr Tyr Cys Ala Thr Trp Asp Asp Ser Xaa
                85                  90                  95

Xaa Gly Trp Xaa Phe Gly Gly Gly Thr Lys Leu Thr Val Leu
            100                 105                 110

<210> SEQ ID NO 139
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: Met or Tyr
<220> FEATURE:
<221> NAME/KEY: MOD_RES
<222> LOCATION: (50)..(50)
<223> OTHER INFORMATION: Leu or Ala
<220> FEATURE:
<221> NAME/KEY: MOD_RES
<222> LOCATION: (52)..(52)
<223> OTHER INFORMATION: Trp or Ser
<220> FEATURE:
<221> NAME/KEY: MOD_RES
<222> LOCATION: (55)..(55)
<223> OTHER INFORMATION: Trp or Gly
<220> FEATURE:
<221> NAME/KEY: MOD_RES
<222> LOCATION: (57)..(57)
<223> OTHER INFORMATION: Ser or Arg
<220> FEATURE:
<221> NAME/KEY: MOD_RES
<222> LOCATION: (102)..(102)
<223> OTHER INFORMATION: Gly or Ser
<220> FEATURE:
<221> NAME/KEY: MOD_RES
<222> LOCATION: (103)..(103)
<223> OTHER INFORMATION: Arg or Thr
<220> FEATURE:
<221> NAME/KEY: MOD_RES
<222> LOCATION: (104)..(104)
<223> OTHER INFORMATION: Val or Ile
<220> FEATURE:
<221> NAME/KEY: MOD_RES
```

```
<222> LOCATION: (106)..(106)
<223> OTHER INFORMATION: Tyr, Lys, Met, Leu or Glu

<400> SEQUENCE: 139

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Xaa Ser Trp Val Arg Gln Ala Pro Gly Lys Gly Leu Glu Trp Val
        35                  40                  45

Ser Xaa Ile Xaa Gly Ser Xaa Gly Xaa Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Xaa Xaa Xaa Asp Xaa Trp Gly Arg Gly Thr Leu
            100                 105                 110

Val Thr Val Ser Ser
        115

<210> SEQ ID NO 140
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (5)..(5)
<223> OTHER INFORMATION: Arg or Tyr
<220> FEATURE:
<221> NAME/KEY: MOD_RES
<222> LOCATION: (6)..(6)
<223> OTHER INFORMATION: His, Pro or Leu

<400> SEQUENCE: 140

Glu Asp Xaa Lys Xaa Xaa Ser
1               5

<210> SEQ ID NO 141
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Tyr or Val
<220> FEATURE:
<221> NAME/KEY: MOD_RES
<222> LOCATION: (4)..(4)
<223> OTHER INFORMATION: Met or Arg

<400> SEQUENCE: 141

Ser Xaa Ala Xaa Ser
1               5

<210> SEQ ID NO 142
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Thr or Pro
<220> FEATURE:
<221> NAME/KEY: MOD_RES
<222> LOCATION: (12)..(12)
<223> OTHER INFORMATION: Ala or Gly
<220> FEATURE:
<221> NAME/KEY: MOD_RES
<222> LOCATION: (17)..(17)
<223> OTHER INFORMATION: Gly or Arg

<400> SEQUENCE: 142

Ala Ile Ser Gly Ser Gly Gly Ser Xaa Tyr Tyr Xaa Asp Ser Val Lys
1               5                   10                  15
Xaa

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Asp Lys Gly Tyr Tyr Trp Tyr Met
1               5

<210> SEQ ID NO 144
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(22)
<223> OTHER INFORMATION: This region may encompass
      'QSVLTQPPSVSVSPGQTATITC' or 'QSVLTQPPSVSVSPGQTASITC'
<220> FEATURE:
<221> NAME/KEY: MOD_RES
<222> LOCATION: (19)..(19)
<223> OTHER INFORMATION: Thr or Ser
<220> FEATURE:
<221> NAME/KEY: MOD_RES
<222> LOCATION: (51)..(51)
<223> OTHER INFORMATION: Pro or Leu
<220> FEATURE:
<221> NAME/KEY: MOD_RES
<222> LOCATION: (53)..(53)
<223> OTHER INFORMATION: Arg or Tyr
<220> FEATURE:
<221> NAME/KEY: MOD_RES
<222> LOCATION: (54)..(54)
<223> OTHER INFORMATION: His, Pro or Leu
<220> FEATURE:
<221> NAME/KEY: MOD_RES
<222> LOCATION: (56)..(56)
<223> OTHER INFORMATION: Arg or Gly
<220> FEATURE:
<221> NAME/KEY: MOD_RES
<222> LOCATION: (66)..(66)
<223> OTHER INFORMATION: Ser or Arg
<220> FEATURE:
<221> NAME/KEY: MOD_RES
```

```
<222> LOCATION: (80)..(80)
<223> OTHER INFORMATION: Leu or Met
<220> FEATURE:
<221> NAME/KEY: MOD_RES
<222> LOCATION: (86)..(86)
<223> OTHER INFORMATION: Phe or Tyr
<220> FEATURE:
<221> NAME/KEY: MISC_FEATURE
<222> LOCATION: (56)..(87)
<223> OTHER INFORMATION: This region may encompass
      'RIPERFSGSNSGNTATLTISGTQALDEADYFC,'
      'GIPERFSGSNSGNTATLTISGTQAMDEADYYC' or
      'GIPERFSGSNRGNTATLTISGTQAMDEADYYC'

<400> SEQUENCE: 144

Gln Ser Val Leu Thr Gln Pro Pro Ser Val Ser Val Ser Pro Gly Gln
1               5                   10                  15

Thr Ala Xaa Ile Thr Cys Ser Gly Asp Lys Val Gly Asp Lys Tyr Ala
            20                  25                  30

Ser Trp Tyr Gln Gln Lys Pro Gly Gln Ser Pro Val Leu Val Ile Tyr
        35                  40                  45

Glu Asp Xaa Lys Xaa Xaa Ser Xaa Ile Pro Glu Arg Phe Ser Gly Ser
    50                  55                  60

Asn Xaa Gly Asn Thr Ala Thr Leu Thr Ile Ser Gly Thr Gln Ala Xaa
65                  70                  75                  80

Asp Glu Ala Asp Tyr Xaa Cys Gln Ala Trp Asp Thr Ser Phe Trp Val
                85                  90                  95

Phe Gly Gly Gly Thr Lys Leu Thr Val Leu
                100                 105

<210> SEQ ID NO 145
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (32)..(32)
<223> OTHER INFORMATION: Tyr or Val
<220> FEATURE:
<221> NAME/KEY: MOD_RES
<222> LOCATION: (34)..(34)
<223> OTHER INFORMATION: Met or Arg
<220> FEATURE:
<221> NAME/KEY: MOD_RES
<222> LOCATION: (58)..(58)
<223> OTHER INFORMATION: Thr or Pro
<220> FEATURE:
<221> NAME/KEY: MOD_RES
<222> LOCATION: (61)..(61)
<223> OTHER INFORMATION: Ala or Gly
<220> FEATURE:
<221> NAME/KEY: MOD_RES
<222> LOCATION: (66)..(66)
<223> OTHER INFORMATION: Gly or Arg

<400> SEQUENCE: 145

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Xaa
            20                  25                  30

Ala Xaa Ser Trp Val Arg Gln Ala Pro Gly Lys Gly Leu Glu Trp Val
        35                  40                  45

Ser Ala Ile Ser Gly Ser Gly Gly Ser Xaa Tyr Tyr Xaa Asp Ser Val
    50                  55                  60
```

-continued

Lys Xaa Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Lys Gly Tyr Tyr Trp Tyr Met Trp Gly Gln Gly Thr Met
            100                 105                 110

Val Thr Val Ser Ser
        115

<210> SEQ ID NO 146
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 146

His His His His His His
1               5

<210> SEQ ID NO 147
<211> LENGTH: 115
<212> TYPE: PRT
<213> ORGANISM: Homo sapiens

<400> SEQUENCE: 147

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Trp Tyr Phe Asp Leu Trp Gly Arg Gly Thr Leu Val Thr
            100                 105                 110

Val Ser Ser
        115

<210> SEQ ID NO 148
<211> LENGTH: 108
<212> TYPE: PRT
<213> ORGANISM: Homo sapiens

<400> SEQUENCE: 148

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
                20                  25                  30

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
        50                  55                  60

```
-continued

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Val Val Phe Gly Gly Gly Thr Lys Leu Thr Val Leu
            100                 105
```

THERAPEUTIC COMBINATIONS COMPRISING ANTI-CD73 ANTIBODIES AND USES THEREOF

CROSS-REFERENCE TO RELATED APPLICATIONS

This application claims benefit under 35 U.S.C. § 119(e) of U.S. Provisional Application No. 62/078,243, filed Nov. 11, 2014, which is incorporated by reference herein in its entirety for all purposes.

SEQUENCE LISTING

The instant application contains a Sequence Listing which has been submitted electronically in ASCII format and is hereby incorporated by reference in its entirety. Said ASCII copy, created on Nov. 9, 2015, is named CD73-200US1 SL.txt and is 128,702 bytes in size.

BACKGROUND OF THE INVENTION

CD73 or ecto-5'nucleotidase (5'-NT) is ubiquitously expressed in a number of tissues.

This protein is anchored to the cell membrane through a glycosylphosphatidylinositol (GPI) linkage, has ecto-enzyme activity, and plays a role in signal transduction. The primary function of CD73 is the conversion of extracellular nucleotides (e.g., 5'-AMP), to which cells are generally impermeable, to their corresponding nucleosides (e.g., adenosine), which can readily enter most cells. CD73 production of adenosine by the dephosphorylation of AMP, has been shown to regulate adenosine receptor engagement in many tissues, indicating that adenosine functions in cytoprotection, cell growth, angiogenesis and immunosuppression, and also plays a role in tumorigenesis.

CD73 expression on tumor cells has been reported in several types of cancer, including bladder cancer, leukemia, glioma, glioblastoma, melanoma, ovarian cancer, thyroid cancer, esophageal cancer, prostate cancer, and breast cancer. Elevated CD73 expression has also been associated with tumor invasiveness, metastasis, and reduced patient survival time. CD73 generates an immunosuppressed environment, characterized by increased adenosine levels, which promote the development and progression of cancer. Notably, CD73 expression has been associated with a prometastatic phenotype in melanoma and breast cancer.

Immune-checkpoint inhibitors hold great potential as cancer therapeutics. Nevertheless, clinical benefits from immune-checkpoint inhibition have been modest. One potential explanation is that tumors use nonoverlapping immunosuppressive mechanisms to facilitate immune escape. Accordingly, improved compositions and methods for reducing tumor-mediated immunosuppression are urgently required.

SUMMARY OF THE INVENTION

The present invention provides isolated binding molecules or antigen-binding fragments thereof which specifically bind to CD73. In some aspects, such CD73-binding molecules are, e.g., antibodies or antigen-binding fragments thereof. In particular embodiments, anti-CD73 antibodies of the invention (e.g., MEDI9447) is useful for reducing tumor-mediated immunosuppression.

In one aspect, the invention generally provides a method of inhibiting tumor growth in a subject, the method comprising administering to a subject in need thereof an anti-CD73 antibody, or an antigen-binding fragment thereof, and an A2A receptor inhibitor.

In another aspect, the invention provides a method of increasing an anti-tumor immune response in a subject, the method comprising administering to a subject in need thereof an anti-CD73 antibody, or an antigen-binding fragment thereof, and an A2A receptor inhibitor to the subject.

In a further aspect, the invention provides a method of treating a tumor in a subject, the method comprising administering to a subject in need thereof an anti-CD73 antibody, or an antigen-binding fragment thereof, and an A2A receptor inhibitor.

In one or more embodiments of any of the aspects of the invention provided the anti-CD73 antibody is MEDI9447 or an antigen-binding fragment thereof. In another embodiment the anti-CD73 antibody is Phen0203 hIgG1 or an antigen-binding fragment thereof. In yet another embodiment the A2A receptor inhibitor is SCH58261. In additional embodiments the CD73 inhibitor is adenosine 5'-($\alpha,\beta$-methylene) diphosphate (APCP). In yet another embodiment the anti-CD73 antibody is MEDI9447 or an antigen-binding fragment thereof and the A2A receptor inhibitor is SCH58261. In additional embodiments the anti-CD73 antibody is Phen0203 hIgG1 or an antigen-binding fragment thereof and the A2A receptor inhibitor is SCH58261. In yet another embodiment the anti-CD73 antibody or antigen-binding fragment thereof or the adenosine receptor inhibitor (A2ARi) are administered concurrently. In further embodiments anti-CD73 antibody is administered prior to the adenosine receptor inhibitor (A2ARi). In other embodiments the adenosine receptor inhibitor (A2ARi) is administered prior to the anti-CD73 antibody. In other embodiments the tumor is a breast cancer, hormonally mediated breast cancer, triple negative breast cancer, colon carcinoma, colorectal cancer, lung cancer, melanoma, non-small cell carcinoma, lymphoma, Hodgkin's and non-Hodgkin's lymphoma, Burkitt's lymphoma, and sarcoma. In another embodiment the method results in an increase in overall survival as compared to the administration of any one of the anti-CD73 antibody or the A2A receptor inhibitor alone. In other embodiments the method induces or increases a tumor-specific immune response. In another embodiment the method reduces the immunosuppressive effects of a AMP/CD73/adenosine pathway. In further embodiments the method reduces metastasis or reduces the propensity of the tumor to metastasize relative to the administration of either the anti-CD73 antibody or the adenosine receptor inhibitor (A2ARi) alone. In yet another embodiment the method reduces the number of metastases within the subject. In certain embodiments the subject is a human patient. In yet another embodiment the tumor is a CD73 overexpressing tumor. In other embodiments the cancer has a prometastatic phenotype.

In another aspect, the invention provides a kit for increasing anti-tumor activity, the kit comprising an anti-CD73 antibody or antigen-binding fragment thereof and an A2A receptor inhibitor. In an embodiment of this aspect, the anti-CD73 antibody is MEDI9447 or an antigen-binding fragment thereof. In another embodiment of this aspect, the anti-CD73 antibody is Phen0203 hIgG1 or an antigen-binding fragment thereof. In yet another embodiment of this aspect, the A2A receptor inhibitor is SCH58261. In another embodiment the anti-CD73 antibody is MEDI9447 or an antigen-binding fragment thereof and the A2A receptor inhibitor is SCH58261. In additional embodiments the anti- CD73 antibody is Phen0203 hIgG1 or an antigen-binding fragment thereof and the A2A receptor inhibitor is SCH58261.

In another aspect, the invention provides a pharmaceutical formulation comprising an effective amount an anti-CD73 antibody or antigen-binding fragment thereof and an A2A receptor inhibitor. In an embodiment of this aspect the anti-CD73 antibody is MEDI9447 or an antigen-binding fragment thereof. In another embodiment the anti-CD73 antibody is Phen0203 hIgG1 or an antigen-binding fragment thereof. In yet another embodiment the A2A receptor inhibitor is SCH58261. In additional embodiments the anti-CD73 antibody is MEDI9447 or an antigen-binding fragment thereof and the A2A receptor inhibitor is SCH58261. In certain embodiments the anti-CD73 antibody is Phen0203 hIgG1 or an antigen-binding fragment thereof and the A2A receptor inhibitor is SCH58261.

BRIEF DESCRIPTION OF THE DRAWINGS/FIGURES

FIG. 1A shows the nucleotide sequence (SEQ ID NO: 22) and amino acid translation (SEQ ID NO: 21) of MEDI9447 VH domain with CDRs shown based on Kabat numbering convention.

Figure 1A:
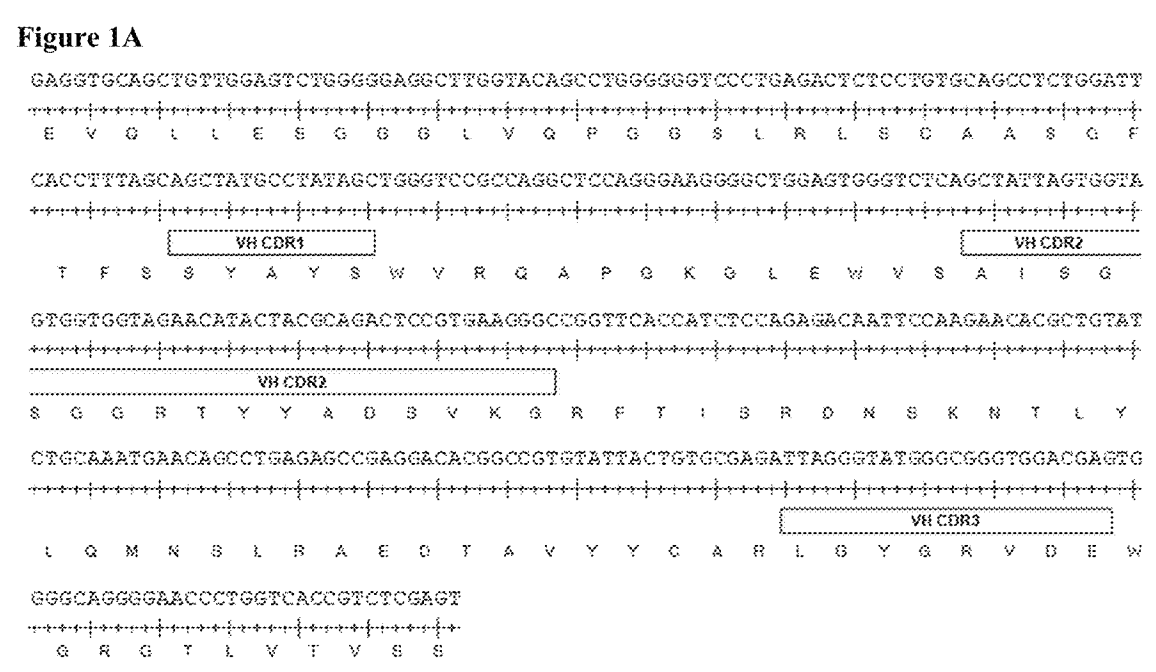
Figure 1B:
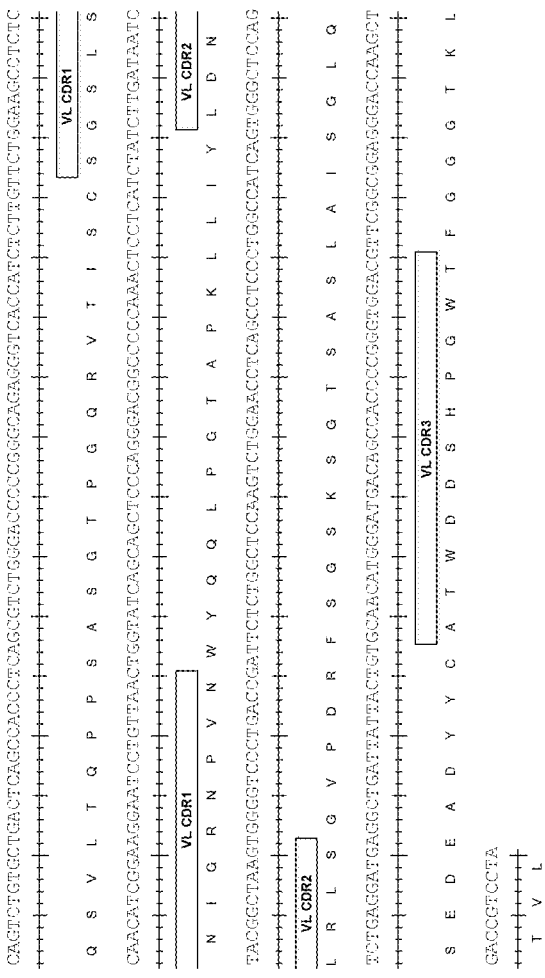
FIG. 1B shows the nucleotide sequence (SEQ ID NO: 24) and amino acid translation (SEQ ID NO: 23) of MEDI9447 VL domain with CDRs shown based on Kabat numbering convention.

FIG. 1C an alignment of MEDI9447 VH (SEQ ID NO: 21) with closest human VH and JH germline sequences (SEQ ID NO: 147). CDRs based on Kabat numbering convention are highlighted and residues different from germline sequences are boxed.

FIG. 1D shows an alignment of MEDI9447 VL (SEQ ID NO: 23) with closest human VL and JL germline sequences (SEQ ID NO: 148). CDRs based on Kabat numbering convention are highlighted and residues different from germline sequences are boxed.

FIG. 2 provides two graph showing antibody-mediated internalization of a cytotoxic FabZAP reagent into MDA-MB-231 cells and 4T1 cells, where the antibodies are MEDI9447 and the control antibody R347.

FIG. 3A is a graph showing inhibition of 5' ectonucleotidase by the anti-CD73 antibody MEDI9447.

FIG. 3B is a graph showing inhibition of AMP hydrolysis by anti-CD73 antibody CD370010.

FIG. 4 is a graph showing that MEDI9447 inhibited tumor growth in a CT26 syngeneic tumor model. Murine CT26 tumor cells were implanted subcutaneously on the right flank of female Balb/C mice. Tumors were allowed to grow for 3 days and treated with MEDI9447 or an isotype control twice weekly for two weeks. At Day 16, tumors were harvested for flow cytometry analysis.

FIG. 5 is a graph showing that MEDI9447 inhibited tumor-infiltrating myeloid-derived suppressor cells (MDSCs). MEDI9447-treated CT26 tumor-bearing mice were sacrificed and tumors were harvested at study Day 16. Tumors were disassociated into single cells, stained for CD45 and MDSC markers, and analyzed by flow cytometry.

FIG. 6 includes six spider plots showing the effect of MEDI9447 mIgG1, anti-PD-1 or the combination on tumor volume. Control antibodies include rIgG2a, which is a Rat IgG2a control monoclonal rat antibody specific for E. coli β-galactosidase (β-Gal), and Isotype control murine IgG1. Tumor volumes from each group of animals were plotted for individual animals out to study day 40. No control group mice were tumor free by the end of the 40 day study period. Anti-CD73 treatment alone resulted in 10% tumor free animals at the end of study. Anti-PD-1 treatment alone also resulted in 10% tumor free animals at the end of study. Remarkably, the combination of anti-CD73 and anti-PD treatment resulted in 60% tumor free mice. None of the control group mice were tumor free by the end of the study.

FIG. 7 is a graph showing the effect of MEDI9447 mIgG1, anti-PD-1 or the combination on tumor volume.

Figure 8:
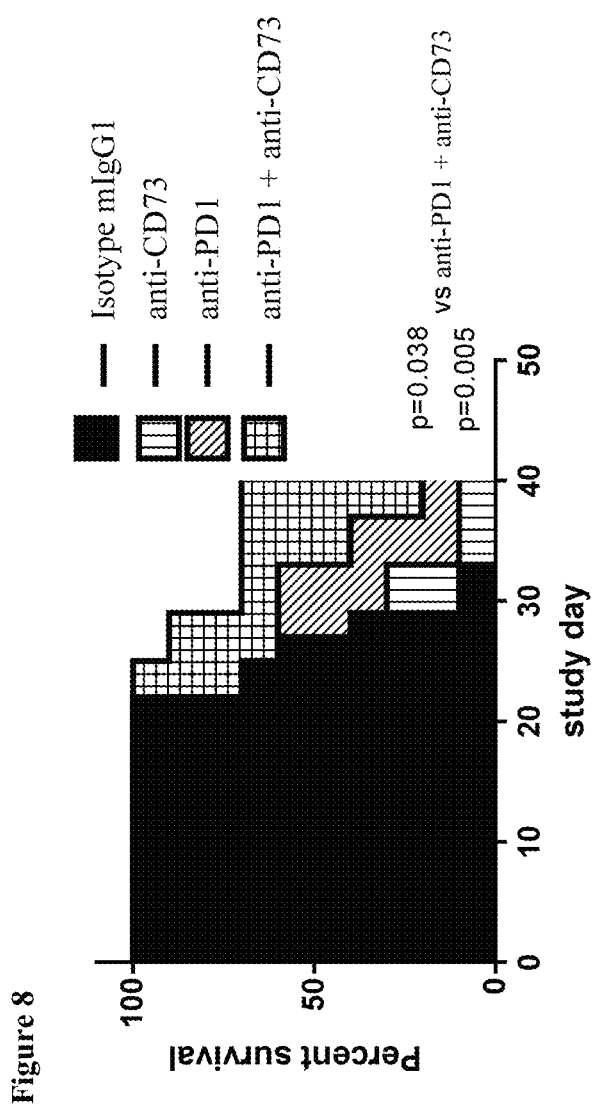

FIG. 8 is a graph showing the effect of MEDI9447 mIgG1, anti-PD-1 or the combination on survival.

FIG. 9 is a graph showing the effect of Phen0203 hIgG1 antibody on AMP-mediated suppression of CD4+CD25− T-cell proliferation.

FIG. 10 is a graph showing the effect of SCH58261 on AMP-mediated suppression of $CD4^+CD25^-$ T cell proliferation.

Figure 11:
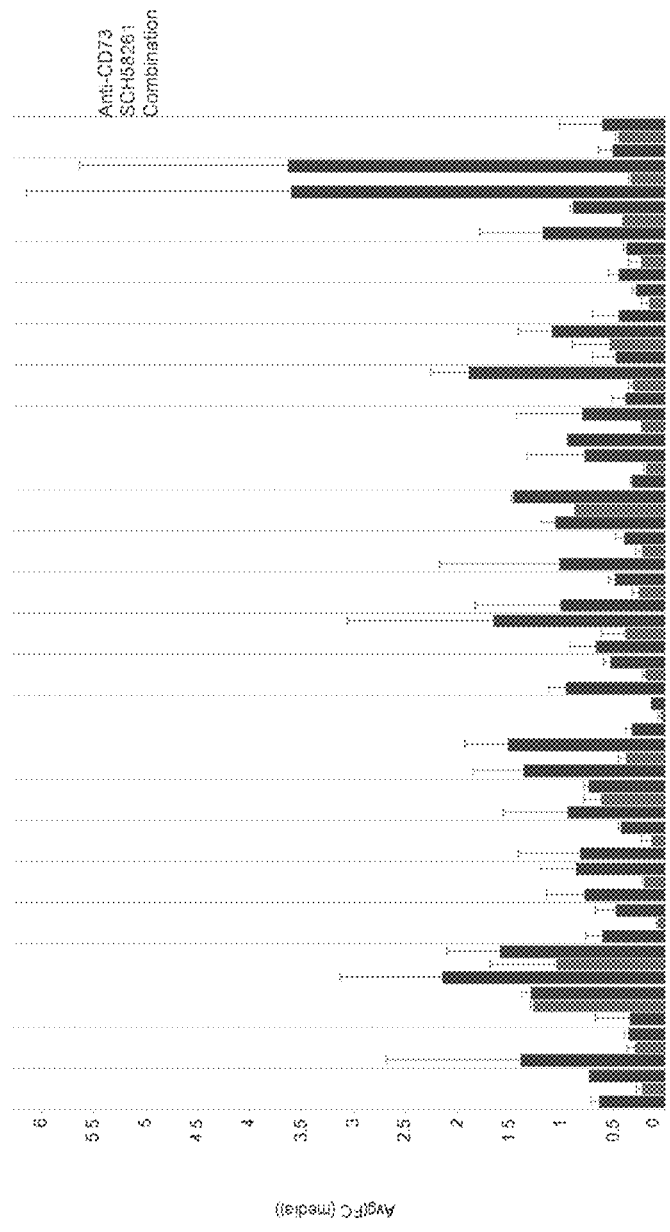

FIG. 11 is a graph showing the effect of anti-CD73 and SH58261, either alone or in combination, on IFNγ supernatant levels in a mixed leukocyte reaction.

Figure 12:
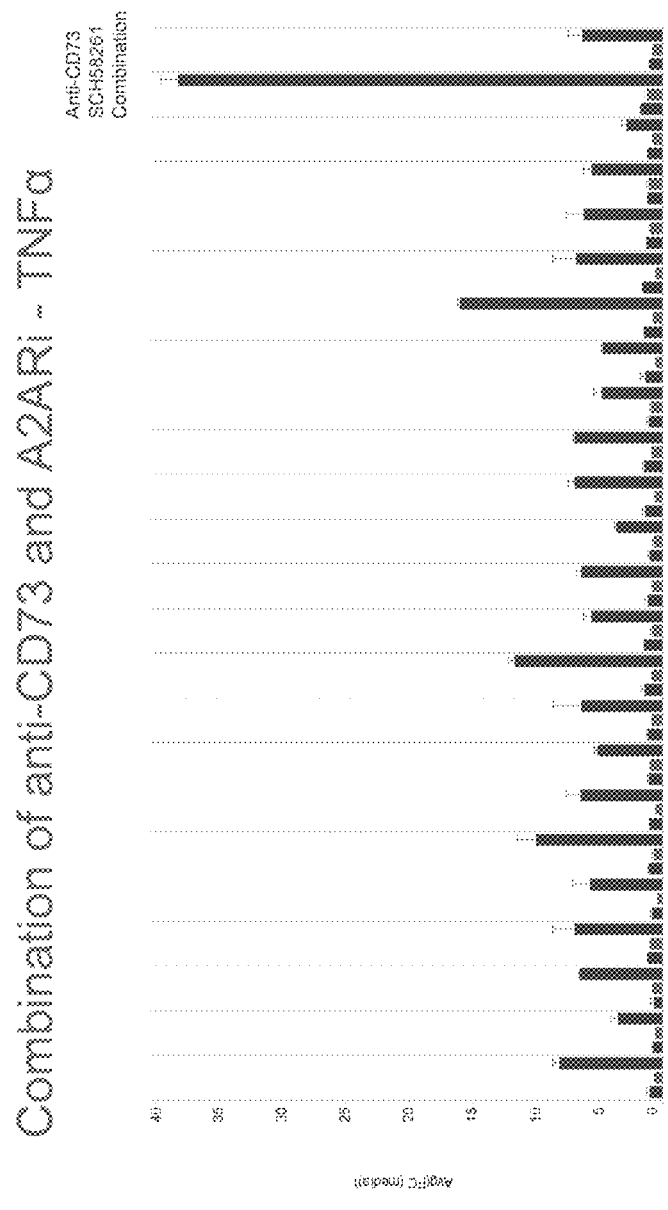

FIG. 12 is a graph showing the effect of anti-CD73 and SH58261, either alone or in combination, on TNFα supernatant levels in a mixed leukocyte reaction.

DETAILED DESCRIPTION OF THE INVENTION

The present invention provides isolated binding molecules or antigen-binding fragments thereof which specifically bind to CD73. In some aspects, such molecules are antibodies and antigen-binding fragments thereof that specifically bind to CD73. Related polynucleotides, vectors, pharmaceutical compositions comprising the anti-CD73 antibodies or antigen-binding fragments thereof, are also provided. Also provided are methods of making as well as methods of using the anti-CD73 antibodies and antigen-binding fragments disclosed herein, for example, diagnostic methods and methods of treating cancer in a subject (as direct therapy, adjuvant therapy, or in combination therapy). The invention also provides antibody-drug conjugates derived from the CD73 binding molecules disclosed herein.

In order that the present disclosure can be more readily understood, certain terms are first defined. Additional definitions are set forth throughout the detailed description.

I. Definitions

Before describing the present invention in detail, it is to be understood that this invention is not limited to specific compositions or process steps, as such can vary. As used in this specification and the appended claims, the singular forms "a", "an" and "the" include plural referents unless the context clearly dictates otherwise. The terms "a" (or "an"), as well as the terms "one or more," and "at least one" can be used interchangeably herein.

Furthermore, "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Unless otherwise indicated, amino acid sequences are written left to right in amino to carboxy orientation. The headings provided herein are not limitations of the various aspects, which can be had by reference to the specification as a whole. Accordingly, the terms defined immediately below are more fully defined by reference to the specification in its entirety.

It is understood that wherever aspects are described herein with the language "comprising," otherwise analogous aspects described in terms of "consisting of" and/or "consisting essentially of" are also provided.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter codes.

The term "CD73 polypeptide" as used herein refers to the CD73 (Cluster of Differentiation 73) protein, also referred to as 5'-nucleotidase (5'-NT) or ecto-5'-nucleotidase in the literature, which is encoded by the NT5E gene. See, e.g., Misumi et al. Eur. J. Biochem. 191(3): 563-9 (1990). The respective sequences of the human and murine forms of CD73 are available at the Uniprot database under accession numbers P21589 and Q61503, respectively.

An exemplary CD73 polypeptide is provided below:

```
>sp|P21589|5NTD_HUMAN 5'-nucleotidase OS = Homo
sapiens GN = NT5E PE = 1 SV = 1
                                   (SEQ ID NO: 130)
MCPRAARAPATLLLALGAVLWPAAGAWELTILHTNDVHSRLEQTSEDSSK

CVNASRCMGGVARLFTKVQQIRRAEPNVLLLDAGDQYQGTIWFIVYKGAE

VAHFMNALRYDAMALGNHEFDNGVEGLIEPLLKEAKFPILSANIKAKGPL

ASQISGLYLPYKVLPVGDEVVGIVGYTSKETPFLSNPGTNLVFEDEITAL

QPEVDKLKTLNVNKIIALGHSGFEMDKLIAQKVRGVDVVVGGHSNTFLYT

GNPPSKEVPAGKYPFIVTSDDGRKVPVVQAYAFGKYLGYLKIEFDERGNV

ISSHGNPILLNSSIPEDPSIKADINKWRIKLDNYSTQELGKTIVYLDGSS

QSCRFRECNMGNLICDAMINNNLRHTDEMFWNHVSMCILNGGGIRSPIDE

RNNGTITWENLAAVLPFGGTFDLVQLKGSTLKKAFEHSVHRYGQSTGEFL

QVGGIHVVYDLSRKPGDRVVKLDVLCTKCRVPSYDPLKMDEVYKVILPNF

LANGGDGFQMIKDELLRHDSGDQDINVVSTYISKMKVIYPAVEGRIKFST

GSHCHGSFSLIFLSLWAVIFVLYQ
```

Soluble and membrane-bound forms of CD73 have been identified. See Klemens et al, Biochem. Biophys. Res. Commun. 172(3):1371-7 (1990). In addition, several different isoenzymes have been identified. See Rosi et al. Life Sci. 62(25):2257-66 (1998). The full-length CD73 protein comprises 574 amino acids. The mature CD73 protein is produced after removal of a signal sequence (positions 1 to 26) and the C-terminal region of the propeptide (positions 550-574). In addition, amino acids 404 to 453 are removed in isoform 2 of CD73 after alternative splicing. Natural variants are also known, for example, variant C358Y, variant T376A, and variant M379T. See Misumi et al., Eur. J. Biochem. 191:563-569 (1990); Otsuki et al. DNA Res. 12:117-126 (2005); Mungall et al. Nature 425:805-811 (2003); Hansen et al. Gene 167:307-312 (1995); Klemens et al. Biochem. Biophys. Res. Commun. 172:1371-1377 (1990); Knapp et al. Structure 20:2161-2173 (2012); or St. Hilaire et al. N. Engl. J. Med. 364:432-442 (2011), all of which are herein incorporated by reference in their entireties.

Accordingly, the CD73-binding molecules disclosed herein can be used for example to treat or diagnose cancer (e.g., breast cancer (including hormonally mediated breast cancer, see, e.g., Innes et al. (2006) Br. J. Cancer 94:1057-1065), triple negative breast cancer, colon carcinoma, colorectal cancer, lung cancer, melanoma, non-small cell carcinoma, lymphoma, Hodgkin's and non-Hodgkin's lymphoma, Burkitt's lymphoma, and sarcoma). In addition, the measurement of the levels of CD73 in a sample from a patient (e.g., a tissue fluid) using the CD73-binding molecules disclosed herein can be used for monitoring the development of the above described diseases, for assessing the efficacy of therapies, to elect patients for treatment with a particular therapy, or to take medical decisions, for example, commencing, ending, interrupting, or modifying a certain treatment.

The term "adenosine A2A receptor (ADORA2A) polypeptide" as used herein refers to a protein having at least about 85% amino acid sequence identity to NP 000666 or a fragment thereof and having adenosine binding and G-protein signaling activity. The respective sequences of the human and murine forms of adenosine A2A receptor are available at the Uniprot database under accession numbers P29274 and Q60613, respectively.

An exemplary adenosine A2A receptor polypeptide is provided below:

```
>sp|P29274|AA2AR_HUMAN Adenosine receptor A2a
OS = Homo sapiens GN = ADORA2A PE = 1 SV = 2
                                   (SEQ ID NO: 131)
MPIMGSSVYITVELAIAVLAILGNVLVCWAVWLNSNLQNVTNYFVVSLAA

ADIAVGVLAIPFAITITGFCAACHGCLFIACFVLVLTQSSIFSLLAIAID

RYIAIRIPLRYNGLVTGTRAKGIIAICWVLSFAIGLTPMLGWNNCGQPKE

GKNHSQGCGEGQVACLFEDVVPMNYMVYFNFFACVLVPLLLMLGVYLRIF

LAARRQLKQMESQPLPGERARSTLQKEVHAAKSLAIIVGLFALCWLPLHI

INCFTFFCPDCSHAPLWLMYLAIVLSHTNSVVNPFIYAYRIREFRQTFRK

IIRSHVLRQQEPFKAAGTSARVLAAHGSDGEQVSLRLNGHPPGVWANGSA

PHPERRPNGYALGLVSGGSAQESQGNTGLPDVELLSHELKGVCPEPPGLD

DPLAQDGAGVS
```

By "SCH58261" is meant a small compound having the following structural formula:

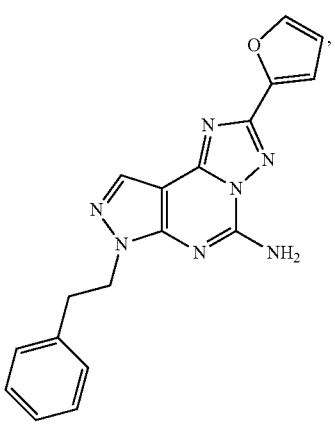 [SMILES: Nc1nc2c(cnn2CCc2ccccc2)c2nc(-c3ccco3)nn12]

CAS 160098-96-4, and having adenosine A2A receptor binding and inhibitory activity.

By "adenosine A2A receptor inhibitor (A2ARi)" is meant an agent that inhibits the G protein signaling activity of an adenosine A2A receptor. In one embodiment, inhibition of A2A receptor activity is measured by measuring TNFα secretion in a mixed lymphocyte stimulation assay, where an increase in TNFα indicates inhibition of adenosine A2A receptor activity.

By "adenosine 5'-(α,β-methylene)diphosphate (APCP)" is meant a small compound having the following structural formula:

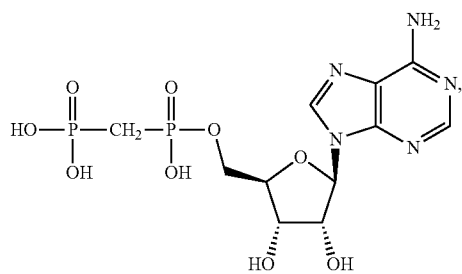 [SMILES: Nc1ncnc2c1ncn2[C@@H]1O[C@H](COP(=O)(O)CP(=O)(O)O)[C@@H](O)[C@H]1O]

CAS 3768-14-7, and having CD73 enzyme inhibitory activity.

The terms "inhibit," "block," "suppress," and grammatical variants thereof are used interchangeably herein and refer to any statistically significant decrease in biological activity, including full blocking of the activity. For example, "inhibition" can refer to a decrease of about 10%, 20%, 30%, 40%, 50%, 60%, 70%, 80%, 90% or 100% in biological activity. Accordingly, when the terms "inhibition" or "suppression" are applied to describe, e.g., an effect on the enzymatic activity of CD73, the term refers to the ability of an anti-CD73 antibody or antigen-binding fragment thereof to statistically significantly decrease the 5'-nucleotidase activity of CD73 (catabolizing the hydrolysis of adenosine monophosphate, AMP, to adenosine), relative to the CD73-mediated 5'-nucleotidase activity in an untreated (control) cell. The cell which expresses CD73 can be a naturally occurring cell or cell line (e.g., a cancer cell) or can be recombinantly produced by introducing a nucleic acid encoding CD73 into a host cell. In some aspects, an anti-CD73 antibody or antigen-binding fragment thereof can statistically significantly decrease the 5'-nucleotidase activity of a soluble form of CD73 in a biological fluid. In one aspect, the anti-CD73 binding molecule, e.g., an antibody or antigen-binding fragment thereof inhibits CD73-mediated 5'-nucleotidase activity by at least 10%, at least 15%, or at least 20%, at least 25%, at least 30%, at least 35%, or at least 40%, at least 45%, or at least 50%, at least 55%, or at least 60%, at least 65%, or at least 70%, at least 75%, or at least 80%, at least 85%, or at least 90%, at least 95%, or about 100%, as determined, for example, by the methods described in the Examples infra, and/or methods known in the art.

The term "suppress CD73 activity," as used herein, refer to the ability of anti-CD73 binding molecule, e.g., an antibody or antigen-binding fragment thereof to statistically significantly decrease CD73-dependent 5'-nucleotidase activity in a cell expressing CD73 or a sample containing CD73. In some aspects, the suppression of CD73 activity can be a decrease of at least 10%, or at least 15%, or at least 20%, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or about 100% when cells or a sample are contacted with an anti-CD73 binding molecule, e.g., an antibody or antigen-binding fragment thereof of the present disclosure, relative to the CD73 activity measured in the absence of the anti-CD73 binding molecule, e.g., an antibody or antigen-binding fragment thereof (control conditions).

The terms "antibody" or "immunoglobulin," as used interchangeably herein, include whole antibodies and any antigen-binding fragment or single chains thereof.

A typical antibody comprises at least two heavy (H) chains and two light (L) chains interconnected by disulfide bonds. Each heavy chain is comprised of a heavy chain variable region (abbreviated herein as VH or VH) and a heavy chain constant region. The heavy chain constant region is comprised of three domains, CH1, CH2, and CH3. Each light chain is comprised of a light chain variable region (abbreviated herein as VL or VL) and a light chain constant region. The light chain constant region is comprised of one domain, CL. The VH and VL regions can be further subdivided into regions of hypervariability, termed Complementarity Determining Regions (CDR), interspersed with regions that are more conserved, termed framework regions (FW). Each VH and VL is composed of three CDRs and four FWs, arranged from amino-terminus to carboxy-terminus in the following order: FW1, CDR1, FW2, CDR2, FW3, CDR3, FW4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system. Exemplary antibodies of the present disclosure include anti-CD73 antibodies (original and germlined), affinity optimized clones, optimized antibodies lacking ADCC, conjugated antibodies (e.g., ADC), and other optimized antibodies (e.g., serum half-life-optimized antibodies including, for example, YTE mutations, see Dall'Acqua et al., J. Biol. Chem. 281:23514-24 (2006) and U.S. Pat. No. 7,083,784, which are hereby incorporated by reference in their entireties).

The term "germlining" means that amino acids at specific positions in an antibody are mutated back to those in the germ line.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity.

An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc. to form ADCs.

A "blocking" antibody or an "antagonist" antibody is one which inhibits or reduces biological activity of the antigen it binds, such as CD73. In a certain aspect blocking antibodies or antagonist antibodies substantially or completely inhibit the biological activity of the antigen. Desirably, the biological activity is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or even 100%.

The terms "CD73 antibody," "antibody that binds to CD73" or "anti-CD73" refers to an antibody or antigen-binding fragment thereof that is capable of selectively binding CD73. In one embodiment an anti-CD73 antibody binds CD73 with sufficient affinity such that the molecule is useful as a therapeutic agent or diagnostic reagent in targeting CD73. The extent of binding of an anti-CD73 antibody to an unrelated, non-CD73 protein is less than about 10% of the binding of the antibody to CD73 as measured, e.g., by a radioimmunoassay (MA), BIACORE™ (using recombinant CD73 as the analyte and antibody as the ligand, or vice versa), or other binding assays known in the art. In certain aspects, an antibody that binds to CD73 has a dissociation constant ($K_D$) of ≤1 μM, ≤100 nM, ≤10 nM, ≤1 nM, ≤0.1 nM, ≤10 pM, ≤1 pM, or ≤0.1 pM. The term "anti-CD73" also broadly encompasses molecules comprising, e.g., the CDRs of the antibodies disclosed herein incorporated into a scaffold. Thus, the phrase "isolated binding molecule or antigen-binding fragment thereof which specifically binds to CD73" would refer not only to antibodies and antigen-binding fragments thereof, but also would refer to a molecule comprising, for example, one or more scaffolds (such as a fibronectin III domain from fibronectin or tenascin-3) incorporating the CDRs of the antibodies disclosed herein.

In one embodiment, an anti-CD73 antibody refers to an antibody in IgG1-TM format such that the IgG1 Fc domain comprises mutations L234, L235E and P331, binds soluble and cell-surface displayed CD73, and inhibits CD73 enzymatic activity. FIGS. 1A-D provide the nucleotide and amino acid sequences of MEDI9447 VH and VL domains.

The term "antigen-binding fragment" refers to a molecule comprising a portion of an intact antibody, and in particular refers to a molecule comprising the antigenic determining variable regions of an intact antibody. It is known in the art that the antigen-binding function of an antibody can be performed by fragments of a full-length antibody. Examples of antibody fragments include, but are not limited to Fab, Fab', F(ab')2, and Fv fragments, linear antibodies, single chain antibodies, and multispecific antibodies formed from antibody fragments.

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants.

The term "monoclonal antibody" encompasses both intact and full-length monoclonal antibodies as well as antibody fragments (such as Fab, Fab', F(ab')2, Fv), single chain variable fragments (scFv), fusion proteins comprising an antibody portion, and any other modified immunoglobulin molecule comprising an antigen recognition site. Furthermore, "monoclonal antibody" refers to such antibodies made in any number of ways including, but not limited to, by hybridoma, phage selection, recombinant expression, and transgenic animals (e.g., expression of a human antibody in a transgenic mouse).

The term "humanized antibody" refers to an antibody derived from a non-human (e.g., murine) immunoglobulin, which has been engineered to contain minimal non-human (e.g., murine) sequences. Typically, humanized antibodies are human immunoglobulins in which residues from the CDRs are replaced by residues from the CDR of a non-human species (e.g., mouse, rat, rabbit, or hamster) that have the desired specificity, affinity, and capability (Jones et al., 1986, *Nature*, 321:522-525; Riechmann et al., 1988, *Nature*, 332:323-327; Verhoeyen et al., 1988, *Science*, 239:1534-1536). In some instances, the framework (FW) amino acid residues of a human immunoglobulin are replaced with the corresponding residues in an antibody from a non-human species that has the desired specificity, and/or affinity, and/or capability.

The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin, whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. No. 5,225,539 or 5,639,641.

A "variable region" of an antibody refers to the variable region of the antibody light chain or the variable region of the antibody heavy chain, either alone or in combination. The variable regions of the heavy and light chain each consist of four FW regions connected by three CDR regions. The CDRs in each chain are held together in close proximity by the FW regions and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al. (1997) J. Molec. Biol. 273:927-948)). In addition, combinations of these two approaches are sometimes used in the art to determine CDRs.

The Kabat numbering system is generally used when referring to a residue in the variable domain (approximately residues 1-107 of the light chain and residues 1-113 of the heavy chain) (e.g., Kabat et al., Sequences of Immunological Interest, 5th Ed. Public Health Service, National Institutes of Health, Bethesda, Md. (1991)).

The phrases "amino acid position numbering as in Kabat," "Kabat position," and grammatical variants thereof refer to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FW or CDR of the variable domain. For example, a heavy chain variable domain can include a single amino acid insert (residue 52a according to Kabat) after residue 52 of H2 and inserted residues (e.g., residues 82a, 82b, and 82c, etc. according to Kabat) after heavy chain FW residue 82.

TABLE 1

| Loop | Kabat | AbM | Chothia |
|---|---|---|---|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 ... 34 |
| | | (Kabat Numbering) | |
| H1 | H31-H35 | H26-H35 | H26-H32 |
| | | (Chothia Numbering) | |
| H2 | H50-H65 | H50-H58 | H52-H56 |
| H3 | H95-H102 | H95-H102 | H95-H102 |

The Kabat numbering of residues can be determined for a given antibody by alignment at regions of homology of the sequence of the antibody with a "standard" Kabat numbered sequence. Chothia refers instead to the location of the structural loops (Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

IMGT (ImMunoGeneTics) also provides a numbering system for the immunoglobulin variable regions, including the CDRs. See e.g., Lefranc, M. P. et al., Dev. Comp. Immunol. 27: 55-77(2003), which is herein incorporated by reference. The IMGT numbering system was based on an alignment of more than 5,000 sequences, structural data, and characterization of hypervariable loops and allows for easy comparison of the variable and CDR regions for all species. According to the IMGT numbering schema VH-CDR1 is at positions 26 to 35, VH-CDR2 is at positions 51 to 57, VH-CDR3 is at positions 93 to 102, VL-CDR1 is at positions 27 to 32, VL-CDR2 is at positions 50 to 52, and VL-CDR3 is at positions 89 to 97.

The EU index or EU numbering system is based on the sequential numbering of the first human IgG sequenced (the EU antibody). Because the most common reference for this convention is the Kabat sequence manual (Kabat et al., 1991), the EU index is sometimes erroneously used synonymously with the Kabat index. The EU index does not provide insertions and deletions, and thus in some cases comparisons of IgG positions across IgG subclass and species can be unclear, particularly in the hinge regions. Nonetheless, the convention has sufficed at enabling straightforward comparison between Fc regions in numerous Fc structure function studies. Accordingly, the numbering scheme used for substitutions and insertions in Fc regions in this specification is the EU index as in Kabat. In contrast, the numbering scheme used for the variable regions (VH and VL) in this specification is the regular Kabat numbering.

As used throughout the specification the VH CDRs sequences described correspond to the classical Kabat numbering locations, namely Kabat VH-CDR1 is at positions 31-35, VH-CDR2 is a positions 50-65, and VH-CDR3 is at positions 95-102. VL-CDR1, VL-CDR2 and VL-CDR3 also correspond to classical Kabat numbering locations, namely positions 24-34, 50-56 and 89-97, respectively.

As used herein the Fc region includes the polypeptides comprising the constant region of an antibody excluding the first constant region immunoglobulin domain. Thus, Fc refers to the last two constant region immunoglobulin domains of IgA, IgD, and IgG, and the last three constant region immunoglobulin domains of IgE and IgM, and the flexible hinge N-terminal to these domains. For IgA and IgM Fc can include the J chain. For IgG, Fc comprises immunoglobulin domains Cgamma2 and Cgamma3 (Cy2 and Cy3) and the hinge between Cgamma1 (Cy1) and Cgamma2 (Cy2).

Although the boundaries of the Fc region can vary, the human IgG heavy chain Fc region is usually defined to comprise residues C226 or P230 to its carboxyl-terminus, wherein the numbering is according to the EU index as set forth in Kabat (Kabat et al., Sequences of Proteins of Immunological Interest, 5th Ed. Public Health Service, National Institutes of Health, Bethesda, Md. (1991)). Fc can refer to this region in isolation, or this region in the context of an antibody, antibody fragment, or Fc fusion protein. Polymorphisms have been observed at a number of different Fc positions, including but not limited to positions 270, 272, 312, 315, 356, and 358 as numbered by the EU index, and thus slight differences between the presented sequence and sequences in the prior art can exist.

The term "human antibody" means an antibody produced by a human or an antibody having an amino acid sequence corresponding to an antibody produced by a human made using any technique known in the art (e.g., recombinant expression in cultures cells, or expression in transgenic animals). Thus, the term human antibody also encompasses an antibody having an amino acid sequence corresponding to an antibody originally produced by a human (or an engineered variant or derivative thereof) but expressed in a non-human system (e.g., produced by chemical synthesis; recombinantly expressed in microbial, mammal, or insect cells; or expressed in an animal subject). Accordingly, an antibody obtained from a human subject or from human cells (e.g., hybridoma or cell line expressing a recombinant antibody or fragment thereof) and subsequently expressed in an animal, e.g., mice, is considered a human antibody. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "chimeric antibodies" refers to antibodies wherein the amino acid sequence of the immunoglobulin molecule is derived from two or more animal species. Typically, the variable region of both light and heavy chains corresponds to the variable region of antibodies derived from one species of mammals (e.g., mouse, rat, rabbit, etc.) with the desired specificity, and/or affinity, and/or capability while the constant regions are homologous to the sequences in antibodies derived from another specie (usually human) to avoid eliciting an immune response in that species.

The term "epitope" as used herein refers to an antigenic protein determinant capable of binding to a CD73 antibody or CD73 binding molecule disclosed herein. Epitopes usually consist of chemically active surface groupings of molecules such as amino acids or sugar side chains and usually have specific three dimensional structural characteristics, as well as specific charge characteristics. The part of an antibody or binding molecule that recognizes the epitope is called a paratope. The epitopes of protein antigens are divided into two categories, conformational epitopes and linear epitopes, based on their structure and interaction with the paratope. A conformational epitope is composed of discontinuous sections of the antigen's amino acid sequence. These epitopes interact with the paratope based on the 3-D surface features and shape or tertiary structure of the antigen. By contrast, linear epitopes interact with the paratope based on their primary structure. A linear epitope is formed by a continuous sequence of amino acids from the antigen.

The term "antibody binding site" refers to a region in the antigen (e.g., CD73) comprising a continuous or discontinuous site (i.e., an epitope) to which a complementary antibody specifically binds. Thus, the antibody binding site can contain additional areas in the antigen which are beyond the epitope and which can determine properties such as binding affinity and/or stability, or affect properties such as antigen enzymatic activity or dimerization. Accordingly, even if two antibodies bind to the same epitope within an antigen, if the antibody molecules establish distinct intermolecular contacts with amino acids outside of the epitope, such antibodies are considered to bind to distinct antibody binding sites.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure.

"Potency" is normally expressed as an $IC_{50}$ value, in nM unless otherwise stated. $IC_{50}$ is the median inhibitory concentration of an antigen-binding molecule. In functional assays, $IC_{50}$ is the concentration that reduces a biological response by 50% of its maximum. In ligand-binding studies, $IC_{50}$ is the concentration that reduces receptor binding by 50% of maximal specific binding level. $IC_{50}$ can be calculated by any number of means known in the art. Improvement in potency can be determined by measuring, e.g., against a parent antibody (for example, the parent antibody prior to germlining or the parent antibody prior to affinity optimization).

The fold improvement in potency for the antibodies or polypeptides of the present disclosure as compared to a parent antibody can be at least about 2-fold, at least about 4-fold, at least about 6-fold, at least about 8-fold, at least about 10-fold, at least about 15-fold, at least about 20-fold, at least about 25-fold, at least about 30-fold, at least about 40-fold, at least about 50-fold, at least about 60-fold, at least about 70-fold, at least about 80-fold, at least about 90-fold, at least about 100-fold, at least about 110-fold, at least about 120-fold, at least about 130-fold, at least about 140-fold, at least about 150-fold, at least about 160-fold, at least about 170-fold, or at least about 180-fold or more.

"Antibody-dependent cell-mediated cytotoxicity" or "ADCC" refers to a form of cytotoxicity in which secreted immunoglobulins bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. Specific high-affinity IgG antibodies directed to the surface of target cells "arm" the cytotoxic cells and are absolutely required for such killing. Lysis of the target cell is extracellular, requires direct cell-to-cell contact, and does not involve complement. It is contemplated that, in addition to antibodies, other proteins comprising Fc regions, specifically Fc fusion proteins, having the capacity to bind specifically to an antigen-bearing target cell will be able to effect cell-mediated cytotoxicity. For simplicity, the cell-mediated cytotoxicity resulting from the activity of an Fc fusion protein is also referred to herein as ADCC activity.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cells or compositions include those which have been purified to a degree that they are no longer in a form in which they are found in nature. In some aspects, an antibody, polynucleotide, vector, cell, or composition which is isolated is substantially pure.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

The term "pharmaceutical composition" refers to a preparation which is in such form as to permit the biological activity of the active ingredient (e.g., an anti-CD73 binding molecule disclosed herein) to be effective, and which contains no additional components which are unacceptably toxic to a subject to which the composition would be administered. Such composition can be sterile.

An "effective amount" of an anti-CD73 binding molecule as disclosed herein is an amount sufficient to carry out a specifically stated purpose. An "effective amount" can be determined empirically and in a routine manner, in relation to the stated purpose.

The term "therapeutically effective amount" refers to an amount of an anti-CD73 binding molecule disclosed herein or other drug effective to "treat" a disease or disorder in a subject or mammal.

The word "label" when used herein refers to a detectable compound or composition which is fused (e.g., genetically fused) or conjugated (e.g., chemically conjugated) directly or indirectly to an anti-CD73 binding molecule disclosed herein so as to generate a "labeled" anti-CD73 binding molecule. The label can be detectable by itself (e.g., radioisotope labels or fluorescent labels) or, in the case of an enzymatic label, can catalyze chemical alteration of a substrate compound or composition which is detectable.

Terms such as "derivatizable group" and "derivatizable functional group" are used interchangeably and refer to a functional group that is capable of reacting to permit the formation of a covalent bond between an anti-CD73 binding molecule disclosed herein (e.g., a CD73 antibody) and another substance. In some aspects, such substance is a therapeutic agent (e.g., a cytotoxin), a detectable label, a polymer (e.g., PEG), etc. Exemplary derivatizable groups include thiol, hydroxyl, amino, carboxy, and amide, as well as modified forms thereof, such as activated or protected forms.

Terms such as "treating" or "treatment" or "to treat" or "alleviating" or "to alleviate" refer to both (1) therapeutic measures that cure, slow down, lessen symptoms of, and/or halt progression of a diagnosed pathologic condition or disorder and (2) prophylactic or preventative measures that prevent and/or slow the development of a targeted pathologic condition or disorder. Thus, those in need of treatment include those already with the disorder; those prone to have the disorder; and those in whom the disorder is to be prevented. In certain aspects, a subject is successfully "treated" for cancer according to the methods of the present disclosure if the patient shows, e.g., total, partial, or transient remission of a certain type of cancer.

The terms "cancer", "tumor", "cancerous", and "malignant" refer to or describe the physiological condition in mammals that is typically characterized by unregulated cell growth. Examples of cancers include but are not limited to, lymphomas, non-small cell lung cancer, Hodgkin's and non-Hodgkin's lymphoma, breast cancer (including hormonally mediated breast cancer, see, e.g., Innes et al. (2006) Br. J. Cancer 94:1057-1065), colon cancer, In some aspects, the term cancer as used herein specifically refers to cancer expressing CD73 (e.g., colon cancer, breast cancer, lymphoma, non-small cell carcinoma).

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide can comprise modified nucleotides, such as methylated nucleotides and their analogs. The preceding description applies to all polynucleotides referred to herein, including RNA and DNA.

The term "vector" means a construct, which is capable of delivering, and in some aspects, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of the instant disclosure are based upon antibodies, in certain aspects, the polypeptides can occur as single chains or associated chains.

A "recombinant" polypeptide or protein refers to a polypeptide or protein produced via recombinant DNA technology. Recombinantly produced polypeptides and proteins expressed in engineered host cells are considered isolated, as are native or recombinant polypeptides which have been separated, fractionated, or partially or substantially purified by any suitable technique. The polypeptides disclosed herein can be recombinantly produced using methods known in the art. Alternatively, the proteins and peptides disclosed herein can be chemically synthesized.

The term "amino acid substitution" refers to replacing an amino acid residue present in a parent sequence with another amino acid residue. An amino acid can be substituted in a parent sequence, for example, via chemical peptide synthesis or through recombinant methods known in the art. Accordingly, references to a "substitution at position X" or "substitution at position X" refer to the substitution of an amino acid present at position X with an alternative amino acid residue. In some aspects, substitution patterns can described according to the schema AXY, wherein A is the single letter code corresponding to the amino acid naturally present at position X, and Y is the substituting amino acid residue. In other aspects, substitution patterns can described according to the schema XY, wherein Y is the single letter code corresponding to the amino acid residue substituting the amino acid naturally present at position X.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, if an amino acid in a polypeptide is replaced with another amino acid from the same side chain family, the substitution is considered to be conservative. In another aspect, a string of amino acids can be conservatively replaced with a structurally similar string that differs in order and/or composition of side chain family members.

Non-conservative substitutions include those in which (i) a residue having an electropositive side chain (e.g., Arg, His or Lys) is substituted for, or by, an electronegative residue (e.g., Glu or Asp), (ii) a hydrophilic residue (e.g., Ser or Thr) is substituted for, or by, a hydrophobic residue (e.g., Ala, Leu, Ile, Phe or Val), (iii) a cysteine or proline is substituted for, or by, any other residue, or (iv) a residue having a bulky hydrophobic or aromatic side chain (e.g., Val, His, Ile or Trp) is substituted for, or by, one having a smaller side chain (e.g., Ala, Ser) or no side chain (e.g., Gly).

Other substitutions can be readily identified by workers of ordinary skill. For example, for the amino acid alanine, a substitution can be taken from any one of D-alanine, glycine, beta-alanine, L-cysteine and D-cysteine. For lysine, a replacement can be any one of D-lysine, arginine, D-arginine, homo-arginine, methionine, D-methionine, ornithine, or D-ornithine. Generally, substitutions in functionally important regions that can be expected to induce changes in the properties of isolated polypeptides are those in which (i) a polar residue, e.g., serine or threonine, is substituted for (or by) a hydrophobic residue, e.g., leucine, isoleucine, phenylalanine, or alanine; (ii) a cysteine residue is substituted for (or by) any other residue; (iii) a residue having an electropositive side chain, e.g., lysine, arginine or histidine, is substituted for (or by) a residue having an electronegative side chain, e.g., glutamic acid or aspartic acid; or (iv) a residue having a bulky side chain, e.g., phenylalanine, is substituted for (or by) one not having such a side chain, e.g., glycine. The likelihood that one of the foregoing non-conservative substitutions can alter functional properties of the protein is also correlated to the position of the substitution with respect to functionally important regions of the protein: some non-conservative substitutions can accordingly have little or no effect on biological properties.

The term "amino acid insertion" refers to introducing a new amino acid residue between two amino acid residues present in the parent sequence. An amino acid can be inserted in a parent sequence, for example, via chemical peptide synthesis or through recombinant methods known in the art. Accordingly as used herein, the phrases "insertion between positions X and Y" or "insertion between Kabat positions X and Y," wherein X and Y correspond to amino acid positions (e.g., a cysteine amino acid insertion between positions 239 and 240), refers to the insertion of an amino acid between the X and Y positions, and also to the insertion in a nucleic acid sequence of a codon encoding an amino acid between the codons encoding the amino acids at positions X and Y. Insertion patterns can be described according to the schema AXins, wherein A is the single letter code corresponding to the amino acid being inserted, and X is the position preceding the insertion.

The term "percent sequence identity" between two polypeptide or polynucleotide sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence.

The percentage of sequence identity is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences can be accomplished using readily available software both for online use and for download. Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

In certain aspects, the percentage identity "X" of a first amino acid sequence to a second sequence amino acid is calculated as $100 \times (Y/Z)$, where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

One skilled in the art will appreciate that the generation of a sequence alignment for the calculation of a percent sequence identity is not limited to binary sequence-sequence comparisons exclusively driven by primary sequence data. Sequence alignments can be derived from multiple sequence alignments. One suitable program to generate multiple sequence alignments is ClustalW2, available from www.clustal.org. Another suitable program is MUSCLE, available from www.drive5.com/muscle/. ClustalW2 and MUSCLE are alternatively available, e.g., from the EBI.

It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at www.tcoffee.org, and alternatively available, e.g., from the EBI. It will also be appreciated that the final alignment used to calculate percent sequence identity can be curated either automatically or manually.

The term "consensus sequence," as used herein with respect to light chain (VL) and heavy chain (VH) variable regions, refers to a composite or genericized VL or VH sequence defined based on information as to which amino acid residues within the VL or VH chain are amenable to modification without detriment to antigen-binding. Thus, in a "consensus sequence" for a VL or VH chain, certain amino acid positions are occupied by one of multiple possible amino acid residues at that position. For example, if an arginine (R) or a serine (S) occur at a particular position, then that particular position within the consensus sequence can be either arginine or serine (R or S). Consensus sequences for VH and VL chain can be defined, for example, by in vitro affinity maturation (e.g., randomizing every amino acid position in a certain CDR using degenerate coding primers), by scanning mutagenesis (e.g., alanine scanning mutagenesis) of amino acid residues within the antibody CDRs, or any other methods known in the art, followed by evaluation of the binding of the mutants to the antigen to determine whether the mutated amino acid position affects antigen-binding. In some aspects, mutations are introduced in the CDR regions. In other aspects, mutations are introduced in framework regions. In some other aspects, mutations are introduced in CDR and framework regions.

II. CD73-Binding Molecules

The present disclosure provides CD73 binding molecules, e.g., antibodies and antigen-binding fragments thereof that specifically bind CD73, for example, human CD73. The full-length amino acid (aa) and nucleotide (nt) sequences for CD73 are known in the art (see, e.g., UniProt Acc. No. P21589 for human CD73, or UniProt Acc. No. Q61503 for mouse CD73). In some aspects, the anti-CD73 binding molecules are human antibodies (for example, a clone 10.3 antibody, a clone 2C5 antibody, MEDI9447). In certain aspects, the CD73 binding molecules are antibodies or antigen-binding fragments thereof.

In some aspects, CD73 binding molecules, e.g., antibodies or antigen-binding fragments thereof comprise a Fab, a Fab', a F(ab)$_2$, a Fd, a single chain Fv or scFv, a disulfide linked Fv, a V-NAR domain, an IgNar, an intrabody, an IgG CH2, a minibody, a F(ab')$_3$, a tetrabody, a triabody, a diabody, a single-domain antibody, DVD-Ig, Fcab, mAb$^2$, a (scFv)$_2$, or a scFv-Fc. In some aspects, the antibody is of the IgG type, for example of the IgG1 type.

In some aspects, the anti-CD73 antibody (for example, MEDI9447, a clone 10.3 antibody or a clone 2C5 antibody) or antigen-binding fragment thereof comprises a heavy chain constant region or fragment thereof. In some specific aspects, the heavy chain constant region is an IgG constant region. The IgG constant region can comprise a light chain constant region selected from the group consisting of a kappa constant region and a lambda constant region.

In certain aspects, anti-CD73 antibodies or antigen-binding fragments thereof disclosed herein are modified compared to a parent antibody, e.g., the CD730010 antibody or the CD730002 antibody. In some aspects, the parent antibody is CD730010. In other aspects, the parent antibody is CD730002. In other aspects, the parent antibody is CD730004, CD730008, CD7300011, CD730021, CD730042, CD730046, CD730047, CD730068, or CD730069. The modifications can include mutations in the CDR regions and/or in the FW regions as compared to the parent antibody, e.g., CD730010 or CD730002.

The phrase "CD730002 antibody" refers to an IgG1 comprising two VL domains comprising the amino acid sequence of SEQ ID NO:1 and two VH domains comprising the amino acid sequence of SEQ ID NO: 2.

The phrase "CD730004 antibody" refers to an IgG1 comprising two VL domains comprising the amino acid sequence of SEQ ID NO:104 and two VH domains comprising the amino acid sequence of SEQ ID NO:103.

The phrase "CD730008 antibody" refers to an IgG1 comprising two VL domains comprising the amino acid sequence of SEQ ID NO:106 and two VH domains comprising the amino acid sequence of SEQ ID NO: 107.

The phrase "CD730010 antibody" refers to an IgG1 comprising two VL domains comprising the amino acid sequence of SEQ ID NO:3 and two VH domains comprising the amino acid sequence of SEQ ID NO: 4.

The phrase "CD730011 antibody" refers to an IgG1 comprising two VL domains comprising the amino acid sequence of SEQ ID NO:5 and two VH domains comprising the amino acid sequence of SEQ ID NO: 6.

The phrase "CD730021 antibody" refers to an IgG1 comprising two VL domains comprising the amino acid sequence of SEQ ID NO:7 and two VH domains comprising the amino acid sequence of SEQ ID NO: 8.

The phrase "CD730042 antibody" refers to an IgG1 comprising two VL domains comprising the amino acid sequence of SEQ ID NO:9 and two VH domains comprising the amino acid sequence of SEQ ID NO: 10.

The phrase "CD730046 antibody" refers to an IgG1 comprising two VL domains comprising the amino acid sequence of SEQ ID NO:11 and two VH domains comprising the amino acid sequence of SEQ ID NO:12.

The phrase "CD730047 antibody" refers to an IgG1 comprising two VL domains comprising the amino acid sequence of SEQ ID NO:13 and two VH domains comprising the amino acid sequence of SEQ ID NO:14.

The phrase "CD730068 antibody" refers to an IgG1 comprising two VL domains comprising the amino acid sequence of SEQ ID NO:108 and two VH domains comprising the amino acid sequence of SEQ ID NO:107.

The phrase "CD730069 antibody" refers to an IgG1 comprising two VL domains comprising the amino acid sequence of SEQ ID NO:110 and two VH domains comprising the amino acid sequence of SEQ ID NO:109.

(i) CD730010-Derived Anti-CD73 Antibodies

In certain aspects, an anti-CD73 antibody of the present disclosure comprises modifications to CDR1 and/or CDR2 and/or CDR3 of the light chain of the CD730010 antibody, including, but not limited to:

1) a light chain CDR1 comprising the consensus sequence SGSLSNIGRNX$_1$VN (SEQ ID NO: 132), wherein X$_1$ represents amino acid residues Proline (P), Glutamic Acid (E) or Aspartic Acid (D); and/or, 2) a light chain CDR2 comprising the consensus sequence LX$_2$NX$_3$RX$_4$X$_5$ (SEQ ID NO: 133), wherein X$_2$ represents amino acid residues Asparagine (N) or Aspartic Acid (D), X$_3$ represents amino acid residues Glutamine (Q) or Leucine (L), X$_4$ represents amino acid residues Leucine (L) or Proline (P), and X$_5$ represents amino acid residues Glycine (G) or Serine (S); and/or, 3) a light chain CDR3 comprising the consensus sequence ATWDDSX$_6$X$_7$GWX$_8$ (SEQ ID NO: 134), wherein X$_6$ represents amino acid residues Leucine (L) or Histidine (H), X$_7$ represents amino acid residues Lysine (K), Proline (P), Isoleucine (I) or Asparagine (N), and X$_8$ represents amino acid residues Leucine (L) or Threonine (T).

In certain aspects, an anti-CD73 antibody of the present disclosure comprises modifications to CDR1 and/or CDR2 and/or CDR3 of the heavy chain of the CD730010 antibody, including, but not limited to:

1) a heavy chain CDR1 comprising the consensus sequence SYAX$_9$S (SEQ ID NO: 135), wherein X$_9$ represents amino acid residues Methionine (M) or Tyrosine (Y); and/or, 2) a heavy chain CDR2 comprising the consensus sequence X$_{10}$IX$_{11}$GSX$_{12}$GX$_{13}$TYYADSVKG (SEQ ID NO: 136), wherein X$_{10}$ represents amino acid residues Leucine (L) or Alanine (A), X$_{11}$ represents amino acid residues Tryptophan (W) or Serine (S), X$_{12}$ represents amino acid residues Tryptophan (W) or Glycine (G), and X$_{13}$ represents amino acid residues Serine (S) or Arginine (R); and/or, 3) a heavy chain CDR3 comprising the consensus sequence LGYX$_{14}$X$_{15}$X$_{16}$DX$_{17}$ (SEQ ID NO: 137), wherein X₁₄ represents amino acid residues Glycine (G) or Serine (S), X₁₅ represents amino acid residues Arginine (R) or Threonine (T), X₁₆ represents amino acid residues Valine (V) or Isoleucine (I), and X₁₇ represents amino acid residues Tyrosine (Y), Lysine (K), Methionine (M), Leucine (L) or Glutamic acid (E).

In one aspect, the anti-CD73 antibody or antigen-binding fragment thereof comprises a VL region comprising the consensus amino acid sequence:

(SEQ ID NO: 138)
[FW₁]SGSLSNIGRNX₁VN[FW₂]LX₂NX₃RX₄X₅[FW₃]ATWDDSX₆X₇GWX₈[FW₄]

wherein [FW₁], [FW₂], [FW₃] and [FW₄] represent the amino acid residues of VL framework region 1 (SEQ ID NO: 25 or 26), VL framework region 2 (SEQ ID NO: 27 or 28), VL framework region 3 (SEQ ID NO: 29) and VL framework region 4 (SEQ ID NO: 30), respectively, and wherein X₁ represents amino acid residues Proline (P), Glutamic Acid (E) or Aspartic Acid (D);
X₂ represents amino acid residues Asparagine (N) or Aspartic Acid (D);
X₃ represents amino acid residues Glutamine (Q) or Leucine (L);
X₄ represents amino acid residues Leucine (L) or Proline (P);
X₅ represents amino acid residues Glycine (G) or Serine (S);
X₆ represents amino acid residues Leucine (L) or Histidine (H);
X₇ represents amino acid residues Lysine (K), Proline (P), Isoleucine (I) or Asparagine (N); and, X₈ represents amino acid residues Leucine (L) or Threonine (T).

In one aspect, the anti-CD73 antibody or antigen-binding fragment thereof comprises a VH region which comprises the consensus amino acid sequence:

(SEQ ID NO: 139)
[FW₅]SYAX₉S[FW₆]X₁₀IX₁₁GSX₁₂GX₁₃TYYADSVKG[FW₇]LGYX₁₄X₁₅X₁₆DX₁₇[FW₈]

wherein [FW₅], [FW₆], [FW₇] and [FW₈] represent the amino acid residues of VH framework region 1 (SEQ ID NO: 31), VH framework region 2 (SEQ ID NO: 32), VH framework region 3 (SEQ ID NO: 33) and VH framework region 4 (SEQ ID NO: 34), respectively, and wherein
X₉ represents amino acid residues Methionine (M) or Tyrosine (Y);
X₁₀ represents amino acid residues Leucine (L) or Alanine (A);
X₁₁ represents amino acid residues Tryptophan (W) or Serine (S);
X₁₂ represents amino acid residues Tryptophan (W) or Glycine (G);
X₁₃ represents amino acid residues Serine (S) or Arginine (R);
X₁₄ represents amino acid residues Glycine (G) or Serine (S);
X₁₅ represents amino acid residues Arginine (R) or Threonine (T);
X₁₆ represents amino acid residues Valine (V) or Isoleucine (I)
X₁₇ represents amino acid residues Tyrosine (Y), Lysine (K), Methionine (M), Leucine (L) or Glutamic acid (E).

In one aspect, the anti-CD73 antibody or antigen-binding fragment thereof comprises a VL region comprising the consensus amino acid sequence:

(SEQ ID NO: 138)
[FW₁]SGSLSNIGRNX₁VN[FW₂]LX₂NX₃RX₄X₅[FW₃]ATWDDSX₆X₇GWX₈[FW₄]

wherein [FW₁], [FW₂], [FW₃] and [FW₄] represent the amino acid residues of VL framework region 1 (SEQ ID NO: 25 or 26), VL framework region 2 (SEQ ID NO: 27 or 28), VL framework region 3 (SEQ ID NO: 29) and VL framework region 4 (SEQ ID NO: 30), respectively, and wherein
X₁ represents amino acid residues Proline (P), Glutamic Acid (E) or Aspartic Acid (D);
X₂ represents amino acid residues Asparagine (N) or Aspartic Acid (D);
X₃ represents amino acid residues Glutamine (Q) or Leucine (L);
X₄ represents amino acid residues Leucine (L) or Proline (P);
X₅ represents amino acid residues Glycine (G) or Serine (S);
X₆ represents amino acid residues Leucine (L) or Histidine (H);
X₇ represents amino acid residues Lysine (K), Proline (P), Isoleucine (I) or Asparagine (N); and,
X₈ represents amino acid residues Leucine (L) or Threonine (T);
and wherein the anti-CD73 antibody or antigen-binding fragment thereof further comprises a VH region which comprises the consensus amino acid sequence:

(SEQ ID NO: 139)
[FW₅]SYAX₉S[FW₆]X₁₀IX₁₁GSX₁₂GX₁₃TYYADSVKG[FW₇]LGYX₁₄X₁₅X₁₆DX₁₇[FW₈]

wherein [FW₅], [FW₆], [FW₇] and [FW₈] represent the amino acid residues of VH framework region 1 (SEQ ID NO: 31), VH framework region 2 (SEQ ID NO: 32), VH framework region 3 (SEQ ID NO: 33) and VH framework region 4 (SEQ ID NO: 34), respectively, and wherein
X₉ represents amino acid residues Methionine (M) or Tyrosine (Y);
X₁₀ represents amino acid residues Leucine (L) or Alanine (A);
X₁₁ represents amino acid residues Tryptophan (W) or Serine (S);
X₁₂ represents amino acid residues Tryptophan (W) or Glycine (G);
X₁₃ represents amino acid residues Serine (S) or Arginine (R);
X₁₄ represents amino acid residues Glycine (G) or Serine (S);
X₁₅ represents amino acid residues Arginine (R) or Threonine (T);
X₁₆ represents amino acid residues Valine (V) or Isoleucine (I)
X₁₇ represents amino acid residues Tyrosine (Y), Lysine (K), Methionine (M), Leucine (L) or Glutamic acid (E).

In some aspects, the anti-CD73 antibody or antigen-binding fragment thereof comprises a VL-CDR1 consisting of a sequence selected from the group consisting of SEQ ID NOs: 46, 47, and 48. In some aspects, the anti-CD73 antibody or antigen-binding fragment thereof comprises a VL-CDR1 comprising a sequence selected from the group consisting of SEQ ID NOs: 46, 47, and 48.

In some aspects, the anti-CD73 antibody or antigen-binding fragment thereof comprises a VL-CDR2 consisting of a sequence selected from the group consisting of SEQ ID NOs: 49, 50, 51, and 52. In some aspects, the anti-CD73 antibody or antigen-binding fragment thereof comprises a VL-CDR2 comprising a sequence selected from the group consisting of SEQ ID NOs: 49, 50, 51 and 52.

In some aspects, the anti-CD73 antibody or antigen-binding fragment thereof comprises a VL-CDR3 consisting of a sequence selected from the group consisting of SEQ ID NOs: 53, 54, 55, and 56. In some aspects, the anti-CD73 antibody or antigen-binding fragment thereof comprises a VL-CDR3 comprising a sequence selected from the group consisting of SEQ ID NOs: 53, 54, 55, and 56.

In some aspects, the anti-CD73 antibody or antigen-binding fragment thereof comprises a VH-CDR1 consisting of a sequence selected from the group consisting of SEQ ID NOs: 35 and 36. In some aspects, the anti-CD73 antibody or antigen-binding fragment thereof comprises a VH-CDR1 comprising a sequence selected from the group consisting of SEQ ID NOs: 35 and 36.

In some aspects, the anti-CD73 antibody or antigen-binding fragment thereof comprises a VH-CDR2 consisting of a sequence selected from the group consisting of SEQ ID NOs: 37, 38, 39, and 40. In some aspects, the anti-CD73 antibody or antigen-binding fragment thereof comprises a VH-CDR2 comprising a sequence selected from the group consisting of SEQ ID NOs: 37, 38, 39, and 40.

In some aspects, the anti-CD73 antibody or antigen-binding fragment thereof comprises a VH-CDR3 consisting of a sequence selected from the group consisting of SEQ ID NOs: 41, 42, 43, 44, and 45. In some aspects, the anti-CD73 antibody or antigen-binding fragment thereof comprises a VH-CDR3 comprising a sequence selected from the group consisting of SEQ ID NOs: 41, 42, 43, 44, and 45.

In some aspects, the anti-CD73 antibody or antigen-binding fragment thereof comprises a VL-CDR1 consisting of a sequence selected from the group consisting of SEQ ID NOs: 46, 47, and 48, except for one, two, three or four amino acid substitutions. In some aspects, the anti-CD73 antibody or antigen-binding fragment comprises a VL-CDR1 comprising a sequence selected from the group consisting of SEQ ID NOs: 46, 47, and 48, except for one, two, three or four amino acid substitutions.

In some aspects, the anti-CD73 antibody or antigen-binding fragment thereof comprises a VL-CDR2 consisting of a sequence selected from the group consisting of SEQ ID NOs: 49, 50, 51, and 52, except for one, two, three, or four amino acid substitutions. In some aspects, the anti-CD73 antibody or antigen-binding fragment thereof comprises a VL-CDR2 comprising a sequence selected from the group consisting of SEQ ID NOs: 49, 50, 51, and 52, except for one, two, three or four amino acid substitutions.

In some aspects, the anti-CD73 antibody or antigen-binding fragment thereof comprises a VL-CDR3 consisting of a sequence selected from the group consisting of SEQ ID NOs: 53, 54, 55, and 56, except for one, two, three, or four amino acid substitutions. In some aspects, the anti-CD73 antibody or antigen-binding fragment thereof comprises a VL-CDR3 comprising a sequence selected from the group consisting of SEQ ID NOs: 53, 54, 55, and 56, except for one, two, three or four amino acid substitutions.

In some aspects, the anti-CD73 antibody or antigen-binding fragment thereof comprises a VH-CDR1 consisting of a sequence selected from the group consisting of SEQ ID NOs: 35 and 36, except for one, two, three, or four amino acid substitutions. In some aspects, the anti-CD73 antibody or antigen-binding fragment thereof comprises a VH-CDR1 comprising a sequence selected from the group consisting of SEQ ID NOs: 35 and 36, except for one, two, three or four amino acid substitutions.

In some aspects, the anti-CD73 antibody or antigen-binding fragment thereof comprises a VH-CDR2 consisting of a sequence selected from the group consisting of SEQ ID NOs: 37, 38, 39, and 40, except for one, two, three, or four amino acid substitutions. In some aspects, the anti-CD73 antibody or antigen-binding fragment thereof comprises a VH-CDR2 comprising a sequence selected from the group consisting of SEQ ID NOs: 37, 38, 39, and 40, except for one, two, three or four amino acid substitutions.

In some aspects, the anti-CD73 antibody or antigen-binding fragment thereof comprises a VH-CDR3 consisting of a sequence selected from the group consisting of SEQ ID NOs: 41, 42, 43, 44, and 45, except for one, two, three, or four amino acid substitutions. In some aspects, the anti-CD73 antibody or antigen-binding fragment thereof comprises a VH-CDR3 comprising sequence selected from the group consisting of SEQ ID NOs: 41, 42, 43, 44, and 45, except for one, two, three or four amino acid substitutions.

In some aspects, the anti-CD73 antibody or antigen-binding fragment thereof comprises a VL-CDR1 consisting of a sequence selected from the group consisting of SEQ ID NOs: 46, 47 and 48; a VL-CDR2 consisting of a sequence selected from the group consisting of SEQ ID NOs: 49, 50, 51, and 52; and a VL-CDR3 consisting of a sequence selected from the group consisting of SEQ ID NOs: 53, 54, 55, and 56. In some aspects, the anti-CD73 antibody or antigen-binding fragment thereof comprises a VL-CDR1 comprising a sequence selected from the group consisting of SEQ ID NOs: 46, 47 and 48; a VL-CDR2 comprising a sequence selected from the group consisting of SEQ ID NOs: 49, 50, 51, and 52; and a VL-CDR3 comprising a sequence selected from the group consisting of SEQ ID NOs: 53, 54, 55, and 56.

In some aspects, the anti-CD73 antibody or antigen-binding fragment thereof comprises a VH-CDR1 consisting of a sequence selected from the group consisting of SEQ ID NOs: 35 and 36; a VH-CDR2 consisting of a sequence selected from the group consisting of SEQ ID NOs: 37, 38, 39, and 40; and a VH-CDR3 consisting of a sequence selected from the group consisting of SEQ ID NOs: 41, 42, 43, 44, and 45. In some aspects, the anti-CD73 antibody or antigen-binding fragment thereof comprises a VH-CDR1 comprising a sequence selected from the group consisting of SEQ ID NOs: 35 and 36; a VH-CDR2 comprising a sequence selected from the group consisting of SEQ ID NOs: 37, 38, 39, and 40; a VH-CDR3 comprising a sequence selected from the group consisting of SEQ ID NOs: 41, 42, 43, 44, and 45.

In some aspects, the anti-CD73 antibody or antigen-binding fragment thereof comprises a VL-CDR1 consisting of a sequence selected from the group consisting of SEQ ID NOs: 46, 47 and 48 except for one, two, three or four amino acid substitutions; a VL-CDR2 consisting of a sequence selected from the group consisting of SEQ ID NOs: 49, 50, 51, and 52 except for one, two, three or four amino acid substitutions; and a VL-CDR3 consisting of a sequence selected from the group consisting of SEQ ID NOs: 53, 54, 55, and 56 except for one, two, three or four amino acid substitutions.

In some aspects, the anti-CD73 antibody or antigen-binding fragment thereof comprises a VL-CDR1 comprising a sequence selected from the group consisting of SEQ ID NOs: 46, 47 and 48 except for one, two, three, or four amino acid substitutions; a VL-CDR2 comprising a sequence selected from the group consisting of SEQ ID NOs: 49, 50, 51, and 52 except for one, two, three, or four amino acid substitutions; and a VL-CDR3 comprising a sequence selected from the group consisting of SEQ ID NOs: 53, 54, 55, and 56 except for one, two, three or four amino acid substitutions.

In some aspects, the anti-CD73 antibody or antigen-binding fragment thereof comprises a VH-CDR1 consisting of a sequence selected from the group consisting of SEQ ID NOs: 35 and 36 except for one, two, three, or four amino acid substitutions; a VH-CDR2 consisting of a sequence selected from the group consisting of SEQ ID NOs: 37, 38, 39, and 40 except for one, two, three, or four amino acid substitutions; and a VH-CDR3 consisting of a sequence selected from the group consisting of SEQ ID NOs: 41, 42, 43, 44, and 45 except for one, two, three or four amino acid substitutions.

In some aspects, the anti-CD73 antibody or antigen-binding fragment thereof comprises a VH-CDR1 comprising a sequence selected from the group consisting of SEQ ID NOs: 35 and 36 except for one, two, three, or four amino acid substitutions; a VH-CDR2 comprising a sequence selected from the group consisting of SEQ ID NOs: 37, 38, 39, and 40 except for one, two, three, or four amino acid substitutions; a VH-CDR3 comprising a sequence selected from the group consisting of SEQ ID NOs: 41, 42, 43, 44, and 45 except for one, two, three or four amino acid substitutions.

In certain aspects, the anti-CD73 antibody or antigen-binding fragment thereof comprises modifications to CDR1, and/or CDR2, and/or CDR3 of the heavy and/or light chain, and further comprises modifications to $FW_1$, and/or $FW_2$, and/or $FW_3$, and/or $FW_4$ of the heavy and/or light chain.

In some aspects, $FW_1$ comprises SEQ ID NO: 25 or 26, $FW_2$ comprises SEQ ID NO: 27 or 28, $FW_3$ comprises SEQ ID NO: 29, $FW_4$ comprises SEQ ID NO: 30, $FW_5$ comprises SEQ ID NO: 31, $FW_6$ comprises SEQ ID NO: 32, $FW_7$ comprises SEQ ID NO: 33, and $FW_8$ comprises SEQ ID NO: 34.

In some aspects, $FW_1$ comprises SEQ ID NO: 25 or 26, except for one, two, three, or four amino acid substitutions; $FW_2$ comprises SEQ ID NO: 27 or 28, except for one, two, three, or four amino acid substitutions; $FW_3$ comprises SEQ ID NO: 29, except for one, two, three, or four amino acid substitutions; $FW_4$ comprises SEQ ID NO: 30, except for one, two, three, or four amino acid substitutions; $FW_5$ comprises SEQ ID NO: 31, except for one, two, three, or four amino acid substitutions; $FW_6$ comprises SEQ ID NO: 32, except for one, two, three, or four amino acid substitutions; $FW_7$ comprises SEQ ID NO: 33, except for one, two, three, or four amino acid substitutions; and $FW_8$ comprises SEQ ID NO: 34.

In certain aspects, the anti-CD733 antibody or antigen-binding fragment thereof comprises a VL and a VH comprising VL-CDR1, VL-CRD2, VL-CDR3, VH-CDR1, VH-CDR2, and VH-CDR3 amino acid sequences identical or identical except for one, two, three or four amino acid substitutions in one or more CDRs, wherein such VL-CDR1, VL-CRD2, VL-CDR3, VH-CDR1, VH-CDR2, and VH-CDR3 are:

SEQ ID NOs: 46, 49, 53, 35, 37, and 41; or,
SEQ ID NOs: 47, 49, 53, 35, 37 and 41; or,
SEQ ID NOs: 47, 49, 54, 36, 37 and 42; or,
SEQ ID NOs: 46, 50, 54, 36, 38 and 43; or,
SEQ ID NOs: 46, 51, 55, 36, 39 and 44; or,
SEQ ID NOs: 48, 52, 54, 36, 40 and 44; or,
SEQ ID NOs: 46, 49, 56, 35, 37 and 41; or,
SEQ ID NOs: 46, 49, 53, 35, 37 and 45; or,
SEQ ID NOs: 47, 49, 56, 36, 37 and 45; or,
SEQ ID NOs: 46, 50, 56, 36, 38 and 45; or,
SEQ ID NOs: 46, 51, 56, 36, 39 and 45; or,
SEQ ID NOs: 48, 52, 56, 36, 40 and 45; or
SEQ ID NOs: 46, 49, 56, 35, 37 and 45, respectively.

In certain aspects, the anti-CD73 antibody or antigen-binding fragment thereof comprises an antibody VL and an antibody VH, wherein the VL comprises an amino acid sequence at least about 80%, about 85%, about 90%, about 95%, about 96%, about 97%, about 98%, about 99%, or about 100% identical to a reference amino acid sequence selected from the group consisting of SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, and SEQ ID NO: 70.

In other aspects, the anti-CD73 antibody or antigen-binding fragment thereof comprises an antibody VL and an antibody VH, wherein the VH comprises an amino acid sequence at least about 80%, about 85%, about 90%, about 95%, about 96%, about 97%, about 98%, about 99%, or about 100% identical to a reference amino acid sequence selected from the group consisting of SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 80, SEQ ID NO: 81, SEQ ID NO: 82, SEQ ID NO: 83 and SEQ ID NO: 84.

In other aspects, the anti-CD73 antibody or antigen-binding fragment thereof comprises a VL comprising a sequence at least about 80%, about 85%, about 90%, about 95%, about 96%, about 97%, about 98%, about 99%, or about 100% identical to a reference amino acid sequence selected from the group consisting of SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, and SEQ ID NO: 70, and further comprises a VH comprising a sequence at least about 80%, about 85%, about 90%, about 95%, about 96%, about 97%, about 98%, about 99%, or about 100% identical to a reference amino acid sequence selected from the group consisting of SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83 and SEQ ID NO: 84.

In some aspects, the anti-CD73 antibody or antigen-binding fragment thereof comprises a VL comprising the sequence of SEQ ID NO: 68 and a VH comprising the sequence of SEQ ID NO:82. In some aspects, the anti-CD73 antibody or antigen-binding fragment thereof comprises a VL consisting of the sequence of SEQ ID NO:68 and a VH consisting of the sequence of SEQ ID NO:82.

The "clone 10.3 antibody" (also designated "73combo3" or "MEDI9447") is an IgG1 comprising two CD730010-derived light chains (VL) of SEQ ID NO: 68 (comprising three CDRs, CDR1, CDR2, and CDR3, with the sequences of SEQ ID NO: 46, 51 and 56, respectively), and two CD730010-derived heavy chains (VH) of SEQ ID NO: 82 (comprising three CDRs, CDR1, CDR2, and CDR3, with the sequences of SEQ ID NO: 36, 39, and 45, respectively).

In certain aspects, an anti-CD73 antibody or antigen-binding fragment thereof disclosed herein binds CD73 with substantially the same or better affinity as a 10.3 antibody comprising the 10.3 heavy chain VH of SEQ ID NO: 82 and the 10.3 light chain VL of SEQ ID NO: 68.

(ii) CD730002-Derived Anti-CD73 Antibodies

In certain aspects, the anti-CD73 antibody of the present disclosure comprises modifications to CDR1 and/or CDR2 and/or CDR3 of the light chain of the CD730002 antibody, including, but not limited to:

1) a light chain CDR1 comprising the sequence SGDKVGDKYAS (SEQ ID NO: 97); and/or, 2) a light chain CDR2 comprising the consensus sequence $EDX_{18}KX_{19}X_{20}S$ (SEQ ID NO: 140), wherein $X_{18}$ represents amino acid residues Serine (S) or Threonine (T), $X_{19}$ represents amino acid residues Arginine (R) or Tyrosine (Y), and $X_{20}$ represents amino acid residues Histidine (H), Proline (P) or Leucine (L); and/or, 3) a light chain CDR3 comprising the sequence QAWDTSFWV (SEQ ID NO: 100).

In certain aspects, the anti-CD73 antibody of the present disclosure comprises modifications to CDR1 and/or CDR2 and/or CDR3 of the heavy chain of CD730002, including, but not limited to:

1) a heavy chain CDR1 comprising the sequence $SX_{21}AX_{22}S$ (SEQ ID NO: 141), wherein $X_{21}$ represents amino acid residues Tyrosine (Y) or Valine (V), and $X_{22}$ represents amino acid residues Methionine (M) or Arginine (R); and/or, 2) a heavy chain CDR2 comprising the sequence $AISGSGGSX_{23}YY\ X_{24}DSVKX_{25}$ (SEQ ID NO: 142), wherein $X_{23}$ represents amino acid residues Threonine (T) or Proline (P); $X_{24}$ represents amino acid residues Alanine (A) or G (Glycine); and $X_{25}$ represents amino acid residues Glycine (G) or Arginine (R); and/or, 3) a heavy chain CDR3 comprising the sequence DKGYYWYM (SEQ ID NO: 143).

In one aspect, the anti-CD73 antibody or antigen-binding fragment thereof comprises a VL region comprising the consensus amino acid sequence:

(SEQ ID NO: 144)
$[FW_9]SGDKVGDKYAS[FW_{10}]EDX_{18}KX_{19}X_{20}S[FW_{11}]QAWDTSFWV[FW_{12}]$ wherein $[FW_9]$, $[FW_{10}]$, $[FW_{11}]$ and $[FW_{12}]$ represent the amino acid residues of VL framework region 1 (SEQ ID NO: 90 or 91), VL framework region 2 (SEQ ID NO: 92), VL framework region 3 (SEQ ID NO: 93, 94 or 122) and VL framework region 4 (SEQ ID NO: 30), respectively; and wherein $X_{18}$ represents amino acid residues Proline (P) or Leucine (L); $X_{19}$ represents amino acid residues Arginine (R) or Tyrosine (Y); and $X_{20}$ represents amino acid residues Histidine (H), Proline (P) or Leucine (L).

In one aspect, the anti-CD73 antibody or antigen-binding fragment thereof comprises a VH region which comprises the consensus amino acid sequence:

(SEQ ID NO: 145)
$[FW_{13}]SX_{21}AX_{22}S[FW_{14}]AISGSGGSX_{23}YYX_{24}DSVKX_{25}[FW_{15}]DKGYYWYM[FW_{16}]$ wherein $[FW_{13}]$, $[FW_{14}]$, $[FW_{15}]$ and $[FW_{16}]$ represent the amino acid residues of VH framework region 1 (SEQ ID NO: 31), VH framework region 2 (SEQ ID NO: 32), VH framework region 3 (SEQ ID NO: 33) and VH framework region 4 (SEQ ID NO: 89), respectively; and wherein $X_{21}$ represents amino acid residues Tyrosine (Y) or Valine (V); $X_{22}$ represents amino acid residues Methionine (M) or Arginine (R); $X_{23}$ represents amino acid residues Threonine (T) or Proline (P); $X_{24}$ represents amino acid residues Alanine (A) or G (Glycine); and $X_{25}$ represents amino acid residues Glycine (G) or Arginine (R).

In one aspect, the anti-CD73 antibody or antigen-binding fragment thereof comprises a VL region comprising the consensus amino acid sequence:

(SEQ ID NO: 144)
$[FW_9]SGDKVGDKYAS[FW_{10}]EDX_{18}KX_{19}X_{20}S[FW_{11}]QAWDTSFWV[FW_{12}]$ wherein $[FW_9]$, $[FW_{10}]$, $[FW_{11}]$ and $[FW_{12}]$ represent the amino acid residues of VL framework region 1 (SEQ ID NO: 90 or 91), VL framework region 2 (SEQ ID NO: 92), VL framework region 3 (SEQ ID NO: 93, 94 or 122) and VL framework region 4 (SEQ ID NO: 30), respectively; and wherein $X_{18}$ represents amino acid residues Proline (P) or Leucine (L); $X_{19}$ represents amino acid residues Arginine (R) or Tyrosine (Y); and $X_{20}$ represents amino acid residues Histidine (H), Proline (P) or Leucine (L), and wherein the anti-CD73 antibody or antigen-binding fragment thereof further comprises a VH region which comprises the consensus amino acid sequence:

(SEQ ID NO: 145)
$[FW_{13}]SX_{21}AX_{22}S[FW_{14}]AISGSGGSX_{23}YYX_{24}DSVKX_{25}[FW_{15}]DKGYYWYM[FW_{16}]$ wherein $[FW_{13}]$, $[FW_{14}]$, $[FW_{15}]$ and $[FW_{16}]$ represent the amino acid residues of VH framework region 1 (SEQ ID NO: 31), VH framework region 2 (SEQ ID NO: 32), VH framework region 3 (SEQ ID NO: 33) and VH framework region 4 (SEQ ID NO: 89), respectively; and wherein $X_{21}$ represents amino acid residues Tyrosine (Y) or Valine (V); $X_{22}$ represents amino acid residues Methionine (M) or Arginine (R); $X_{23}$ represents amino acid residues Threonine (T) or Proline (P); $X_{24}$ represents amino acid residues Alanine (A) or G (Glycine); and $X_{25}$ represents amino acid residues Glycine (G) or Arginine (R).

In some aspects, the anti-CD73 antibody or antigen-binding fragment thereof comprises a VL-CDR1 consisting of a sequence consisting of SEQ ID NO: 97. In some aspects, the anti-CD73 antibody or antigen-binding fragment thereof comprises a VL-CDR1 comprising a sequence consisting of SEQ ID NO: 97.

In some aspects, the anti-CD73 antibody or antigen-binding fragment thereof comprises a VL-CDR2 consisting of a sequence selected from the group consisting of SEQ ID NOs: 98, 99, 127, 128, and 129. In some aspects, the anti-CD73 antibody or antigen-binding fragment thereof comprises a VL-CDR2 comprising a sequence selected from the group consisting of SEQ ID NOs: 98, 99, 127, 128 and 129.

In some aspects, the anti-CD73 antibody or antigen-binding fragment thereof comprises a VL-CDR3 consisting of a sequence consisting of SEQ ID NO: 100. In some aspects, the anti-CD73 antibody or antigen-binding fragment thereof comprises a VL-CDR3 comprising a sequence consisting of SEQ ID NO: 100.

In some aspects, the anti-CD73 antibody or antigen-binding fragment thereof comprises a VH-CDR1 consisting of a sequence of a sequence selected from the group consisting of SEQ ID NOs: 35, 123 and 124. In some aspects, the anti-CD73 antibody or antigen-binding fragment thereof comprises a VH-CDR1 comprising a sequence selected from the group consisting of SEQ ID NOs: 35, 123 and 124.

In some aspects, the anti-CD73 antibody or antigen-binding fragment thereof comprises a VH-CDR2 consisting of a sequence selected from the group consisting of SEQ ID NOs: 37, 95, 125 and 126. In some aspects, the anti-CD73 antibody or antigen-binding fragment thereof comprises a VH-CDR2 comprising a sequence selected from the group consisting of SEQ ID NOs: 37, 95, 125, and 126.

In some aspects, the anti-CD73 antibody or antigen-binding fragment thereof comprises a VH-CDR3 consisting of a sequence consisting of SEQ ID NO: 96. In some aspects, the anti-CD73 antibody or antigen-binding fragment thereof comprises a VH-CDR3 comprising a sequence consisting of SEQ ID NO: 96.

In some aspects, the anti-CD73 antibody or antigen-binding fragment thereof comprises a VL-CDR1 consisting of a sequence consisting of SEQ ID NO: 97, except for one, two, three, or four amino acid substitutions. In some aspects, the anti-CD73 antibody or antigen-binding fragment thereof comprises a VL-CDR1 comprising a sequence consisting of SEQ ID NO: 97, except for one, two, three or four amino acid substitutions.

In some aspects, the anti-CD73 antibody or antigen-binding fragment thereof comprises a VL-CDR2 consisting of a sequence selected from the group consisting of SEQ ID NOs: 98, 99, 127, 128, and 129, except for one, two, three, or four amino acid substitutions. In some aspects, the anti-CD73 antibody or antigen-binding fragment thereof comprises a VL-CDR2 comprising a sequence selected from the group consisting of SEQ ID NOs: 98, 99, 127, 128, and 129, except for one, two, three, or four amino acid substitutions.

In some aspects, the anti-CD73 antibody or antigen-binding fragment thereof comprises a VL-CDR3 consisting of a sequence consisting of SEQ ID NO: 100, except for one, two, three, or four amino acid substitutions. In some aspects, the anti-CD73 antibody or antigen-binding fragment thereof comprises a VL-CDR3 comprising a sequence consisting of SEQ ID NO: 100, except for one, two, three, or four amino acid substitutions.

In some aspects, the anti-CD73 antibody or antigen-binding fragment thereof comprises a VH-CDR1 consisting of a sequence selected from the group consisting of SEQ ID NOs: 35, 123 and 124, except for one, two, three, or four amino acid substitutions. In some aspects, the anti-CD73 antibody or antigen-binding fragment thereof comprises a VH-CDR1 comprising a sequence selected from the group consisting of SEQ ID NOs: 35, 123 and 124, except for one, two, three, or four amino acid substitutions.

In some aspects, the anti-CD73 antibody or antigen-binding fragment thereof comprises a VH-CDR2 consisting of a sequence selected from the group consisting of SEQ ID NOs: 37, 95, 125 and 126, except for one, two, three, or four amino acid substitutions. In some aspects, the anti-CD73 antibody or antigen-binding fragment thereof comprises a VH-CDR2 comprising a sequence selected from the group consisting of SEQ ID NOs: 37, 95, 125 and 126, except for one, two, three, or four amino acid substitutions.

In some aspects, the anti-CD73 antibody or antigen-binding fragment thereof comprises a VH-CDR3 consisting of a sequence consisting of SEQ ID NO: 96, except for one, two, three, or four amino acid substitutions. In some aspects, the anti-CD73 antibody or antigen-binding fragment thereof comprises a VH-CDR3 comprising a sequence consisting of SEQ ID NO: 96, except for one, two, three, or four amino acid substitutions.

In some aspects, the anti-CD73 antibody or antigen-binding fragment thereof comprises a VL-CDR1 consisting of a sequence consisting of SEQ ID NO: 97; a VL-CDR2 consisting of a sequence selected from the group consisting of SEQ ID NOs: 98, 99, 127, 128, and 129; and a VL-CDR3 consisting of a sequence consisting of SEQ ID NO: 100. In some aspects, the anti-CD73 antibody or antigen-binding fragment thereof comprises a VL-CDR1 comprising a sequence consisting of SEQ ID NO: 97; a VL-CDR2 comprising a sequence selected from the group consisting of SEQ ID NOs: 98, 99, 127, 128, and 129; and a VL-CDR3 comprising a sequence consisting of SEQ ID NO: 100.

In some aspects, the anti-CD73 antibody or antigen-binding fragment thereof comprises a VH-CDR1 consisting of a sequence selected from the group consisting of SEQ ID NOs: 35, 123, and 124; a VH-CDR2 consisting of a sequence selected from the group consisting of SEQ ID NOs: 37, 95, 125, and 126; and a VH-CDR3 consisting of a sequence consisting of SEQ ID NOs: 96. In some aspects, the anti-CD73 antibody or antigen-binding fragment thereof comprises a VH-CDR1 comprising a sequence selected from the group consisting of SEQ ID NOs: 35, 123, and 124; a VH-CDR2 comprising a sequence selected from the group consisting of SEQ ID NOs: 37, 95, 125, and 126; a VH-CDR3 comprising a sequence consisting of SEQ ID NO: 96.

In some aspects, the anti-CD73 antibody or antigen-binding fragment thereof comprises a VL-CDR1 consisting of a sequence consisting of SEQ ID NO: 97, except for one, two, three, or four amino acid substitutions; a VL-CDR2 consisting of a sequence selected from the group consisting of SEQ ID NOs: 98, 99, 127, 128, and 129, except for one, two, three or four amino acid substitutions; and a VL-CDR3 consisting of a sequence consisting of SEQ ID NO: 100, except for one, two, three, or four amino acid substitutions.

In some aspects, the anti-CD73 antibody or antigen-binding fragment thereof comprises a VL-CDR1 comprising a sequence consisting of SEQ ID NOs: 97, except for one, two, three or four amino acid substitutions; a VL-CDR2 comprising a sequence selected from the group consisting of SEQ ID NOs: 98, 99, 127, 128, and 129, except for one, two, three or four amino acid substitutions; and a VL-CDR3 comprising a sequence consisting of SEQ ID NO:100, except for one, two, three or four amino acid substitutions.

In some aspects, the anti-CD73 antibody or antigen-binding fragment thereof comprises a VH-CDR1 consisting of a sequence selected from the group consisting of SEQ ID NOs: 35, 123, and 124, except for one, two, three or four amino acid substitutions; a VH-CDR2 consisting of a sequence selected from the group consisting of SEQ ID NOs: 37, 95, 125, and 126, except for one, two, three, or four amino acid substitutions; and a VH-CDR3 consisting of a sequence consisting of SEQ ID NO: 96, except for one, two, three or four amino acid substitutions.

In some aspects, the anti-CD73 antibody or antigen-binding fragment thereof comprises a VH-CDR1 comprising a sequence selected from the group consisting of SEQ ID NOs: 35, 123, and 124, except for one, two, three, or four amino acid substitutions; a VH-CDR2 comprising a sequence selected from the group consisting of SEQ ID NOs: 37, 95, 125, and 126, except for one, two, three, or four amino acid substitutions; a VH-CDR3 comprising a sequence consisting of SEQ ID NO: 96, except for one, two, three or four amino acid substitutions.

In certain aspects, the anti-CD73 antibody or antigen-binding fragment thereof comprises modifications to CDR1, and/or CDR2, and/or CDR3 of the heavy and/or light chain, and further comprises modifications to FW1, and/or FW2, and/or FW3, and/or FW4 of the heavy and/or light chain.

In some aspects, $FW_9$ comprises SEQ ID NO: 90 or 91, $FW_{10}$ comprises SEQ ID NO: 92, $FW_{11}$ comprises SEQ ID NO: 93, 94, or 122, $FW_{12}$ comprises SEQ ID NO: 30, $FW_{13}$ comprises SEQ ID NO: 31, FW$_{14}$ comprises SEQ ID NO: 32, FW$_{15}$ comprises SEQ ID NO: 33, and FW$_{16}$ comprises SEQ ID NO: 89.

In some aspects, FW$_9$ comprises SEQ ID NO: 90 or 91, except for one, two, three, or four amino acid substitutions, FW$_{10}$ comprises SEQ ID NO: 92, except for one, two, three, or four amino acid substitutions, FW$_{11}$ comprises SEQ ID NO: 93, 94, or 122, except for one, two, three, or four amino acid substitutions, FW$_{12}$ comprises SEQ ID NO: 30, except for one, two, three, or four amino acid substitutions, FW$_{13}$ comprises SEQ ID NO: 31, except for one, two, three, or four amino acid substitutions, FW$_{14}$ comprises SEQ ID NO: 32, except for one, two, three, or four amino acid substitutions, FW$_{15}$ comprises SEQ ID NO: 33, except for one, two, three or four amino acid substitutions, and FW$_{16}$ comprises SEQ ID NO: 89.

In certain aspects, the anti-CD733 antibody or antigen-binding fragment thereof comprises a VL and a VH comprising VL-CDR1, VL-CRD2, VL-CDR3, VH-CDR1, VH-CDR2, and VH-CDR3 amino acid sequences identical or identical except for one, two, three, or four amino acid substitutions in one or more CDRs, wherein such VL-CDR1, VL-CRD2, VL-CDR3, VH-CDR1, VH-CDR2, and VH-CDR3 are:
SEQ ID NOs: 97, 98, 100, 35, 37, and 96; or,
SEQ ID NOs: 97, 99, 100, 35, 95 and 96; or,
SEQ ID NOs: 97, 98, 100, 35, 37, and 96; or,
SEQ ID NOs: 97, 99, 100, 123, 37, and 96; or,
SEQ ID NOs: 97, 99, 100, 124, 37, and 96; or,
SEQ ID NOs: 97, 99, 100, 35, 125, and 96; or,
SEQ ID NOs: 97, 99, 100, 35, 126, and 96; or,
SEQ ID NOs: 97, 99, 100, 35, 95, and 96; or,
SEQ ID NOs: 97, 127, 100, 35, 95, and 96; or,
SEQ ID NOs: 97, 128, 100, 35, 95, and 96; or,
SEQ ID NOs: 97, 129, 100, 35, 95, and 96; or,
SEQ ID NOs: 97, 99, 100, 35, 95, and 96; respectively.

In certain aspects, the anti-CD73 antibody or antigen-binding fragment thereof comprises an antibody VL and an antibody VH, wherein the VL comprises an amino acid sequence at least about 80%, about 85%, about 90%, about 95%, about 96%, about 97%, about 98%, about 99%, or about 100% identical to a reference amino acid sequence selected from the group consisting of SEQ ID NOs: 86, 88, 112, 118, 119, 120, and 121.

In other aspects, the anti-CD73 antibody or antigen-binding fragment thereof comprises an antibody VL and an antibody VH, wherein the VH comprises an amino acid sequence at least about 80%, about 85%, about 90%, about 95%, about 96%, about 97%, about 98%, about 99%, or about 100% identical to a reference amino acid sequence selected from the group consisting of SEQ ID NOs: 85, 87, 111, 113, 114, 115, 116, and 117.

In other aspects, the anti-CD73 antibody or antigen-binding fragment thereof comprises a VL comprising a sequence at least about 80%, about 85%, about 90%, about 95%, about 96%, about 97%, about 98%, about 99%, or about 100% identical to a reference amino acid sequence selected from the group consisting of SEQ ID NOs: 86, 88, 112, 118, 119, 120, and 121; and further comprises a VH comprising a sequence at least about 80%, about 85%, about 90%, about 95%, about 96%, about 97%, about 98%, about 99%, or about 100% identical to a reference amino acid sequence selected from the group consisting of SEQ ID NOs: 85, 87, 111, 113, 114, 115, 116, and 117.

In some aspects, the anti-CD73 antibody or antigen-binding fragment thereof comprises a VL comprising the sequence of SEQ ID NO: 88; and a VH comprising the sequence of SEQ ID NO:87. In some aspects, the anti-CD73 antibody or antigen-binding fragment thereof comprises a VL consisting of the sequence of SEQ ID NO:87, and a VH consisting of the sequence of SEQ ID NO:87.

The "clone 2C5 antibody" is an IgG1 comprising two CD730002-derived light chains (VL) of SEQ ID NO: 88 (comprising three CDRs, CDR1, CDR2, and CDR3, with the sequences of SEQ ID NO: 97, 99, and 100, respectively), and CD7300002-derived heavy chains (VH) of SEQ ID NO: 87 (comprising three CDRs, CDR1, CDR2, and CDR3, with the sequences of SEQ ID NO: 35, 95, and 96, respectively).

In certain aspects, an anti-CD73 antibody or antigen-binding fragment thereof disclosed herein binds CD73 with substantially the same or better affinity as a 2C5 antibody comprising the 2C5 heavy chain VH of SEQ ID NO: 87 and the 2C5 light chain VL of SEQ ID NO: 88.

(iii) Anti-CD73 Antibodies with Parent Antibodies Other than CD730002 or CD730010

In other aspects, the parent antibody of an anti-CD73 antibody or antigen-binding fragment disclosed herein is CD730004 (i.e., an anti-CD73 antibody comprising a VL of SEQ ID NO: 104 and a VH of SEQ ID NO:103), CD730008 (i.e., an anti-CD73 antibody comprising a VL of SEQ ID NO: 106 and a VH of SEQ ID NO:107), CD7300011 (i.e., an anti-CD73 antibody comprising a VL of SEQ ID NO: 5 and a VH of SEQ ID NO:6), CD730021 (i.e., an anti-CD73 antibody comprising a VL of SEQ ID NO: 7 and a VH of SEQ ID NO:8), CD730042 (i.e., an anti-CD73 antibody comprising a VL of SEQ ID NO: 9 and a VH of SEQ ID NO:10), CD730046 (i.e., an anti-CD73 antibody comprising a VL of SEQ ID NO: 11 and a VH of SEQ ID NO:12), CD730047 (i.e., an anti-CD73 antibody comprising a VL of SEQ ID NO: 13 and a VH of SEQ ID NO:14), CD730068 (i.e., an anti-CD73 antibody comprising a VL of SEQ ID NO: 108 and a VH of SEQ ID NO:107), or CD730069 (i.e., an anti-CD73 antibody comprising a VL of SEQ ID NO: 110 and a VH of SEQ ID NO:109). The modifications to the parent antibodies can include mutations in the CDR regions and/or in the FW regions as compared to the parent antibody, e.g., CD730004.

In certain aspects, the anti-CD73 antibody comprises modifications to CDR1 and/or CDR2 and/or CDR3 of the light chain of CD730004, CD730008, CD7300011, CD730021, CD730042, CD730046, CD730047, CD730068, or CD730069.

In certain aspects, the anti-CD73 antibody comprises modifications to CDR1 and/or CDR2 and/or CDR3 of the heavy chain of CD730004, CD730008, CD7300011, CD730021, CD730042, CD730046, CD730047, CD730068, or CD730069.

In some aspects, the anti-CD73 antibody or antigen-binding fragment thereof comprises a VL-CDR1 from CD730004, CD730008, CD7300011, CD730021, CD730042, CD730046, CD730047, CD730068, or CD730069. In some aspects, the anti-CD73 antibody or antigen-binding fragment thereof comprises a VL-CDR2 from CD730004, CD730008, CD7300011, CD730021, CD730042, CD730046, CD730047, CD730068, or CD730069. In some aspects, the anti-CD73 antibody or antigen-binding fragment thereof comprises a VL-CDR3 from CD730004, CD730008, CD7300011, CD730021, CD730042, CD730046, CD730047, CD730068, or CD730069.

In some aspects, the anti-CD73 antibody or antigen-binding fragment thereof comprises a VH-CDR1 from CD730004, CD730008, CD7300011, CD730021, CD730042, CD730046, CD730047, CD730068, or CD730069. In some aspects, the anti-CD73 antibody or antigen-binding fragment thereof comprises a VH-CDR2 from CD730004, CD730008, CD7300011, CD730021, CD730042, CD730046, CD730047, CD730068, or CD730069. In some aspects, the anti-CD73 antibody or antigen-binding fragment thereof comprises a VH-CDR3 from CD730004, CD730008, CD7300011, CD730021, CD730042, CD730046, CD730047, CD730068, or CD730069.

In some aspects, the anti-CD73 antibody or antigen-binding fragment thereof comprises a VL-CDR1 from CD730004, CD730008, CD7300011, CD730021, CD730042, CD730046, CD730047, CD730068, or CD730069 except for one, two, three, or four amino acid substitutions. In some aspects, the anti-CD73 antibody or antigen-binding fragment thereof comprises a VL-CDR2 from CD730004, CD730008, CD7300011, CD730021, CD730042, CD730046, CD730047, CD730068, or CD730069, except for one, two, three, or four amino acid substitutions. In some aspects, the anti-CD73 antibody or antigen-binding fragment thereof comprises a VL-CDR3 from CD730004, CD730008, CD7300011, CD730021, CD730042, CD730046, CD730047, CD730068, or CD730069, except for one, two, three or four amino acid substitutions.

In some aspects, the anti-CD73 antibody or antigen-binding fragment thereof comprises a VH-CDR1 from CD730004, CD730008, CD7300011, CD730021, CD730042, CD730046, CD730047, CD730068, or CD730069, except for one, two, three, or four amino acid substitutions. In some aspects, the anti-CD73 antibody or antigen-binding fragment thereof comprises a VH-CDR2 from CD730004, CD730008, CD7300011, CD730021, CD730042, CD730046, CD730047, CD730068, or CD730069, except for one, two, three, or four amino acid substitutions. In some aspects, the anti-CD73 antibody or antigen-binding fragment thereof comprises a VH-CDR3 from CD730004, CD730008, CD7300011, CD730021, CD730042, CD730046, CD730047, CD730068, or CD730069, except for one, two, three or four amino acid substitutions.

In some aspects, the anti-CD73 antibody or antigen-binding fragment thereof comprises a VL-CDR1 from CD730004, CD730008, CD7300011, CD730021, CD730042, CD730046, CD730047, CD730068, or CD730069; a VL-CDR2 from CD730004, CD730008, CD7300011, CD730021, CD730042, CD730046, CD730047, CD730068, or CD730069; and a VL-CDR3 from CD730004, CD730008, CD7300011, CD730021, CD730042, CD730046, CD730047, CD730068, or CD730069.

In some aspects, the anti-CD73 antibody or antigen-binding fragment thereof comprises a VH-CDR1 from CD730004, CD730008, CD7300011, CD730021, CD730042, CD730046, CD730047, CD730068, or CD730069; a VH-CDR2 from CD730004, CD730008, CD7300011, CD730021, CD730042, CD730046, CD730047, CD730068, or CD730069; and a VH-CDR3 from CD730004, CD730008, CD7300011, CD730021, CD730042, CD730046, CD730047, CD730068, or CD730069.

In some aspects, the anti-CD73 antibody or antigen-binding fragment thereof comprises a VL-CDR1 from CD730004, CD730008, CD7300011, CD730021, CD730042, CD730046, CD730047, CD730068, or CD730069, except for one, two, three or four amino acid substitutions; a VL-CDR2 from CD730004, CD730008, CD7300011, CD730021, CD730042, CD730046, CD730047, CD730068, or CD730069, except for one, two, three or four amino acid substitutions; and a VL-CDR3 from CD730004, CD730008, CD7300011, CD730021, CD730042, CD730046, CD730047, CD730068, or CD730069, except for one, two, three or four amino acid substitutions.

In some aspects, the anti-CD73 antibody or antigen-binding fragment thereof comprises a VH-CDR1 from CD730004, CD730008, CD7300011, CD730021, CD730042, CD730046, CD730047, CD730068, or CD730069, except for one, two, three or four amino acid substitutions; a VH-CDR2 from CD730004, CD730008, CD7300011, CD730021, CD730042, CD730046, CD730047, CD730068, or CD730069, except for one, two, three or four amino acid substitutions; and a VH-CDR3 from CD730004, CD730008, CD7300011, CD730021, CD730042, CD730046, CD730047, CD730068, or CD730069, except for one, two, three or four amino acid substitutions.

In certain aspects, the anti-CD73 antibody or antigen-binding fragment thereof comprises modifications to CDR1, and/or CDR2, and/or CDR3 of the heavy and/or light chain from CD730004, CD730008, CD7300011, CD730021, CD730042, CD730046, CD730047, CD730068, or CD730069, and further comprises modifications to FW1, and/or FW2, and/or FW3, and/or FW4 of the heavy and/or light chain from CD730004, CD730008, CD7300011, CD730021, CD730042, CD730046, CD730047, CD730068, or CD730069.

In certain aspects, the anti-CD733 antibody or antigen-binding fragment thereof comprises a VL and a VH comprising VL-CDR1, VL-CRD2, VL-CDR3, VH-CDR1, VH-CDR2, and VH-CDR3 amino acid sequences identical or identical except for one, two, three, or four amino acid substitutions in one or more CDRs, wherein such VL-CDR1, VL-CRD2, VL-CDR3, VH-CDR1, VH-CDR2, and VH-CDR3 are from CD730004, CD730008, CD7300011, CD730021, CD730042, CD730046, CD730047, CD730068, or CD730069.

In certain aspects, the anti-CD73 antibody or antigen-binding fragment thereof comprises an antibody VL and an antibody VH, wherein the VL comprises an amino acid sequence at least about 80%, about 85%, about 90%, about 95%, about 96%, about 97%, about 98%, about 99%, or about 100% identical to a reference amino acid sequence selected from VL sequences from CD730004, CD730008, CD7300011, CD730021, CD730042, CD730046, CD730047, CD730068, or CD730069.

In other aspects, the anti-CD73 antibody or antigen-binding fragment thereof comprises an antibody VL and an antibody VH, wherein the VH comprises an amino acid sequence at least about 80%, about 85%, about 90%, about 95%, about 96%, about 97%, about 98%, about 99%, or about 100% identical to a reference amino acid sequence selected from VH sequences from CD730004, CD730008, CD7300011, CD730021, CD730042, CD730046, CD730047, CD730068, or CD730069.

In other aspects, the anti-CD73 antibody or antigen-binding fragment thereof comprises a VL comprising a sequence at least about 80%, about 85%, about 90%, about 95%, about 96%, about 97%, about 98%, about 99%, or about 100% identical to a reference amino acid sequence selected from VL sequences from CD730004, CD730008, CD7300011, CD730021, CD730042, CD730046, CD730047, CD730068, or CD730069, and further comprises a VH comprising a sequence at least about 80%, about 85%, about 90%, about 95%, about 96%, about 97%, about 98%, about 99%, or about 100% identical to a reference amino acid sequence selected from VH sequences from CD730004, CD730008, CD7300011, CD730021, CD730042, CD730046, CD730047, CD730068, or CD730069.

In certain aspects, the anti-CD73 antibody or antigen-binding fragment thereof disclosed herein binds CD73 with substantially the same or better affinity as a CD730004, CD730008, CD7300011, CD730021, CD730042, CD730046, CD730047, CD730068, or CD730069 antibody.

(iv) Mixed and Matched Anti-CD73 Antibodies

The VH and VL sequences from the anti-CD73 binding molecules disclosed herein (e.g., CD730002, CD730004, CD730008, CD730010, CD730011, CD73021, CD730042, CD730046, CD730047, CD730068, or CD730069) or VH and VL of variants of such sequences (e.g., clone 10 GL9, clone 10 P32E, clone 10 C1, clone 10 C2, clone 10 D3, clone 10 G10, clone 10 HPT, clone 10 GRVE, clone 10 combo1, clone 10 combo2, clone 10 combo3, clone 10 combo5, or clone combo6) can be "mixed and matched" to create other anti-CD73 binding molecules.

In certain aspects, the VH sequences of the 10.3 antibody and the 2C5 antibody are mixed and matched. In another aspect, the VL sequences of the 10.03 antibody and the 2C5 antibody can be mixed and matched. Additionally or alternatively, the VL and/or VH sequences of clone 10 (CD730010) variants disclosed herein can be mixed and matched. Additionally or alternatively, the VL and/or VH sequences of clone 2 (CD730002) variants disclosed herein can be mixed and matched. Additionally or alternatively, the VL and/or VH sequences of clone 10 (CD730010) and clone 2 (CD730002) variants disclosed herein can be mixed and matched.

In some aspects, VL and/or VH mixing and matching can take place between sequences derived from antibodies grouped in the same epitope bin (see Example 2). As used herein, the term "epitope bin" refers to the grouping of antibodies or antigen-binding fragments thereof that bind the same epitope or an overlapping epitope, or compete with each other for binding with the same epitope or overlapping epitope. E.g., sequences from CD730003, CD730010, CD730021, CD730042, CD730046, and CD730047, all of them antibodies belonging to "Epitope Bin B" can be mixed in matched. In other aspects, the VL and/or VH mixing and matching can take place between sequences derived from anti-CD73 antibodies grouped in different epitope bins. Accordingly, sequences from antibodies belonging to "Epitope Bin B" can be mixed and matched with sequences from anti-CD73 antibodies in "Epitope Bin A" (CD730002, CD730004, CD730008, and CD730011) or "Epitope Bin C" (CD730068 and CD730069).

(v) Mutant Anti-CD73 Antibodies

In certain aspects, an anti-CD73 antibody (for example, MEDI9447, a clone 10.3 antibody or a clone 2C5 antibody) or antigen-binding fragment thereof disclosed herein comprises mutations that improve the binding to human FcRn and improve the half-life of the anti-CD73 antibody or antigen-binding fragment thereof. In some aspects, such mutations are a methionine (M) to tyrosine (Y) mutation in position 252, a serine (S) to threonine (T) mutation in position 254, and a threonine (T) to glutamic acid (E) mutation in position 256, numbered according to the EU index as in Kabat (Kabat, et al. (1991) Sequences of Proteins of Immunological Interest, U.S. Public Health Service, National Institutes of Health, Washington, D.C.), introduced into the constant domain of an IgG1. See U.S. Pat. No. 7,658,921, which is incorporated by reference herein. This type of mutant IgG, referred to as a "YTE mutant" has been shown display approximately four-times increased half-life as compared to wild-type versions of the same antibody (Dall'Acqua et al., J. Biol. Chem. 281:23514-24 (2006)). In some aspects, an anti-CD73 antibody or antigen-binding fragment thereof comprising an IgG constant domain comprises one or more amino acid substitutions of amino acid residues at positions 251-257, 285-290, 308-314, 385-389, and 428-436, numbered according to the EU index as in Kabat, wherein such mutations increase the serum half-life of the anti-CD73 antibody or antigen-binding fragment thereof.

In some aspects, a YTE mutant further comprises a substitution at position 434 of the IgG constant domain, numbered according to the EU index as in Kabat, with an amino acid selected from the group consisting of tryptophan (W), methionine (M), tyrosine (Y), and serine (S). In other aspects, a YTE mutant further comprises a substitution at position 434 of the IgG constant domain, numbered according to the EU index as in Kabat, with an amino acid selected from the group consisting of tryptophan (W), methionine (M), tyrosine (Y), and serine (S), and substitution at position 428 of the IgG constant domain, numbered according to the EU index as in Kabat, with an amino acid selected from the group consisting of threonine (T), leucine (L), phenylalanine (F), and serine (S).

In yet other aspect, a YTE mutant further comprises a substitution at position 434 of the IgG constant domain, numbered according to the EU index as in Kabat, with tyrosine (Y), and a substitution at position 257 of the IgG constant domain, numbered according to the EU index as in Kabat, with leucine (L). In some aspects, a YTE mutant further comprises a substitution at position 434 of the IgG constant domain, numbered according to the EU index as in Kabat, with serine (S), and a substitution at position 428 of the IgG constant domain, numbered according to the EU index as in Kabat, with leucine (L).

In a specific aspect, the anti-CD73 antibody (for example, MEDI9447, a clone 10.3 antibody or a clone 2C5 antibody) or antigen-binding fragment thereof disclosed herein comprises an IgG1 constant domain comprising a methionine (M) to tyrosine (Y) mutation in position 252, a serine (S) to threonine (T) mutation in position 254, and a threonine (T) to glutamic acid (E) mutation in position 256 of the IgG1 constant domain, numbered according to the EU index as in Kabat.

In certain aspects, the anti-CD73 antibody (for example, MEDI9447, a clone 10.3 antibody or a clone 2C5 antibody) or antigen-binding fragment thereof disclosed herein comprises at least one IgG constant domain amino acid substitution selected from the group consisting of:

(a) substitution of the amino acid at position 252 with tyrosine (Y), phenylalanine (F), tryptophan (W), or threonine (T);

(b) substitution of the amino acid at position 254 with threonine (T);

(c) substitution of the amino acid at position 256 with serine (S), arginine (R), glutamine (Q), glutamic acid (E), aspartic acid (D), or threonine (T);

(d) substitution of the amino acid at position 257 with leucine (L);

(e) substitution of the amino acid at position 309 with proline (P);

(f) substitution of the amino acid at position 311 with serine (S);

(g) substitution of the amino acid at position 428 with threonine (T), leucine (L), phenylalanine (F), or serine (S);
(h) substitution of the amino acid at position 433 with arginine (R), serine (S), isoleucine (I), proline (P), or glutamine (Q);
(i) substitution of the amino acid at position 434 with tryptophan (W), methionine (M), serine (S), histidine (H), phenylalanine (F), or tyrosine; and,
(j) a combination of two or more of said substitutions, wherein the positions are numbered according to the EU index as in Kabat, and wherein the modified IgG has an increased serum half-life compared to the serum half-life of an IgG having the wild-type IgG constant domain.

In some aspects, the VH and/or VL amino acid sequence of an anti-CD73 antibody (for example, MEDI9447, a clone 10.3 antibody or a clone 2C5 antibody) or antigen-binding fragment thereof disclosed herein can be 85%, 90%, 95%, 96%, 97%, 98% or 99% similar to the VH and VL sequences set forth above, and comprise 1, 2, 3, 4, 5 or more conservative substitutions. A CD73 antibody having VH and VL regions having high (i.e., 80% or greater) sequence similarity or sequence identity to the VH regions of SEQ ID NOs: 71, 72, 73, 74, 75, 76, 77, 78, 79, 80, 81, 82, 83, 84, 85, 87, 111, 113, 114, 115, 116, or 117, and/or VL regions of SEQ ID NOs: 57, 58, 59, 60, 61, 62, 63, 64, 65, 66, 67, 68, 69, 70, 86, 88, 112, 118, 119, 120, or 121 respectively, can be obtained by mutagenesis (e.g., site-directed or PCR-mediated mutagenesis) of nucleic acid molecules encoding SEQ ID NOs: 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 111, 112, 113, 114, 115, 116, 117, 118, 119, 120, or 121, followed by testing of the encoded altered antibody for retained function using the functional assays described herein.

In some aspects, the Fc domain of an anti-CD73 antibody disclosed herein or the Fc domain of a fusion protein comprising a CD73-binding fragment of an antibody disclosed herein has reduced binding to an Fc receptor to reduce cytotoxicity, e.g., via ADCC. In some aspects, the Fc domain of the antibody or Fc fusion protein has increased binding to an Fc receptor to increase cytotoxicity, e.g., via ADCC. In some aspects, the Fc domain of the antibody or Fc fusion protein comprises a non-naturally occurring ADCC reducing amino acid residue at one or more positions selected from the group consisting of 234, 235, 236, 237, 238, 239, 240, 241, 243, 244, 245, 247, 251, 252, 254, 255, 256, 262, 263, 264, 265, 266, 267, 269, 279, 280, 284, 292, 296, 297, 298, 299, 305, 313, 316, 325, 326, 327, 328, 329, 330, 331, 332, 333, 334, 339, 341, 343, 370, 373, 378, 392, 416, 419, 421, 440, and 443 as numbered by the EU index as set forth in Kabat. Numerous specific mutations capable of reducing the ADCC activity of an antibody are known in the art and include, for example 234F, 235E, 235F, 235Q (or 235Y), 239A, 332Q, 331S and combinations thereof. For example, see the mutations described in International Publication Nos. WO8807089, WO9958572, WO9951642, WO2012175751, WO2011149999, WO2011066501, WO2000042072, WO2011120134, which are herein incorporated by reference in their entireties. Antibodies with reduced ADCC effector function also include those with substitution of one or more of Fc region residues 238, 265, 269, 270, 297, 327, and 329 (see, e.g., U.S. Pat. No. 6,737,056). Such Fc mutants also include Fc mutants with substitutions at two or more of amino acid positions 265, 269, 270, 297 and 327, including Fc mutant with substitution of residues 265 and 297 to alanine (see, e.g., U.S. Pat. No. 7,332,581). Optionally, mutations which reduce both ADCC and CDC can be incorporated. In some aspects, anti-CD73 antibodies disclosed herein or antigen-binding fragment thereof comprising mutations that reduce or abolish ADCC and/or CDC can be used to generate antibody drug conjugates (ADC).

In one aspect, the present disclosure provides an anti-CD73 antibody, wherein the antibody is an IgG1, IgG2 or IgG3 and comprises at least one modification at one or more positions selected from the group consisting of 234, 235, and 331 as numbered by the EU index as set forth in Kabat. In still another specific aspect, the Fc region is an IgG1, IgG2 or IgG3 Fc region and the non-naturally occurring amino acids are selected from the group consisting of 234F, 235E, 235F, 235Q (or 235Y), 239A, 332Q, 331S, 332Q as numbered by the EU index as set forth in Kabat.

In another aspect, the present disclosure provides an anti-CD73 antibody, wherein the antibody is an IgG4 and comprises at least one modification at one or more positions selected from the group consisting of 228 and 235 as numbered by the EU index as set forth in Kabat. In still another specific aspect, the Fc region is an IgG4 Fc region and the non-naturally occurring amino acids are selected from the group consisting of 228P, 235E and 235Y as numbered by the EU index as set forth in Kabat. In specific aspects, the present disclosure provides an anti-CD73 antibody, wherein the antibody is an IgG1, IgG2, or IgG3 and comprises modifications at positions (i) 234F, 235E, and 331S; (ii) 234F, 235F, and 331S; (iii) 234F, 235Q, and 322Q. In another specific aspect, the present disclosure provides an anti-CD73 antibody, wherein the antibody is an IgG4 and comprises modifications 228P and 235E.

III. Epitope-Competing CD73-Binding Molecules

In another aspect, the present disclosure provides CD73-binding molecules that bind to the same epitope as do the various anti-CD73 antibodies described herein, for example, molecules that bind to the same epitope as MEDI9447, a clone 10.3 antibody or to the same epitope as a clone 2C5 antibody.

Such antibodies can be identified based on their ability to cross-compete (e.g., to competitively inhibit the binding of, in a statistically significant manner) with the anti-CD73 antibodies disclosed herein, such as the CD730010 antibody, CD730002 antibody, CD730004 antibody, and antigen-binding fragments thereof, in standard CD73 binding assays (e.g., flow cytometry assays, surface plasmon resonance, or solution assays).

Accordingly, in one aspect, the present disclosure provides anti-CD73 antibodies and antigen-binding fragments thereof, e.g., human monoclonal antibodies, that compete for binding to CD73 with another anti-CD73 antibody or antigen-binding fragment thereof, such as the CD730010 antibody, CD730002 antibody, CD730004 antibody, variants thereof (e.g., MEDI9447, a clone 10.3 antibody or a clone 2C5 antibody), or antigen-binding fragments thereof. The ability of a test antibody to inhibit the binding of, e.g., the CD730010 antibody (or a clone 10.3 antibody or an antigen-binding fragment thereof), or the CD730002 antibody (or clone 2C5 antibody or an antigen-binding fragment thereof) demonstrates that the test antibody can compete with that antibody for binding to CD73; such antibody can, according to non-limiting theory, bind to the same or a related (e.g., a structurally similar or spatially proximal) epitope on CD73 as the anti-CD73 antibody or antigen-binding fragment thereof with which it competes. In one aspect, the anti-CD73 antibody or antigen-binding fragment thereof that binds to the same epitope on CD73 as, e.g., the CD730010 antibody (or a clone 10.3 antibody or an antigen-binding fragment thereof), or the CD730002 antibody (or clone 2C5 antibody or an antigen-binding fragment thereof), is a human monoclonal antibody.

IV. Functional Characteristics of Anti-CD73 Antibodies

The affinity or avidity of an antibody for an antigen can be determined experimentally using any suitable method well known in the art, e.g., flow cytometry, enzyme-linked immunosorbent assay (ELISA), or radioimmunoassay (MA), or kinetics (e.g., BIACORE™ analysis). Direct binding assays as well as competitive binding assay formats can be readily employed. (See, for example, Berzofsky et al., "Antibody-Antigen Interactions," In Fundamental Immunology, Paul, W. E., Ed., Raven Press: New York, N.Y. (1984); Kuby, Immunology, W. H. Freeman and Company: New York, N.Y. (1992); and methods described herein. The measured affinity of a particular antibody-antigen interaction can vary if measured under different conditions (e.g., salt concentration, pH, temperature). Thus, measurements of affinity and other antigen-binding parameters (e.g., $K_D$ or $K_d$, $K_{on}$, $K_{off}$) are made with standardized solutions of antibody and antigen, and a standardized buffer, as known in the art and such as the buffer described herein.

It also known in the art that affinities measured using surface plasmon resonance analysis (e.g., BIACORE™) can vary depending on which one of the reactants is bound to the chip. In this respect, affinity can be measured using a format in which the targeting antibody (e.g., a clone 10.3 antibody or a clone 2C5 antibody) is immobilized onto the chip (referred to as an "IgG down" format) or using a format in which the target protein (e.g., CD73) is immobilized onto the chip (referred to as, e.g., a "CD73 down" format).

In one aspect of the present disclosure, the anti-CD73 antibody (for example, MEDI9447, a clone 10.3 antibody or a clone 2C5 antibody) or an antigen-binding fragment thereof specifically binds CD73 and/or antigenic fragments thereof with a dissociation constant or $k_d$ ($k_{off}/k_{on}$) of less than $10^{-6}$ M, or of less than $10^{-7}$ M, or of less than $10^{-8}$ M, or of less than $10^{-9}$ M, or of less than $10^{-10}$ M, or of less than $10^{-11}$ M, or of less than $10^{-12}$ M, or of less than $10^{-13}$ M.

In another aspect, the anti-CD73 antibody (for example, MEDI9447, a clone 10.3 antibody or a clone 2C5 antibody) or an antigen-binding fragment thereof binds to CD73 and/or antigenic fragments thereof with a $K_{off}$ of less than $1 \times 10^{-3}$ s$^{-1}$, or less than $2 \times 10^{-3}$ s$^{-1}$. In other aspects, an anti-CD73 antibody or an antigen-binding fragment thereof binds to CD73 and antigenic fragments thereof with a $K_{off}$ of less than $10^{-3}$ s$^{-1}$, less than $5 \times 10^{-3}$ s$^{-1}$, less than $10^{-4}$ s$^{-1}$, less than $5 \times 10^{-4}$ s$^{-1}$, less than $10^{-5}$ s$^{-1}$, less than $5 \times 10^{-5}$ s$^{-1}$, less than $10^{-6}$ s$^{-1}$, less than $5 \times 10^{-6}$ s$^{-1}$, less than less than $5 \times 10^{-7}$ s$^{-1}$, less than $10^{-8}$ s$^{-1}$, less than $5 \times 10^{-8}$ s$^{-1}$, less than $10^{-9}$ s$^{-1}$, less than $5 \times 10^{-9}$ s$^{-1}$, or less than $10^{-10}$ s$^{-1}$.

In another aspect, the anti-CD73 antibody (for example, a clone 10.3 antibody or a clone 2C5 antibody) or an antigen-binding fragment thereof binds to CD73 and/or antigenic fragments thereof with an association rate constant or km rate of at least $10^5$ M$^{-1}$ s$^{-1}$, at least $5 \times 10^5$ M$^{-1}$ s$^{-1}$, at least $10^6$ M$^{-1}$ s$^{-1}$ at least $5 \times 10^6$ M$^{-1}$ s$^{-1}$, at least $10^7$ M$^{-1}$ s$^{-1}$ at least $5 \times 10^7$ M$^{-1}$ s$^{-1}$, or at least $10^8$ M$^{-1}$ s$^{-1}$, or at least $10^9$ M$^{-1}$ s$^{-1}$.

In some aspects, the anti-CD73 antibody (for example, a clone 10.3 antibody or a clone 2C5 antibody) or an antigen-binding fragment thereof binds to CD73 on the surface of MB-MDA-231 cells with a $K_D$ of at least about 60 pM, at least about 70 pM, at least about 80 pM, at least about 90 pM, at least about 100 pM, at least about 110 pM, at least about 120 pM, at least about 130 pM, at least about 140 pM, at least about 150 pM, at least about 160 pM, or at least about 170 pm, as measured by flow cytometry. In one specific aspect, the anti-CD73 antibody is a clone 10.3 antibody and it binds to CD73 on the surface of MB-MDA-231 cells with a $K_D$ of about 150 pM as measured by flow cytometry. In another specific aspect, the anti-CD73 antibody is a clone 2C5 antibody and it binds to CD73 on the surface of MB-MDA-231 cells with a $K_D$ of about 80 pM as measured by flow cytometry.

In some aspects, the anti-CD73 antibody (for example, MEDI9447, a clone 10.3 antibody or a clone 2C5 antibody) or an antigen-binding fragment thereof binds to CD73 binds on the surface of murine 3T1 cells with a $K_D$ of a of at least about 40 pM, at least about 50 pM, at least about 60 pM, at least about 70 pM, at least about 80 pM, at least about 90 pM, at least about 100 pM, at least about 120 pM, or at least about 130 pM, as measured by flow cytometry. In one specific aspect, the anti-CD73 antibody is a clone 10.3 antibody and it binds to CD73 on the surface of murine 3T1 cells with a $K_D$ of about 110 pM as measured by flow cytometry. In another specific aspect, the anti-CD73 antibody is a clone 2C5 antibody and it binds to CD73 on the surface of murine 3T1 cells with a $K_D$ of about 55 pM as measured by flow cytometry.

In some aspects, the anti-CD73 antibody (for example, MEDI9447, a clone 10.3 antibody or a clone 2C5 antibody) or an antigen-binding fragment thereof binds to CD73 on the surface of cynomolgus MK-1 cells with a $K_D$ of a of at least about 40 pM, at least about 50 pM, at least about 60 pM, at least about 70 pM, at least about 80 pM, at least about 90 pM, or at least about 100 pM, as measured by flow cytometry. In one specific aspect, the anti-CD73 antibody is a clone 10.3 antibody and it binds to CD73 on the surface of cynomolgus MK-1 cells with a $K_D$ of about 80 pM as measured by flow cytometry. In another specific aspect, the anti-CD73 antibody is a clone 2C5 antibody and it binds to CD73 on the surface of cynomolgus MK-1 cells with a $K_D$ of about 60 pM as measured by flow cytometry.

In some aspects, the anti-CD73 antibody (for example, MEDI9447, a clone 10.3 antibody or a clone 2C5 antibody) or an antigen-binding fragment thereof binds to human CD73 with a $K_D$ of a of at least about 3 pM, at least about 4 pM, at least about 5 pM, at least about 6 pM, at least about 7 pM, at least about 8 pM, at least about 9 pM, or at least about 10 pM, as measured by surface plasmon resonance (PROTEON®). In one specific aspect, the anti-CD73 antibody is a clone 10.3 antibody and it binds to human CD73 with a $K_D$ of about 4 pM as measured by surface plasmon resonance (PROTEON®). In another specific aspect, the anti-CD73 antibody is a clone 2C5 antibody and it binds to human CD73 with a $K_D$ of about 9 pM as measured by surface plasmon resonance (PROTEON®).

In some aspects, the anti-CD73 antibody (for example, MEDI9447, a clone 10.3 antibody or a clone 2C5 antibody) or an antigen-binding fragment thereof disclosed herein binds to murine CD73 with a $K_D$ of a of at least about 1 pM, at least about 2 pM, at least about 3 pM, at least about 4 pM, at least about 5 pM, at least about 6 pM, at least about 7 pM, at least about 8 pM, at least about 9 pM, at least about 10 pM, at least about 11 pM, at least about 12 pM, at least about 13 pM, at least about 14 pM, at least about 15 pM, at least about 16 pM, at least about 17 pM, at least about 18 pM, at least about 19 pM, at least about 20 pM, at least about 21 pM, at least about 22 pM, at least about 23 pM, at least about 24 pM, or at least about 25 pM, as measured by surface plasmon resonance (PROTEON®). In one specific aspect, the anti-CD73 antibody is a clone 10.3 antibody and it binds to murine CD73 with a $K_D$ of about 1 pM as measured by surface plasmon resonance (PROTEON®). In another specific aspect, the anti-CD73 antibody is a clone 2C5 antibody and it binds to murine CD73 with a $K_D$ of about 22 pM as measured by surface plasmon resonance (PROTEON®).

In some aspects, an anti-CD73 antibody (for example, MEDI9447, a clone 10.3 antibody or a clone 2C5 antibody) or an antigen-binding fragment thereof binds to cynomolgus CD73 with a $K_D$ of a of at least about 3 pM, at least about 4 pM, at least about 5 pM, at least about 6 pM, at least about 7 pM, at least about 8 pM, at least about 9 pM, or at least about 10 pM, as measured by surface plasmon resonance (PROTEON®). In one specific aspect, the anti-CD73 antibody is a clone 10.3 antibody and it binds to cynomolgus CD73 with a $K_D$ of about 7 pM as measured by SPR (PROTEON®). In another specific aspect, the anti-CD73 antibody is a clone 2C5 antibody and it binds to cynomolgus CD73 with a $K_D$ of about 9 pM as measured by surface plasmon resonance (PROTEON®).

In some aspects, the anti-CD73 antibody (for example, MEDI9447, a clone 10.3 antibody or a clone 2C5 antibody) or an antigen-binding fragment thereof binds to human CD73 with a $K_D$ of a of at least about 40 pM, at least about 50 pM, at least about 60 pM, at least about 70 pM, at least about 80 pM, at least about 90 pM, at least about 100 pM, or at least about 110 pM, as measured by solution binding. In one specific aspect, the anti-CD73 antibody is a clone 10.3 antibody and it binds to human CD73 with a $K_D$ of about 80 pM as measured by solution binding. In another specific aspect, the anti-CD73 antibody is a clone 2C5 antibody and it binds to human CD73 with a $K_D$ of about 80 pM as measured by solution binding.

In some aspects, the anti-CD73 antibody (for example, a clone 10.3 antibody or a clone 2C5 antibody) or an antigen-binding fragment thereof binds to murine CD73 with a $K_D$ of a of at least about 100 pM, at least about 200 pM, at least about 300 pM, at least about 400 pM, at least about 500 pM, at least about 600 pM, at least about 700 pM, at least about 800 pM, at least about 900 pM, at least about 1000 pM, at least about 1100 pM, at least about 1200 pM, at least about 1300 pM, at least about 1400 pM, at least about 1500 pM, at least about 1600 pM, at least about, or at least about 1700 pM, as measured by solution binding. In one specific aspect, the anti-CD73 antibody is a clone 10.3 antibody and it binds to murine CD73 with a $K_D$ of about 130 pM as measured by solution binding. In another specific aspect, the anti-CD73 antibody is a clone 2C5 antibody and it binds to murine CD73 with a $K_D$ of about 1500 pM as measured by solution binding.

In some aspects, the anti-CD73 antibody (for example, a clone 10.3 antibody or a clone 2C5 antibody) or an antigen-binding fragment thereof binds to cynomolgus CD73 with a $K_D$ of a of at least about 60 pM, at least about 70 pM, at least about 80 pM, at least about 90 pM, at least about 100 pM, at least about 110 pM, or at least about 120 pM, as measured by solution binding. In one specific aspect, the anti-CD73 antibody is a clone 10.3 antibody and it binds to cynomolgus CD73 with a $K_D$ of about 90 pM as measured by solution binding. In another specific aspect, the anti-CD73 antibody is a clone 2C5 antibody and it binds to cynomolgus CD73 with a $K_D$ of about 100 pM as measured by solution binding.

In particular aspect, MEDI9447 binds CD73 with a $K_D$ of about $1 \times 10^{-12}$, $5 \times 10^{-12}$, $10 \times 10^{-12}$, $100 \times 10^{-12}$, or $150 \times 10^{-12}$.

In some aspects, a CD73-binding molecule disclosed herein, e.g., an anti-CD73 antibody (for example, MEDI9447, a clone 10.3 antibody or a clone 2C5 antibody) or an antigen-binding fragment thereof can relieve AMP-mediated suppression of T cell division. In other aspects, a CD73-binding molecule disclosed herein, e.g., an anti-CD73 antibody (for example, MEDI9447, a clone 10.3 antibody or a clone 2C5 antibody) or an antigen-binding fragment thereof can rescue ATP-induced $T_{eff}$ suppression by $T_{reg}$.

In some aspects, a CD73-binding molecule disclosed herein, e.g., an anti-CD73 antibody or antigen-binding fragment thereof (for example, a clone 10.3 antibody or a clone 2C5 antibody) can significantly inhibit syngeneic tumor growth. In one aspect, the tumor is a CT26 mouse syngeneic CRC tumor. In some aspects, a CD73-binding molecule, e.g., an anti-CD73 antibody or antigen-binding fragment thereof disclosed herein (for example, a clone 10.3 antibody or a clone 2C5 antibody) can significantly inhibit tumor growth, wherein the tumor is unresponsive to therapy with anti-PD1.

In some aspects, a CD73-binding molecule disclosed herein, e.g., an anti-CD73 antibody or antigen-binding fragment thereof (for example, a clone 10.3 antibody or a clone 2C5 antibody) can be internalized after binding to cells. In some aspects, the CD73-binding molecule is an antibody drug conjugate (ADC).

V. Preparation of Anti-CD73 Antibodies and Antigen-Binding Fragments

Monoclonal anti-CD73 antibodies (e.g., MEDI9447, a clone 10.3 antibody or a clone 2C5 antibody) and antigen-binding fragments thereof can be prepared using hybridoma methods, such as those described by Kohler and Milstein (1975) Nature 256:495. Using the hybridoma method, a mouse, hamster, or other appropriate host animal, is immunized as described above to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g. radioimmunoassay (MA); enzyme-linked immunosorbent assay (ELISA)) can then be propagated either in in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

Alternatively anti-CD73 monoclonal antibodies (for example, MEDI9447, a clone 10.3 antibody or a clone 2C5 antibody) and antigen-binding fragments thereof can also be made using recombinant DNA methods as described, for example, in U.S. Pat. No. 4,816,567. The polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, monoclonal antibodies are generated by the host cells. Also, recombinant anti-CD73 monoclonal antibodies or antigen-binding fragments thereof of the desired species can be isolated from phage display libraries expressing CDRs of the desired species as described (McCafferty et al., 1990, Nature, 348:552-554; Clarkson et al., 1991, Nature, 352:624-628; and Marks et al., 1991, J. Mol. Biol., 222:581-597).

The polynucleotide(s) encoding an anti-CD73 antibody (for example, a clone 10.3 antibody or a clone 2C5 antibody) or antigen-binding fragment thereof can further be modified in a number of different manners using recombinant DNA technology to generate alternative antibodies. In some aspects, the constant domains of the light and heavy chains of, for example, a mouse monoclonal antibody can be substituted (1) for those regions of, for example, a human antibody to generate a chimeric antibody or (2) for a non-immunoglobulin polypeptide to generate a fusion antibody. In some aspects, the constant regions are truncated or removed to generate the desired antibody fragment of a monoclonal antibody. Site-directed or high-density mutagenesis of the variable region can be used to optimize specificity, affinity, etc. of a monoclonal antibody.

In certain aspects, the anti-CD73 antibody (for example, a clone 10.3 antibody or a clone 2C5 antibody) or antigen-binding fragment thereof is a human antibody or antigen-binding fragment thereof. Human antibodies can be directly prepared using various techniques known in the art. Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boemer et al., 1991, J. Immunol., 147 (1):86-95; and U.S. Pat. No. 5,750,373).

Also, the anti-CD73 human antibody (for example, a clone 10.3 antibody or a clone 2C5 antibody) or antigen-binding fragment thereof can be selected from a phage library, where that phage library expresses human antibodies, as described, for example, in Vaughan et al., 1996, Nat. Biotech., 14:309-314, Sheets et al., 1998, Proc. Nat'l. Acad. Sci., 95:6157-6162, Hoogenboom and Winter, 1991, J. Mol. Biol., 227:381, and Marks et al., 1991, J. Mol. Biol., 222:581). Techniques for the generation and use of antibody phage libraries are also described in U.S. Pat. Nos. 5,969,108, 6,172,197, 5,885,793, 6,521,404; 6,544,731; 6,555,313; 6,582,915; 6,593,081; 6,300,064; 6,653,068; 6,706,484; and 7,264,963; and Rothe et al., 2007, J. Mol. Bio., doi:10.1016/j.jmb.2007.12.018 (each of which is incorporated by reference in its entirety).

Affinity maturation strategies and chain shuffling strategies (Marks et al., 1992, Bio/Technology 10:779-783, incorporated by reference in its entirety) are known in the art and can be employed to generate high affinity human antibodies or antigen-binding fragments thereof.

In some aspects, the anti-CD73 monoclonal antibody (for example, a clone 10.3 antibody or a clone 2C5 antibody) can be a humanized antibody. Methods for engineering, humanizing or resurfacing non-human or human antibodies can also be used and are well known in the art. A humanized, resurfaced or similarly engineered antibody can have one or more amino acid residues from a source that is non-human, e.g., but not limited to, mouse, rat, rabbit, non-human primate or other mammal. These non-human amino acid residues are replaced by residues that are often referred to as "import" residues, which are typically taken from an "import" variable, constant or other domain of a known human sequence. Such imported sequences can be used to reduce immunogenicity or reduce, enhance or modify binding, affinity, on-rate, off-rate, avidity, specificity, half-life, or any other suitable characteristic, as known in the art. In general, the CDR residues are directly and most substantially involved in influencing CD73 binding. Accordingly, part or all of the non-human or human CDR sequences are maintained while the non-human sequences of the variable and constant regions can be replaced with human or other amino acids.

Antibodies can also optionally be humanized, resurfaced, engineered or human antibodies engineered with retention of high affinity for the CD73 antigen and other favorable biological properties. To achieve this goal, humanized (or human) or engineered anti-CD73 antibodies and resurfaced antibodies can be optionally prepared by a process of analysis of the parental sequences and various conceptual humanized and engineered products using three-dimensional models of the parental, engineered, and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen, such as CD73. In this way, framework (FW) residues can be selected and combined from the consensus and import sequences so that the desired antibody characteristic, such as increased affinity for the target antigen(s), is achieved.

Humanization, resurfacing or engineering of anti-CD73 antibodies (for example, a clone 10.3 antibody or a clone 2C5 antibody) or antigen-binding fragments thereof can be performed using any known method, such as but not limited to those described in, Jones et al., Nature 321:522 (1986); Riechmann et al., Nature 332:323 (1988); Verhoeyen et al., Science 239:1534 (1988)), Sims et al., J. Immunol. 151:2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,639,641, 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; 4,816,567, 7,557,189; 7,538,195; and 7,342,110; International Application Nos. PCT/US98/16280; PCT/US96/18978; PCT/US91/09630; PCT/US91/05939; PCT/US94/01234; PCT/GB89/01334; PCT/GB91/01134; PCT/GB92/01755; International Patent Application Publication Nos. WO90/14443; WO90/14424; WO90/14430; and European Patent Publication No. EP 229246; each of which is entirely incorporated herein by reference, including the references cited therein.

Anti-CD73 humanized antibodies and antigen-binding fragments thereof can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

In certain aspects an anti-CD73 antibody fragment (for example, a fragment from a clone 10.3 antibody or from a clone 2C5 antibody) is provided. Various techniques are known for the production of antibody fragments. Traditionally, these fragments are derived via proteolytic digestion of intact antibodies (for example Morimoto et al., 1993, Journal of Biochemical and Biophysical Methods 24:107-117; Brennan et al., 1985, Science, 229:81). In certain aspects, anti-CD73 antibody fragments are produced recombinantly. Fab, Fv, and scFv antibody fragments can all be expressed in and secreted from E. coli or other host cells, thus allowing the production of large amounts of these fragments. Such anti-CD73 antibody fragments can also be isolated from the antibody phage libraries discussed above. The anti-CD73 antibody fragments can also be linear antibodies as described in U.S. Pat. No. 5,641,870. Other techniques for the production of antibody fragments, e.g., chemical synthesis, will be apparent to the skilled practitioner.

According to the present disclosure, techniques can be adapted for the production of single-chain antibodies specific to CD73 (see, e.g., U.S. Pat. No. 4,946,778). In addition, methods can be adapted for the construction of Fab expression libraries (see, e.g., Huse et al., Science 246:1275-1281 (1989)) to allow rapid and effective identification of monoclonal Fab fragments with the desired specificity for CD73, or derivatives, fragments, analogs or homologs thereof. Antibody fragments can be produced by techniques in the art including, but not limited to: (a) a F(ab')2 fragment produced by pepsin digestion of an antibody molecule; (b) a Fab fragment generated by reducing the disulfide bridges of an F(ab')2 fragment, (c) a Fab fragment generated by the treatment of the antibody molecule with papain and a reducing agent, and (d) Fv fragments.

An anti-CD73 antibody (for example, a clone 10.3 antibody or a clone 2C5 antibody) or an antigen-binding fragment thereof disclosed herein can be modified in order to increase its serum half-life. This can be achieved, for example, by incorporation of a salvage receptor binding epitope into the antibody or antibody fragment by mutation of the appropriate region in the antibody or antibody fragment or by incorporating the epitope into a peptide tag that is then fused to the antibody or antibody fragment at either end or in the middle (e.g., by DNA or peptide synthesis), or by YTE mutation. Other methods to increase the serum half-life of an antibody or antigen-binding fragment thereof, e.g., conjugation to a heterologous molecule such as PEG are known in the art.

Heteroconjugate anti-CD73 antibodies (for example, a clone 10.3 antibody or a clone 2C5 antibody) and antigen-binding fragments thereof are also within the scope of the present disclosure. Heteroconjugate antibodies are composed of two covalently joined antibodies. Such antibodies have, for example, been proposed to target immune cells to unwanted cells (see, e.g., U.S. Pat. No. 4,676,980). It is contemplated that the heteroconjugate anti-CD73 antibodies (for example, a clone 10.3 antibody or a clone 2C5 antibody) and antigen-binding fragments thereof can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

For the purposes of the present disclosure, it should be appreciated that modified anti-CD73 antibodies or antigen-binding fragments thereof can comprise any type of variable region that provides for the association of the antibody or polypeptide with CD73. In this regard, the variable region can comprise or be derived from any type of mammal that can be induced to mount a humoral response and generate immunoglobulins against the desired tumor associated antigen. As such, the variable region of the modified anti-CD73 antibodies or antigen-binding fragments thereof can be, for example, of human, murine, non-human primate (e.g., cynomolgus monkeys, macaques, etc.) or lupine origin. In some aspects both the variable and constant regions of the modified anti-CD73 antibodies or antigen-binding fragments thereof are human. In other aspects the variable regions of compatible antibodies (usually derived from a non-human source) can be engineered or specifically tailored to improve the binding properties or reduce the immunogenicity of the molecule. In this respect, variable regions can be humanized or otherwise altered through the inclusion of imported amino acid sequences.

In certain aspects, the variable domains in both the heavy and light chains of an anti-CD73 antibody (for example, a clone 10.3 antibody or a clone 2C5 antibody) or antigen-binding fragment thereof are altered by at least partial replacement of one or more CDRs and, if necessary, by partial framework region replacement and sequence changing. Although the CDRs can be derived from an antibody of the same class or even subclass as the antibody from which the framework regions are derived, it is envisaged that the CDRs will be derived from an antibody of different class and in certain aspects from an antibody from a different species. It is not necessary to replace all of the CDRs with the complete CDRs from the donor variable region to transfer the antigen-binding capacity of one variable domain to another. Rather, it is only necessary to transfer those residues that are necessary to maintain the activity of the antigen-binding site. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antibody with reduced immunogenicity.

Alterations to the variable region notwithstanding, those skilled in the art will appreciate that the modified anti-CD73 antibodies (for example, a modified clone 10.3 antibody or a modified clone 2C5 antibody) or antigen-binding fragments thereof will comprise antibodies (e.g., full-length antibodies or immunoreactive fragments thereof) in which at least a fraction of one or more of the constant region domains has been deleted or otherwise altered so as to provide desired biochemical characteristics such as increased tumor localization or reduced serum half-life when compared with an antibody of approximately the same immunogenicity comprising a native or unaltered constant region. In some aspects, the constant region of the modified antibodies will comprise a human constant region. Modifications to the constant region compatible with this the anti-CD73 molecules disclosed herein comprise additions, deletions or substitutions of one or more amino acids in one or more domains. That is, the modified antibodies disclosed herein can comprise alterations or modifications to one or more of the three heavy chain constant domains ($CH_1$, CH2 or CH3) and/or to the light chain constant domain (CL). In some aspects, modified constant regions wherein one or more domains are partially or entirely deleted are contemplated. In some aspects, the modified antibodies will comprise domain deleted constructs or variants wherein the entire CH2 domain has been removed (ΔCH2 constructs). In some aspects, the omitted constant region domain will be replaced by a short amino acid spacer (e.g., 10 residues) that provides some of the molecular flexibility typically imparted by the absent constant region.

Besides their configuration, it is known in the art that the constant region mediates several effector functions. For example, binding of the C1 component of complement to antibodies activates the complement system. Activation of complement is important in the opsonisation and lysis of cell pathogens. The activation of complement also stimulates the inflammatory response and can also be involved in autoimmune hypersensitivity. Further, antibodies bind to cells via the Fc region, with a Fc receptor site on the antibody Fc region binding to a Fc receptor (FcR) on a cell. There are a number of Fc receptors which are specific for different classes of antibody, including IgG (gamma receptors), IgE (eta receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

In certain aspects, the anti-CD73 antibody (for example, a clone 10.3 antibody or a clone 2C5 antibody) or an antigen-binding fragment thereof provides for altered effector functions that, in turn, affect the biological profile of the administered antibody or antigen-binding fragment thereof. For example, the deletion or inactivation (through point mutations or other means) of a constant region domain can reduce Fc receptor binding of the circulating modified antibody thereby increasing tumor localization. In other cases it can be that constant region modifications, consistent with this disclosure, moderate complement binding and thus reduce the serum half-life and nonspecific association of a conjugated cytotoxin. Yet other modifications of the constant region can be used to eliminate disulfide linkages or oligosaccharide moieties that allow for enhanced localization due to increased antigen specificity or antibody flexibility. Similarly, modifications to the constant region in accordance with this disclosure can easily be made using well known biochemical or molecular engineering techniques well within the purview of the skilled artisan.

In certain aspects, a CD73-binding molecule disclosed herein that is an antibody (for example, a clone 10.3 antibody or a clone 2C5 antibody) or antigen-binding fragment thereof does not have one or more effector functions. For instance, in some aspects, the antibody or antigen-binding fragment thereof has no antibody-dependent cellular cytotoxicity (ADCC) activity and/or no complement-dependent cytotoxicity (CDC) activity. In certain aspects, the anti-CD73 antibody or antigen-binding fragment thereof does not bind to an Fc receptor and/or complement factors. In certain aspects, the antibody or antigen-binding fragment thereof has no effector function.

It will be noted that in certain aspects, the anti-CD73 modified antibodies or antigen-binding fragments thereof can be engineered to fuse the CH3 domain directly to the hinge region of the respective modified antibodies or fragments thereof. In other constructs it can be desirable to provide a peptide spacer between the hinge region and the modified CH2 and/or CH3 domains. For example, compatible constructs could be expressed wherein the CH2 domain has been deleted and the remaining CH3 domain (modified or unmodified) is joined to the hinge region with a 5-20 amino acid spacer. Such a spacer can be added, for instance, to ensure that the regulatory elements of the constant domain remain free and accessible or that the hinge region remains flexible. However, it should be noted that amino acid spacers can, in some cases, prove to be immunogenic and elicit an unwanted immune response against the construct. Accordingly, in certain aspects, any spacer added to the construct will be relatively non-immunogenic, or even omitted altogether, so as to maintain the desired biochemical qualities of the modified antibodies.

Besides the deletion of whole constant region domains, it will be appreciated that the anti-CD73 antibodies and antigen-binding fragments thereof of the present disclosure can be provided by the partial deletion or substitution of a few or even a single amino acid. For example, the mutation of a single amino acid in selected areas of the CH2 domain can be enough to substantially reduce Fc binding and thereby increase tumor localization. Similarly, it can be desirable to simply delete that part of one or more constant region domains that control the effector function (e.g., complement C1Q binding) to be modulated. Such partial deletions of the constant regions can improve selected characteristics of the antibody or antigen-binding fragment thereof (e.g., serum half-life) while leaving other desirable functions associated with the subject constant region domain intact. Moreover, as alluded to above, the constant regions of the disclosed anti-CD73 antibodies and antigen-binding fragments thereof can be modified through the mutation or substitution of one or more amino acids that enhances the profile of the resulting construct. In this respect it is possible to disrupt the activity provided by a conserved binding site (e.g., Fc binding) while substantially maintaining the configuration and immunogenic profile of the modified antibody or antigen-binding fragment thereof. Certain aspects can comprise the addition of one or more amino acids to the constant region to enhance desirable characteristics such as decreasing or increasing effector function or provide for more cytotoxin or carbohydrate attachment. In such aspects it can be desirable to insert or replicate specific sequences derived from selected constant region domains.

The present disclosure also provides variants and equivalents which are substantially homologous to the chimeric, humanized and human anti-CD73 antibodies, or antigen-binding fragments thereof, set forth herein. These can contain, for example, conservative substitution mutations, i.e., the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

An anti-CD73 antibody or antigen-binding fragment thereof can be further modified to contain additional chemical moieties not normally part of the protein. Those derivatized moieties can improve the solubility, the biological half-life or absorption of the protein. The moieties can also reduce or eliminate any desirable side effects of the proteins and the like. An overview for those moieties can be found in Remington's Pharmaceutical Sciences, 20th ed., Mack Publishing Co., Easton, Pa. (2000).

VI. Polynucleotides Encoding CD73-Binding Molecules

In certain aspects, the present disclosure encompasses polynucleotides comprising nucleic acid sequences that encode a polypeptide that specifically binds CD73 or an antigen-binding fragment thereof. For example, the present disclosure provides a polynucleotide comprising a nucleic acid sequence that encodes an anti-CD73 antibody (e.g., a clone 10.3 antibody or a clone 2C5 antibody) or encodes an antigen-binding fragment of such an antibody. The polynucleotides of the present disclosure can be in the form of RNA or in the form of DNA. DNA includes cDNA, genomic DNA, and synthetic DNA; and can be double-stranded or single-stranded, and if single stranded can be the coding strand or non-coding (anti-sense) strand.

In certain aspects, the polynucleotides are isolated. In certain aspects, the polynucleotides are substantially pure. In certain aspects the polynucleotides comprise the coding sequence for the mature polypeptide fused in the same reading frame to a polynucleotide which aids, for example, in expression and secretion of a polypeptide from a host cell (e.g., a leader sequence which functions as a secretory sequence for controlling transport of a polypeptide from the cell). The polypeptide having a leader sequence is a preprotein and can have the leader sequence cleaved by the host cell to form the mature form of the polypeptide. The polynucleotides can also encode for a CD73-binding proprotein which is the mature protein plus additional 5' amino acid residues.

In certain aspects the polynucleotides comprise the coding sequence for the mature CD73-binding polypeptide, e.g., an anti-CD73 antibody (e.g., a clone 10.3 antibody or a clone 2C5 antibody) or an antigen-binding fragment thereof fused in the same reading frame to a marker sequence that allows, for example, for purification of the encoded polypeptide. For example, the marker sequence can be a hexa-histidine tag (SEQ ID NO: 146) supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used.

The present disclosure also provides variants of the described polynucleotides encoding, for example, CD73-binding fragments, analogs, and derivatives of the CD73-binding molecules disclosed herein (e.g., a clone 10.3 antibody or a clone 2C5 antibody).

The polynucleotide variants can contain alterations in the coding regions, non-coding regions, or both. In some aspects the polynucleotide variants contain alterations which produce silent substitutions, additions, or deletions, but do not alter the properties or activities of the encoded polypeptide. In some aspects, nucleotide variants are produced by silent substitutions due to the degeneracy of the genetic code. Polynucleotide variants can be produced for a variety of reasons, e.g., to optimize codon expression for a particular host (change codons in the human mRNA to those preferred by a bacterial host such as *E. coli*). Vectors and cells comprising the polynucleotides described herein are also provided.

In some aspects a DNA sequence encoding a CD73-binding molecule, e.g., an anti-CD73 antibody (e.g., a clone 10.3 antibody or a clone 2C5 antibody) or an antigen-binding fragment thereof can be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the polynucleotide sequences encoding a particular isolated polypeptide of interest will be inserted into an expression vector and operatively linked to an expression control sequence appropriate for expression of the protein in a desired host. Proper assembly can be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

In certain aspects, recombinant expression vectors are used to amplify and express DNA encoding anti-CD73 antibodies (e.g., a clone 10.3 antibody or a clone 2C5 antibody) or antigen-binding fragments thereof. Recombinant expression vectors are replicable DNA constructs which have synthetic or cDNA-derived DNA fragments encoding a polypeptide chain of an anti-CD73 antibody or and antigen-binding fragment thereof, operatively linked to suitable transcriptional or translational regulatory elements derived from mammalian, microbial, viral or insect genes.

A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *E.* coli, including pCR 1, pBR322, pMB9 and their derivatives, wider host range plasmids, such as M13 and filamentous single-stranded DNA phages.

Suitable host cells for expression of a CD73-binding molecule, e.g., an anti-CD73 antibody (e.g., a clone 10.3 antibody or a clone 2C5 antibody) or antigen-binding fragment thereof include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed. Appropriate cloning and expression vectors for use with bacterial, fungal, yeast, and mammalian cellular hosts are described by Pouwels et al. (Cloning Vectors: A Laboratory Manual, Elsevier, N.Y., 1985), the relevant disclosure of which is hereby incorporated by reference. Additional information regarding methods of protein production, including antibody production, can be found, e.g., in U.S. Patent Publication No. 2008/0187954, U.S. Pat. Nos. 6,413,746 and 6,660,501, and International Patent Publication No. WO 04009823, each of which is hereby incorporated by reference herein in its entirety.

Various mammalian or insect cell culture systems can also be advantageously employed to express recombinant CD73-binding molecules, e.g., anti-CD73 antibodies (e.g., a clone 10.3 antibody or a clone 2C5 antibody) or antigen-binding fragments thereof. Expression of recombinant proteins in mammalian cells can be performed because such proteins are generally correctly folded, appropriately modified and completely functional.

Examples of suitable mammalian host cell lines include HEK-293 and HEK-293T, the COS-7 lines of monkey kidney cells, described by Gluzman (Cell 23:175, 1981), and other cell lines including, for example, L cells, C127, 3T3, Chinese hamster ovary (CHO), NSO, HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, Bio-Technology 6:47 (1988).

CD73-binding molecules, e.g., anti-CD73 antibodies (e.g., a clone 10.3 antibody or a clone 2C5 antibody) or antigen-binding fragments thereof produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine (SEQ ID NO: 146), maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an AMICON® or Millipore PELLICON® ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify a CD73-binding molecule (e.g., a clone 10.3 antibody or a clone 2C5 antibody). Some or all of the foregoing purification steps, in various combinations, can also be employed to provide a homogeneous recombinant protein.

A recombinant CD73-binding protein, e.g., an anti-CD73 antibody (e.g., a clone 10.3 antibody or a clone 2C5 antibody) or antigen-binding fragment thereof produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Patent Publication Nos. 2008/0312425, 2008/0177048, and 2009/0187005, each of which is hereby incorporated by reference herein in its entirety.

In certain aspects, the CD73-binding molecule is a polypeptide that is not an antibody. A variety of methods for identifying and producing non-antibody polypeptides that bind with high affinity to a protein target are known in the art. See, e.g., Skerra, Curr. Opin. Biotechnol., 18:295-304 (2007), Hosse et al., Protein Science, 15:14-27 (2006), Gill et al., Curr. Opin. Biotechnol., 17:653-658 (2006), Nygren, FEBS J., 275:2668-76 (2008), and Skerra, FEBS J., 275: 2677-83 (2008), each of which is incorporated by reference herein in its entirety. In certain aspects, phage display technology can been used to identify/produce an CD73-binding polypeptide. In certain aspects, the polypeptide comprises a protein scaffold of a type selected from the group consisting of protein A, a lipocalin, a fibronectin domain (e.g., a fibronectin domain such as a Tenascin-3 Fn III domain), an ankyrin consensus repeat domain, and thioredoxin.

VI. Treatment Methods Using Therapeutic Anti-CD73 Antibodies

The present disclosure provides methods directed to the use of anti-CD73 binding molecules, e.g., antibodies, including antigen-binding fragments, variants, and derivatives thereof (for example, a clone 10.3 antibody or a clone 2C5 antibody), to treat patients having a disease associated with CD73 expression or CD73-expressing cells, e.g., cancer. In some specific aspects, such cancer is lung cancer, breast cancer, colon cancer, and lymphoma.

By "CD73-expressing cell" is meant a cell expressing CD73. CD73 can be membrane-bound via glycosyl phosphatidylinositol-anchoring and also be present as a soluble protein. Methods for detecting CD73 expression in cells and other suitable samples are well known in the art and include, but are not limited to immunohistochemistry, flow cytometry, Western blot, ELISA, and the like.

Though the following discussion refers to diagnostic methods and treatment of various diseases and disorders with an CD73-binding molecule of the present disclosure (e.g., a clone 10.3 antibody or a clone 2C5 antibody), the methods described herein are also applicable to any other anti-CD73 antibodies, and the antigen-binding fragments, variants, and derivatives (e.g., fusion proteins or conjugates) of these anti-CD73 antibodies that retain the desired properties of the anti-CD73 antibodies disclosed herein, e.g., being capable of specifically binding CD73 and neutralizing its 5'-nucleotidase activity. In some aspects, CD73-binding molecules are human or humanized antibodies that do not mediate human ADCC, or are anti-CD73 antibodies that are engineered such that they do not mediate ADCC.

In some aspects, the CD73-binding molecule is a CD730010 antibody or antigen-binding fragment thereof, a clone 10.3 antibody or an antigen-binding fragment thereof, a CD730002 antibody or antigen-binding fragment thereof, a clone 2C5 antibody or an antigen-binding fragment thereof, or a CD73004 antibody or antigen-binding fragment thereof. In other aspects, the CD73-binding molecule is a clone 10.3 mutant antibody. In some aspects, the CD73-binding molecule is a clone 10.3 monoclonal antibody. In some aspects, the CD73-binding molecule is a clone 10.3 monoclonal antibody engineered to extend serum half-life. In other aspects, the CD73-binding molecule is a clone 10.3 YTE mutant antibody. In other aspects, the CD73-binding molecule is a clone 2C5 mutant antibody. In some aspects, the CD73-binding molecule is a clone 2C5 monoclonal antibody. In some aspects, the CD73-binding molecule is a clone 2C5 monoclonal antibody engineered to extend serum half-life. In other aspects, the CD73-binding molecule is a clone 2C5 YTE mutant antibody.

In one aspect, treatment includes the application or administration of an anti-CD73 binding molecule, e.g., an antibody (e.g., a clone 10.3 antibody or a clone 2C5 antibody) or antigen-binding fragment, variant, or derivative thereof of the current disclosure to a subject or patient, or application or administration of the anti-CD73 binding molecule to an isolated tissue or cell line from a subject or patient, where the subject or patient has a disease, a symptom of a disease, or a predisposition toward a disease. In another aspect, treatment is also intended to include the application or administration of a pharmaceutical composition comprising the anti-CD73 binding molecule, e.g., an antibody or antigen-binding fragment, variant, or derivative thereof of the current disclosure to a subject or patient, or application or administration of a pharmaceutical composition comprising the anti-CD73 binding molecule to an isolated tissue or cell line from a subject or patient, who has a disease, a symptom of a disease, or a predisposition toward a disease.

The anti-CD73 binding molecules, e.g., antibodies (e.g., a clone 10.3 antibody or a clone 2C5 antibody) or antigen-binding fragments, variants, or derivatives thereof of the present disclosure are useful for the treatment of various cancers. In one aspect, the present disclosure provides anti-CD73 binding molecules, e.g., antibodies (e.g., a clone 10.3 antibody or a clone 2C5 antibody) or antigen-binding fragments, variants, or derivatives thereof for use as a medicament, in particular for use in the treatment or prophylaxis of cancer (e.g., colon cancer, breast cancer, lymphoma, or non-small cell carcinoma. In some aspect, the cancer presents a prometastatic phenotype. In some aspects, the cancer is a metastatic cancer. In some aspects, the anti-CD73 binding molecules disclosed herein can trigger adaptive anti-tumor activity and/or inhibit metastasis. In some particular aspects, the anti-Cd73 binding molecules disclosed herein can inhibit metastasis in breast cancer.

In accordance with the methods of the present disclosure, at least one anti-CD73 binding molecule, e.g., an antibody (e.g., a clone 10.3 antibody or a clone 2C5 antibody) or antigen-binding fragment, variant, or derivative thereof as defined elsewhere herein is used to promote a positive therapeutic response with respect to cancer. The term "positive therapeutic response" with respect to cancer treatment refers to an improvement in the disease in association with the activity of these anti-CD73 binding molecules, e.g., antibodies or antigen-binding fragments, variants, or derivatives thereof, and/or an improvement in the symptoms associated with the disease. Thus, for example, an improvement in the disease can be characterized as a complete response. By "complete response" is intended an absence of clinically detectable disease with normalization of any previously test results. Alternatively, an improvement in the disease can be categorized as being a partial response. A "positive therapeutic response" encompasses a reduction or inhibition of the progression and/or duration of cancer, the reduction or amelioration of the severity of cancer, and/or the amelioration of one or more symptoms thereof resulting from the administration of an anti-CD73 binding molecule disclosed herein.

In specific aspects, such terms refer to one, two or three or more results following the administration of anti-CD73 binding molecules disclosed herein: (1) a stabilization, reduction or elimination of the cancer cell population; (2) a stabilization or reduction in cancer growth; (3) an impairment in the formation of cancer; (4) eradication, removal, or control of primary, regional and/or metastatic cancer; (5) a reduction in mortality; (6) an increase in disease-free, relapse-free, progression-free, and/or overall survival, duration, or rate; (7) an increase in the response rate, the durability of response, or number of patients who respond or are in remission; (8) a decrease in hospitalization rate, (9) a decrease in hospitalization lengths, (10) the size of the cancer is maintained and does not increase or increases by less than 10%, preferably less than 5%, preferably less than 4%, preferably less than 2%, and (12) an increase in the number of patients in remission.

Clinical response can be assessed using screening techniques such as magnetic resonance imaging (MM) scan, x-radiographic imaging, computed tomographic (CT) scan, flow cytometry or fluorescence-activated cell sorter (FACS) analysis, histology, gross pathology, and blood chemistry, including but not limited to changes detectable by ELISA, RIA, chromatography, and the like. In addition to these positive therapeutic responses, the subject undergoing therapy with the anti-CD73 binding molecule, e.g., an antibody or antigen-binding fragment, variant, or derivative thereof, can experience the beneficial effect of an improvement in the symptoms associated with the disease.

The anti-CD73 binding molecules, e.g., antibodies (e.g., a clone 10.3 antibody or a clone 2C5 antibody) or antigen-binding fragments, variants, or derivatives thereof disclosed herein can be used in combination with any known therapies for cancer, including any agent or combination of agents that are known to be useful, or which have been used or are currently in use, for treatment of cancer, e.g., colon cancer, lung cancer (e.g., non-small cell carcinoma), lymphoma, breast cancer In specific aspects the CD73-binding molecules disclosed herein, e.g., antibodies (e.g., a clone 10.3 antibody or a clone 2C5 antibody) or antigen-binding fragments thereof, can be administered in combination with antibodies or antibody fragments targeting, for example, PD-1 (programmed death 1 protein), In some aspects, the anti-PD-1 antibody is pembrolizumab (KEYTRUDA®, formerly lambrolizumab, also known as MK-3475) or an antigen-binding fragment thereof. In some aspects, the anti-PD-1 antibody is nivolumab (BMS-936558, MDX-1106, ONO-4538, OPDIVA®) or an antigen-binding fragment thereof. In some aspects, the anti-PD-1 antibody is MEDI4736 or an antigen-binding fragment thereof.

In some aspects, the CD73-binding molecules disclosed herein (for example, a clone 10.3 antibody or a clone 2C5 antibody) can be administered in combination with an anti-PD-1 antibody. In some aspects, the administration of a combination treatment comprising an CD73-binding molecule disclosed herein (for example, MEDI9447, a clone 10.3 antibody or a clone 2C5 antibody) in combination with an anti-PD-1 antibody, can increase survival by about 10%, about 20%, about 30%, about 40%, about 50%, about 60%, about 70%, about 80%, about 90%, or about 100% compared to untreated subjects or subjects treated with a monotherapy (e.g., an anti-PD-1 antibody without an anti-CD73 antibody). In some aspects, the administration of a combination treatment comprising an CD73-binding molecule disclosed herein (for example, a clone 10.3 antibody or a clone 2C5 antibody) in combination with an anti-PD-1 antibody, can increase survival by about 2-fold, about 3-fold, about 4-fold, about 5-fold, about 6-fold, about 7-fold, about 8-fold, about 9-fold, or about 10-fold compared to untreated subjects or subjects treated with a monotherapy (e.g., an anti-PD-1 antibody without an anti-CD73 antibody).

Where the combined therapies comprise administration of an anti-CD73 binding molecule in combination with administration of another therapeutic agent (e.g., an anti-PD1), the methods disclosed herein encompass co-administration, using separate formulations or a single pharmaceutical formulation, and consecutive administration in either order. In some aspects, the anti-CD73 antibodies described herein (for example, a clone 10.3 antibody or a clone 2C5 antibody) are administered in combination with other drugs, wherein the antibody or antigen-binding fragment, variant, or derivative thereof and the therapeutic agent(s) can be administered sequentially, in either order, or simultaneously (i.e., concurrently or within the same time frame).

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

A further aspect is the use of anti-CD73 binding molecules, e.g., antibodies or antigen-binding fragments, variants, or derivatives thereof (for example, a clone 10.3 antibody or a clone 2C5 antibody), for diagnostic monitoring of protein levels in tissue as part of a clinical testing procedure, e.g., to determine the efficacy of a given treatment regimen. For example, detection can be facilitated by coupling the antibody to a detectable sub stance.

Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$, or $^{3}H$.

VII. Pharmaceutical Compositions and Methods of Administration

Methods of preparing and administering anti-CD73 binding molecules, e.g., antibodies, or antigen-binding fragments, variants, or derivatives thereof (e.g., a clone 10.3 antibody or a clone 2C5 antibody) to a subject in need thereof are well known to or are readily determined by those skilled in the art. The route of administration of the anti-CD73 binding molecule, e.g., an antibody, or antigen-binding fragment, variant, or derivative thereof can be, for example, oral, parenteral, by inhalation or topical. The term parenteral as used herein includes, e.g., intravenous, intraarterial, intraperitoneal, intramuscular, subcutaneous, rectal, or vaginal administration. However, in other methods compatible with the teachings herein, anti-CD73 binding molecules, e.g., antibodies, or antigen-binding fragments, variants, or derivatives thereof, of the present disclosure can be delivered directly to the site of the adverse cellular population thereby increasing the exposure of the diseased tissue to the therapeutic agent.

As discussed herein, anti-CD73 binding molecules, e.g., antibodies, or antigen-binding fragments, variants, or derivatives thereof of the present disclosure (for example, a clone 10.3 antibody or a clone 2C5 antibody) can be administered in a pharmaceutically effective amount for the in vivo treatment of CD73-expressing cell-mediated diseases such as certain types of cancers.

The pharmaceutical compositions used in this disclosure can comprise pharmaceutically acceptable carriers, including, e.g., water, ion exchangers, proteins, buffer substances, and salts. Preservatives and other additives can also be present. The carrier can be a solvent or dispersion medium. Suitable formulations for use in therapeutic methods disclosed herein are described in Remington's Pharmaceutical Sciences (Mack Publishing Co.) 16th ed. (1980).

In any case, sterile injectable solutions can be prepared by incorporating an active compound (e.g., an anti-CD73 antibody, or antigen-binding fragment, variant, or derivative thereof, for example a clone 10.3 antibody or a clone 2C5 antibody, by itself or in combination with other active agents) in the required amount in an appropriate solvent followed by filtered sterilization. Further, the preparations can be packaged and sold in the form of a kit. Such articles of manufacture can have labels or package inserts indicating that the associated compositions are useful for treating a subject suffering from, or predisposed to a disease or disorder.

Parenteral formulations can be a single bolus dose, an infusion or a loading bolus dose followed with a maintenance dose. These compositions can be administered at specific fixed or variable intervals, e.g., once a day, or on an "as needed" basis.

The composition can be administered as a single dose, multiple doses or over an established period of time in an infusion. Dosage regimens also can be adjusted to provide the optimum desired response (e.g., a therapeutic or prophylactic response).

Therapeutically effective doses of the compositions of the present disclosure, for treatment of CD73-expressing cell-mediated diseases, such as certain types of cancers including e.g., colon cancer, vary depending upon many different factors, including means of administration, target site, physiological state of the patient, whether the patient is human or an animal, other medications administered, and whether treatment is prophylactic or therapeutic. Usually, the patient is a human, but non-human mammals including transgenic mammals can also be treated. Treatment dosages can be titrated using routine methods known to those of skill in the art to optimize safety and efficacy.

The amount of at least one anti-CD73 binding molecule, e.g., antibody or binding fragment, variant, or derivative thereof (for example, a clone 10.3 antibody or a clone 2C5 antibody) to be administered is readily determined by one of ordinary skill in the art without undue experimentation given the disclosure of the present disclosure. Factors influencing the mode of administration and the respective amount of at least one anti-CD73 binding molecule, e.g., antibody, antigen-binding fragment, variant or derivative thereof include, but are not limited to, the severity of the disease, the history of the disease, and the age, height, weight, health, and physical condition of the individual undergoing therapy. Similarly, the amount of anti-CD73 binding molecule, e.g., antibody, or fragment, variant, or derivative thereof, to be administered will be dependent upon the mode of administration and whether the subject will undergo a single dose or multiple doses of this agent.

The present disclosure also provides for the use of an anti-CD73 binding molecule, e.g., an antibody or antigen-binding fragment, variant, or derivative thereof (for example, a clone 10.3 antibody or a clone 2C5 antibody), in the manufacture of a medicament for treating a type of cancer, including, e.g., colon cancer.

The disclosure also provides for the use of an anti-CD73 binding molecule, e.g., antibody, or antigen-binding fragment, variant, or derivative thereof (for example, a clone 10.3 antibody or a clone 2C5 antibody), in the manufacture of a medicament for treating a subject for treating a type of cancer. In certain aspects, the medicament is used in a subject that has been pretreated with at least one other therapy.

By "pretreated" or "pretreatment" is intended the subject has received one or more other therapies (e.g., been treated with at least one other anti-cancer therapy) prior to receiving the medicament comprising the anti-CD73 binding molecule, e.g., antibody or antigen-binding fragment, variant, or derivative thereof (for example, a clone 10.3 antibody or a clone 2C5 antibody). It is not necessary that the subject was a responder to pretreatment with the prior therapy or therapies. Thus, the subject that receives the medicament comprising the anti-CD73 binding molecule, e.g., an antibody or antigen-binding fragment, variant, or derivative thereof could have responded, or could have failed to respond to pretreatment with the prior therapy, or to one or more of the prior therapies where pretreatment comprised multiple therapies.

The present disclosure also provides for the co-administration of an anti-CD73 binding molecule, e.g., antibody, or antigen-binding fragment, variant, or derivative thereof (for example, a clone 10.3 antibody or a clone 2C5 antibody) and at least one other therapy. The anti-CD73 antibody and the at least one other therapy can be co-administered together in a single composition or can be co-administered together at the same time or overlapping times in separate compositions. In some aspects, the anti-CD73 antibody can be co-administered with, for example, an antibody that targets PD-1 (programmed death 1 protein The present disclosure also provides for the use of an anti-CD73 binding molecule, e.g., antibody, or antigen-binding fragment, variant, or derivative thereof (for example, a clone 10.3 antibody or a clone 2C5 antibody), in the manufacture of a medicament for treating a subject for treating cancer, wherein the anti-CD73 binding molecule is administered before a subject has been treated with at least one other therapy.

VIII. Diagnostics

The present disclosure further provides diagnostic methods useful during diagnosis of CD73-expressing cell-mediated diseases such as certain types of cancer, which involves measuring the expression level of CD73 protein in tissue or other cells or body fluid from an individual and comparing the measured expression level with a standard CD73 expression level in normal tissue or body fluid, whereby an increase in the expression level compared to the standard is indicative of a disorder.

The anti-CD73 antibodies disclosed herein and antigen-binding fragments, variants, and derivatives thereof (e.g., a clone 10.3 antibody or a clone 2C5 antibody), can be used to assay CD73 protein levels in a biological sample using classical immunohistological methods known to those of skill in the art (e.g., see Jalkanen, et al., *J. Cell. Biol.* 101:976-985 (1985); Jalkanen et al., *J. Cell Biol.* 105:3087-3096 (1987)). Other antibody-based methods useful for detecting CD73 protein expression include immunoassays, such as the enzyme linked immunosorbent assay (ELISA), immunoprecipitation, or Western blotting. Suitable assays are described in more detail elsewhere herein.

By "assaying the expression level of CD73 polypeptide" is intended qualitatively or quantitatively measuring or estimating the level of CD73 polypeptide in a first biological sample either directly (e.g., by determining or estimating absolute protein level) or relatively (e.g., by comparing to the disease associated polypeptide level in a second biological sample). CD73 polypeptide expression level in the first biological sample can be measured or estimated and compared to a standard CD73 polypeptide level, the standard being taken from a second biological sample obtained from an individual not having the disorder or being determined by averaging levels from a population of individuals not having the disorder. As will be appreciated in the art, once the "standard" CD73 polypeptide level is known, it can be used repeatedly as a standard for comparison.

By "biological sample" is intended any biological sample obtained from an individual, cell line, tissue culture, or other source of cells potentially expressing CD73. Methods for obtaining tissue biopsies and body fluids from mammals are well known in the art.

IX. Kits Comprising CD73-binding Molecules

The present disclosure also provides kits that comprise at least one of the CD73-binding molecules described herein, e.g., anti-CD73 antibodies or antigen-binding fragment thereof, variants, or derivatives of the molecules disclosed herein (e.g., a clone 10.3 antibody or a clone 2C5 antibody), that can be used to perform the methods described herein. In certain aspects, a kit comprises at least one purified anti-CD73 antibody or an antigen-binding fragment thereof in one or more containers. In some aspects, the kits contain all of the components necessary and/or sufficient to perform a detection assay, including all controls, directions for performing assays, and any necessary software for analysis and presentation of results. One skilled in the art will readily recognize that the disclosed CD73-binding molecule, e.g., an anti-CD73 antibody or antigen-binding fragment thereof of the present disclosure (e.g., a clone 10.3 antibody or a clone 2C5 antibody) can be readily incorporated into one of the established kit formats which are well known in the art.

X. Immunoassays

Anti-CD73 binding molecules disclosed herein, e.g., anti-CD73 antibodies or antigen-binding fragments thereof, variants, or derivatives of the molecules disclosed herein (e.g., a clone 10.3 antibody or a clone 2C5 antibody), can be assayed for immunospecific binding by any method known in the art. The immunoassays that can be used include but are not limited to competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, (1994) Current Protocols in Molecular Biology (John Wiley & Sons, Inc., NY) Vol. 1, which is incorporated by reference herein in its entirety).

CD73-binding molecules, e.g., anti-CD73 antibodies or antigen-binding fragments thereof, and their variants or derivatives (for example, a clone 10.3 antibody or a clone 2C5 antibody), can be employed histologically, as in immunofluorescence, immunoelectron microscopy or non-immunological assays, for in situ detection of CD73 or conserved variants or peptide fragments thereof. In situ detection can be accomplished by removing a histological specimen from a patient, and applying thereto a labeled CD73-binding molecule, e.g., an anti-CD73 antibody or antigen-binding fragment thereof, variant, or derivative thereof, preferably applied by overlaying the labeled CD73-binding molecule (e.g., and antibody or fragment) onto a biological sample. Through the use of such a procedure, it is possible to determine not only the presence of CD73, or conserved variants or peptide fragments, but also its distribution in the examined tissue. Using the present disclosure, those of ordinary skill will readily perceive that any of a wide variety of histological methods (such as staining procedures) can be modified in order to achieve such in situ detection.

The binding activity of a given lot of CD73-binding molecule, e.g., anti-CD73 antibody (for example, a clone 10.3 antibody or a clone 2C5 antibody) or antigen-binding fragment thereof, variant or derivative thereof can be determined according to well-known methods. Those skilled in the art will be able to determine operative and optimal assay conditions for each determination by employing routine experimentation.

Methods and reagents suitable for determination of binding characteristics of an isolated CD73-binding molecule, e.g., anti-CD73 antibody (for example, a clone 10.3 antibody or a clone 2C5 antibody) or antigen-binding fragment thereof, variant, or an altered/mutant derivative thereof, are known in the art and/or are commercially available. Equipment and software designed for such kinetic analyses are commercially available (e.g., BIAcore, BIAevaluation software, GE Healthcare; KINExA Software, Sapidyne Instruments).

The practice of the present disclosure will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described are generally followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., NY).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevere, Amsterdam); Goldsby et al., eds. (2000) Kuby Immunnology (4th ed.; H. Freemand & Co.); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlan); Sambrook and Russell (2001) Molecular Cloning: A Laboratory Manual (Cold Spring Harbor Press); Lewin (2003) Genes VIII (Prentice Hal12003); Harlow and Lane (1988) Antibodies: A Laboratory Manual (Cold Spring Harbor Press); Dieffenbach and Dveksler (2003) PCR Primer (Cold Spring Harbor Press).

All of the references cited above, as well as all references cited herein, are incorporated herein by reference in their entireties.

The following examples are offered by way of illustration and not by way of limitation.

EXAMPLES

Aspects of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, can be practiced without departing from the scope of the present disclosure.

CD73 (Cluster of Differentiation 73), also known as ecto-5'-nucleotidase (NT5E), is a transmembrane receptor found on tumor cells as well as in normal stromal cells such as endothelial cells and certain leukocytes. CD73 catalyzes adenosine monophosphate to adenosine and organic phosphate. Binding of the extracellular portion of adenosine receptors signals through cyclic AMP to inhibit T-cell receptor activation (reviewed by Linden and Cekic, 2012). CD73 is believed to play a role in mediating the inhibitory function of regulatory B and T lymphocytes (Saze et al, 2013), as well as in maintaining endothelial integrity (reviewed by Jalkanen and Salmi, 2008).

In addition to its role in normal biology, CD73 and adenosine affect tumor biology. The presence of extracellular adenosine within the tumor microenvironment has been described as an immunosuppressive "halo" (Antonioli et al, 2013). Consistent with this role for adenosine, knockout mice lacking adenosine receptors have been shown to reject tumors more readily than normal mice (Ohta et al, 2006). The primary source of extracellular adenosine within tumors is believed to be CD73 (Augusto et al, 2013). Consistent with this hypothesis as well as studies with A2A deficient mice, knockout mice lacking CD73 have increased antitumor immunity (Stagg et al, 2011) and show decreased carcinogenesis (Stagg et al, 2012) when compared normal mice. Specifically, extracellular adenosine is believed to mediate the immunosuppressive effects of both regulatory T cells and myeloid-derived suppressor cells (MDSCs), among others (reviewed by Antonioli, 2013). Taken together with other studies showing that molecular inhibition of CD73 with small molecules or antibodies can inhibit tumor formation, growth, and metastasis (reviewed by Young et al, 2014), it is hypothesized that tumors use CD73 to generate adenosine and, thereby, to suppress anti-tumor immunity. Accordingly, anti-CD73 antibodies that selectively bind to and inhibit the ectonucleotidase activity of CD73 are likely to be useful for enhancing an anti-tumor immune response.

Example 1: Isolation and Identification of Anti-CD73 Antibodies

Human scFv phage display libraries were panned with biotinylated CD73 extracellular domain (ECD) to isolate antibodies binding to human, cynomolgus, and murine CD73. CD73-specific scFv antibodies were isolated from the human scFv phage display library in a series of repeated alternate selection cycles on biotinylated human and murine CD73 extracellular domain (ECD) produced in-house from mammalian cells essentially as described previously in Lloyd et al., PEDS 22:159-68 (2009). ScFv genes from rounds 2 and 3 of the selection outputs were converted in batch into bacterial scFv-Fc or Fab expression vectors. Bacterial culture supernatants carrying soluble scFv-Fc or Fab were screened for their binding to human, murine, and cynomolgus CD73 ECD by ELISA or homogeneous time resolved fluorescence (HTRF). The top hits showing cross reactivity were selected, subjected to DNA sequencing, and converted to whole immunoglobulin G1 triple mutant antibody format ("IgG-TM", IgG1 Fc sequence incorporating mutations L234F, L235E and P331S). IgG1 TM antibodies were expressed in mammalian cells, purified by affinity chromatography and ranked based on their characteristics in binding and functional assays.

The lead antibody, CD730010, was shown to bind specifically to human, murine, and cynomolgus CD73-expressing cells (by flow cytometry), and to inhibit the activity of recombinant soluble CD73 ECD as well as native CD73 displayed on cells. Affinity maturation of CD730010 was initiated to enhance binding affinity of CD730010 to human CD73.

Prior to affinity optimization, it was attempted to revert as many framework residues of CD730010 to the closest human germline sequences (based on IMGT repertoire) without impairing affinity (See Example 8). This was done to minimize the potential immunogenicity of the final antibody drug in humans. All framework residues of the VL domain and all except one framework residue of the VH domain could be reverted to match the amino sequence of human germlines IGLV1-44, IGLJ3, IGHV3-23, and IGHJ2. Lysine in position 94 (Kabat numbering; Kabat, 1991) of the VH domain of CD730010 could not be reverted without loss of affinity.

TABLE 10

Affinity of parental anti-CD730010 antibody and antibody variants with germlined amino acids.

| antibody variant | amino acid in VL position | | | | | amino acid in VH position | EC50 [nM] |
|---|---|---|---|---|---|---|---|
| | 1 | 2 | 11 | 3 | 39 | 94 | |
| CD73001.0 | L | P | V | K | V | R | 69 |
| CD730010 GL9 | Q | S | A | Q | L | R | 64 |

TABLE 10-continued

Affinity of parental anti-CD730010 antibody and antibody variants with germlined amino acids.

| antibody variant | amino acid in VL position | | | | | amino acid in VH position | EC50 [nM] |
|---|---|---|---|---|---|---|---|
| | 1 | 2 | 11 | 3 | 39 | 94 | |
| CD730010 GU10 | L | P | V | K | V | K | 205 |
| CD730010 GL18 | Q | S | A | Q | L | K | 132 |

The affinity and potency of germlined CD730010 antibody was enhanced by generating libraries of CDR variants and testing the variants for improved binding to CD73 (See Example 9). Several mutations with the best improvement in affinity were combined to generate the candidate drug MEDI9447. The nucleotide and deduced amino acid sequences of MEDI9447 are shown in FIGS. 1A-1D.

Example 2: Epitope Binning of Anti-CD73 Antibodies

The ability of anti-CD73 antibodies to compete with each other for binding to human CD73 ECD was assessed on an Octet instrument essentially as described (Abdiche Y N et al., Anal Biochem 386: 172-80 (2009). CD73 ECD protein and first anti-CD73 antibody were pre-incubated and added to a biotinylated second anti-CD73 antibody captured on a Streptavidin sensor. If the first anti-CD73 antibody blocked binding of CD73 ECD to the second anti-CD73 antibody, both antibodies were placed in same or overlapping epitope bins. If both antibodies could bind simultaneously to CD73 ECD, they were placed in non-overlapping epitope bins. Pairwise testing of the anti-CD73 antibodies demonstrated that they belong to 3 non-overlapping epitope bins (Table 2).

TABLE 2

Epitope bins of anti-CD73 antibodies

| Epitope bin | Antibodies |
|---|---|
| A | CD730002, CD730004, CD730008, CD730011 |
| B | CD730003, CD730010, CD730021, CD730042, CD730046, CD730047 |
| C | CD730068, CD730069 |

Example 3: Binding of Anti-CD73 Antibodies to CD73

The binding affinity and specificity of anti-CD73 antibodies was determined by Surface Plasmon Resonance (SPR) and flow cytometry.

A ProteOn XPR36 instrument was used to characterize binding of MEDI9447 to human, murine, and cynomolgus CD73 ECD. MEDI9447 was affinity-captured using an anti-human Fc antibody. CD73 ECD was in the mobile phase. The association and dissociation of CD73 to MEDI9447 could be accurately described with the Langmuir 1:1 model. The results shown in Table 3 demonstrate that the affinity of MEDI9447 to CD73 ECD from the three species is comparable and in the low picomolar range.

TABLE 3

Affinity of MEDI9447 to CD73 ECD Determined by Surface Plasmon Resonance

| Analyte | $k_a$ $(M^{-1}s^{-1})$ | $k_d$ $(s^{-1})$ | $K_D$ (M) |
|---|---|---|---|
| Human CD73 ECD | $2.57 \times 10^6$ | $1.06 \times 10^{-5}$ | $4.1 \times 10^{-12}$ |
| Murine CD73 ECD | $2.41 \times 10^6$ | $2.32 \times 10^{-6}$ | $0.9 \times 10^{-12}$ |
| Cynomolgus CD73 ECD | $2.71 \times 10^6$ | $1.76 \times 10^{-5}$ | $6.5 \times 10^{-12}$ |

$k_a$ Association rate constant;
$k_d$ Dissociation rate constant;
$K_D$ Dissocation constant Binding of MEDI9447 to native CD73 expressed on human, murine, and cynomolgus monkey cell lines was characterized by flow cytometry. The cells were incubated with various concentrations of MEDI9447 and antibody binding was monitored with and fluorophore-labeled anti-human Fc antibody. A plot of the median fluorescence intensity as a function of the MEDI9447 concentration was fitted nonlinearly using a one-site binding isotherm model to calculate the equilibrium dissociation constant. The analysis by flow cytometry confirms the binding of MEDI9447 to human, murine, and cynomolgus CD73 with comparable affinities (Table 4), although the $K_D$ values are 13—126-fold greater than those determined by SPR, probably because of conformational differences between recombinant and native CD73.

TABLE 4

Affinity of MEDI9447 to Native CD73 Determined by Flow Cytometry

| Analyte | $K_D$ (M) |
|---|---|
| MDA-MB-231 cells (human) | $154 \times 10^{-12}$ |
| 4T1 cells (murine) | $113 \times 10^{-12}$ |
| MK-1 cells (cynomolgus) | $84 \times 10^{-12}$ |

To determine the specificity of MEDI9447 for human CD73 by flow cytometry, cell lines were developed. MDA-MB-231 cells, which are human breast cancer cells derived from a pleural effusion, were transfected with human CD73 short hairpin RNA (shRNA) to knock down the cell-surface expression of CD73. Jurkat cells, a line of T cells derived from Burkitt lymphoma cells, were transfected with a plasmid expressing human CD73 mRNA to knock in cell-surface expression of CD73. Jurkat cells express little endogenous CD73.

Specificity of MEDI9447 for human CD73 was determined by the ratio of MEDI9447 binding to a high CD73-expressing cell line (MDA-MB-231) to low expressing cell line (MDA-MB-231, CD73-shRNA). Specificity of MEDI9447 for human CD73 was also determined by the ratio of high CD73 expressing cell line (Jurkat-CD73 knock-in) to lower expressing cell line Jurkat.

Specificity of MEDI9447 for murine CD73 (mCD73) was determined by flow cytometry comparing the mouse cell line 4T1 (high mCD73 expression) to the knocked-down cell line (4T1 mCD73-shRNA). In addition, specificity of MEDI9447 for Jurkat cells with murine CD73 knock-in was compared with wild-type Jurkat cells (no murine CD73).

TABLE 5

Specificity of MEDI9447 for Human and Mouse CD73

| Specificity of MEDI9447 | Cell Line Relationship | Mean Fluorescence Intensity Ratio (MFIR) |
|---|---|---|
| human | MDA-MB-231/MDA-MB-231 (CD73- shRNA) | 3.5 |
| human | Jurkat (CD73 knock-in)/Jurkat | 7.9 |
| Mouse | 4T1/4T1(mCD73 -shRNA) | 3.9 |
| Mouse | Jurkat (mCD73 knock-in)/Jurkat | 57.1 |

Example 4: Internalization of CD73 by Anti-CD73 Antibody MEDI9447

Antibody-mediated internalization or shedding of CD73 was assessed by flow cytometry. MDA-MB-231 cells were incubated in presence of 100 nM MEDI9447 or negative control antibody R347 in growth medium at 37° C. for 0-4 hours. Cells were washed and resuspended in ice-cold PBS. The presence of CD73 on the cell surface was detected by adding 10 nM DyLight488-labeled detection antibody. Cells were incubated for 15 minutes, washed and analyzed by flow cytometry. The detection antibody binds to an epitope of CD73 that is different from the MEDI9447 epitope and both antibodies simultaneously bind to CD73 without interference. Cell surface expression of CD73 dropped to 73% of its original value after 4 hours incubation with MEDI9447, suggesting that 27% of CD73 was either internalized or shed upon MEDI9447 binding (Table 6).

TABLE 6

Percentage of CD73 remaining on the cell surface of MDA-MB-231 cells after incubation with test antibody

| Time [h] | R347 | MEDI9447 |
|---|---|---|
| 0 | 100% | 100% |
| 0.25 | 107% | 90% |
| 0.5 | 104% | 90% |
| 1 | 102% | 87% |
| 2 | 104% | 80% |
| 4 | 102% | 73% |

Internalization of MEDI9447 into cell lines MDA-MB-231 (human mammary carcinoma) and 4T1 (murine mammary carcinoma) was assessed using a human Antibody Internalization Kit that is sold commercially as the FabZAP assay (Advanced Targeting Systems, San Diego Calif.). Serial dilutions of MEDI9447 or negative control antibody R347 were pre-incubated with 40 nM FabZAP reagent (Fab fragment of a polyclonal anti-human IgG antibody conjugated to the cytotoxic protein saporin) and then added to the cell lines. After 3 days in culture, cell proliferation was measured using a luminescent cell viability assay sold commercially as the CELLTITER-GLO® assay (Promega, Madison Wis.). This assay was used to calculate $EC_{50}$ values and maximum toxicity. The FabZAP reagent cannot internalize into cells on its own. It binds to a test antibody (e.g., MEDI9447) and is cytotoxic only upon internalization of the test antibody. MEDI9447 caused internalization of FabZAP and inhibited cell proliferation in a dose-dependent manner.

TABLE 7

Antibody-mediated Internalization of Cytotoxic FabZAP Reagent into MDA-MB-231 Cells and 4T1 Cells

| | MDA-MB-231 | | 4T1 | |
|---|---|---|---|---|
| | $EC_{50}$ [pM] | maximum toxicity | $EC_{50}$ [pM] | maximum toxicity |
| MEDI9447 | 3.5 | 97% | 18.5 | 97% |

Cell proliferation of MDA-MB-231 cells and 4T1 cells treated with serial dilutions of test antibody and FabZAP reagent was measured by CELLTITER-GLO® assay (FIG. 2). The signal from the negative control antibody R347 in the CELLTITER-GLO® assay was subtracted from the signal of MEDI9447 and the EC50 value and maximum toxicity were calculated by fitting the dose-response curve using non-linear regression analysis.

Example 5: Inhibition of 5'Ectonucleotidase Activity by Anti-CD73 Antibody MEDI9447

In this study, the functional activity of MEDI9447 was determined in an in vitro assay that measured the CD73-catalyzed hydrolysis of AMP using a human non-small cell carcinoma cell line, NCI-H322. Formulation of MEDI9447 was prepared by diluting its stock solution in serum-free RPMI medium to a final concentration of 1 µM. Formulation of R347 was prepared by diluting its stock solution in RPMI to a final concentration of 1 µM.

NCI-H322 cells were centrifuged for 5 minutes at 1500 rpm. The supernatant was removed and replaced with serum-free RPMI medium. The cell suspension was counted using the VI-CELL (Beckman, Coulter) cell counter. The cells were plated into 96-well plates at a cell density of 10,000 cells per 100 µLs per well. 504, of 4x concentrated AMP (200 µM) was added. The plates were then incubated at 37° C., 5% $CO_2$ for 24 hours. Plates were centrifuged and 504, of the culture supernatant was transferred well-to-well to 96-well opaque round bottom plates. 2X ATP was then added. CELLTITER-GLO® (Promega) was added according to the manufacturer's instructions. Cellular enzyme inhibition of 5' ectonucleotidase was measured on a multilabel reader, the Perkin-Elmer Envision Workstation. The samples were analyzed using Prism Software.

MEDI9447 specifically inhibited dephosphorylation of adenosine monophosphate (AMP) in a human in vitro system. In a cell-based assay of surface-expressed CD73, conversion of adenosine monophosphate to adenosine was reduced in a dose-dependent manner by MEDI9447, but not by an irrelevant isotype control antibody (FIG. 3). The results depicted in FIG. 3 were obtained using CD73-expressing NSCLC cells that were plated into 96-well non-tissue culture treated plates (Falcon 3788) at 10,000 cells per well in 100 µL of RPMI medium without additives. Antibodies were added in duplicate along with AMP (200 µM final concentration) and plates were incubated at 37° C., 5% $CO_2$ for 24 hours. Plates were then centrifuged for 3 minutes at 1500 rpm. Supernatants were collected into a new 96 well plate (Costar #3605) and ATP was added to a final concentration of 100 μM. CELLTITER-GLO® reagent (Promega) was added 1:1 and cellular CD73 enzyme AMP phosphorylase activity was determined by measuring ATP levels using the Envision luminescence plate reader (Perkin Elmer). Buffer containing only ATP and AMP was used as a negative control. The assay was repeated and the results shown at FIG. 3 are representative of two similar experiments using other human cancer cell lines.

These results indicate that MEDI9447 inhibited the production of adenosine by cancer cells. Adenosine mediates the tumor's immunosuppressive effects within the tumor microenvironment.

Example 6: Reduction in Tumor-Infiltrating Myeloid-Derived Suppressor Cells by MEDI9447

CT26 cells, which are derived from a murine colon cancer, were established by subcutaneous (SC) injection of $5 \times 10^5$ cells suspended in 0.1 mL of PBS into the right flanks of 4-to-6-week-old female mice. The mice were treated with MEDI9447 or with a control antibody.

10 mice per group were used in this study. Animals were randomly assigned into groups. Animals in Group 1 were untreated and Group 2 was administered an isotype control. MEDI9447 was administered to Group 3. Test articles were administered intraperitoneally twice weekly starting on Day 3. On Day 16, 5 animals from each group were necropsied and tumors were isolated.

Group designation and dose levels are presented in Table 8.

TABLE 8

| Group Designation and Dose Levels | | | | | |
|---|---|---|---|---|---|
| Group | Number of animals (female) | Treatment | Days of dosing | Dose level (mg/kg)[a] | ROA |
| 1 | 5 | untreated | N/A | N/A | N/A |
| 2 | 5 | isotype | 2X weekly | 20 mg/kg | IP |
| 3 | 5 | MEDI9447 | 2X weekly | 10 mg/kg | IP |

N/A = not applicable; ROA = route of administration.

Tumors were measured on Days 1, 7, 9, 12, 14, and 16 by caliper, and the volumes of tumors were calculated as follows:

$$\text{(tumor volume length (mm)} \times \text{(tumor volume width (mm))}/2 \quad (1)$$

The anticancer effects of MEDI9447 were expressed as percent tumor growth inhibition, which was calculated as follows:

$$(\text{Average tumor volume for MEDI9447}/\text{Average tumor volume for R347-TM}) \times 100 \quad (2)$$

Tumors were isolated for flow cytometry. Tumors were dissected from CT26 tumor-bearing mice on study Day 16. Tumors were cut into small pieces and were digested with collagenase. After a 30-minute incubation, the digested sample was passed through a 70-micron filter. Dissociated cells were pelleted at 1000 rpm for 5 minutes at 4° C. and were re-suspended in fluorescence-activated cell sorting (FACS) buffer. Cells were counted on Vi-Cell using the default setting. $1 \times 10^6$ cells were plated per well. Cells were stained with anti-CD45 (to detect all leukocytes) anti-GR1 (to detect MDSCs) and anti-Ly6g (Gran MDSC). Data were acquired on the LSRII flow cytometer. Significant p-values, if any, obtained from the MDSC analyses are presented in FIG. 4 adjacent to the descriptive statistics (ie, mean and standard deviation).

MEDI9447 inhibited tumor growth in murine CT26 syngeneic Balb/C tumor model (FIG. 4).

MEDI9447 reduced the proportion of tumor-infiltrating MDSCs in the murine CT26 syngeneic Balb/C tumor model (FIG. 5).

MEDI9447 inhibited the growth of CT26 murine syngeneic tumors. In addition, myeloid-derived suppressor cells were decreased in syngeneic CT26 colon carcinoma tumors following treatment with MEDI9447. Intra-tumoral MDSCs have an immunosuppressive effect on the tumor microenvironment, allowing for enhanced tumor growth. The observed reduction in intra-tumoral MDSCs following treatment with MEDI9447 demonstrates a mechanism by which treatment with MEDI9447 reduces tumor immune suppression.

Example 7: A Combination of MEDI9447 mIgG1 and an Anti-PD-1 Antibody Reduced Tumor Growth and Increased Survival Syngeneic tumors were established by subcutaneous (SC) injection of 0.1 ml of $5 \times 10^6$ CT26 cells/ml suspended in HBSS into the right flanks of 8- to 10-week-old animals.

Tumors were measured by caliper and the volumes of tumors (TV) were calculated using the following formula:

$$TV = (L \times W^2)/2 \quad (1)$$

where L is tumor length in millimeters and W is tumor width is in millimeters

Mice were randomized into groups based on bodyweight. There were no animal substitutions. 60 female Balb/c mice were used in this study.

Animals were randomly assigned into 6 groups. Animals were administered MEDI9447(mIgG1). Test articles were administered by intraperitoneal (IP) injection twice weekly starting on Day 3. Group designation and dose levels are presented in Table 9.

TABLE 9

| Group Designation and Dose Levels | | | | | |
|---|---|---|---|---|---|
| Group | Number of animals (Female) | Treatment | Schedule of dosing (2x weekly) | Dose level (mg/kg)[a] | ROA |
| 1 | 10 | Untreated | NA | NA | NA |
| 2 | 10 | Isotype mIgG1 | 4 doses | 10 | ip |
| 3 | 10 | Isotype rIgG2a | 4 doses | 10 | ip |
| 4 | 10 | MEDI9447 mIgG1 | 4 doses | 10 | ip |
| 6 | 10 | Anti-PD1 | 4 doses | 0.5 | ip |
| 7 | 10 | Anti-PD1 + MEDI9447 | 4 doses | 0.5 + 10 | ip |

F = female; IV = intravenous; M = male; ROA = route of administration.
[a] Dose volume: 10 mL/kg.

(a) Results of In Vivo Tumor Inhibition Study

CT26 murine colon carcinoma were implanted into syngeneic Balb/C mice and treated with anti-CD73 (MEDI9447 mIgG1; 10 mg/kg), anti-PD1 (0.5 mg/kg) or the combination (10 mg/kg anti-CD73 and 0.5 mg/kg anti-PD1). The combination treatment significantly inhibited tumor growth when compared to anti-CD73 alone (p=0.015, ANOVA). Tumor volumes from each group of animals were plotted for individual animals out to study day 40. No control group mice were tumor free by the end of the 40 day study period (See FIG. 6). Anti-CD73 treatment alone resulted in 10% tumor free animals at the end of study. Anti-PD1 treatment alone also resulted in 10% tumor free animals at the end of study. Remarkably, the combination of anti-CD73 and anti-PD treatment resulted in 60% tumor free mice. None of the control group mice were tumor free by the end of the study. CT26 tumors were measured in mice treated with anti-CD73 (MEDI9447 mIgG1), anti-PD1 or the combination of anti-CD73 and anti-PD1. Mice were measured until study day 40, and humanely sacrificed once tumors reached 2000 mm³. The combination of anti-CD73 and anti-PD1 treatment together resulted in a statistically significant increase in survival when compared to anti-CD73 or anti-PD1 treatment alone (p value=0.005 and p=0.038, respectively, Log Rank Test) (FIG. 7). Median survival increased from 25 and 33 days (anti-CD73 and anti-PD1, respectively) compared to "undefined" at day 40 for the combination.

TABLE 9

Outcome at Study Day 40

| Treatment | Tumor free mice (%) | Survival (%) |
|---|---|---|
| untreated | 0 | 0 |
| Isotype mIgG1 | 0 | 0 |
| Isotype rIgG2a | 0 | 0 |
| Anti-CD73 | 10 | 10 |
| Anti-PD1 | 10 | 20 |
| Anti-CD73 + Anti-PD1 | 60 | 70 |

In summary, anti-CD73 antibody, MEDI9447 mIgG1, showed enhanced anti-tumor activity when combined with an anti-PD-1 antibody in a murine syngeneic CT26 colon carcinoma model. In addition, the combination of anti-CD73 and anti-PD treatment resulted in 60% tumor free mice. The combination of anti-CD73 and anti-PD1 treatment together also resulted in a statistically significant increase in survival when compared to anti-CD73 or anti-PD1 treatment alone.

Example 8: Anti-CD730010 Antibody and Antibody Variants

The VH and VL amino acid sequences of CD730002 and CD730010 were aligned to the known human germline sequences using IMGT/V-QUEST (http://www.imgt.org) and the closest germline sequences were identified by sequence similarity. For the CD730010 VH domain, these were IGHV3-23 and IGHJ2. For the CD730010 VL domain, these were IGLV1-44 and IGLJ3. Six non-germline residues outside the CDR regions were identified: R94 in VH, and L1, P2, V11, K37, and V39 in VL (Kabat numbering). Nucleotides in the CD730010 IgG1-TM expression vector were back-mutated by standard molecular biology techniques, so that the resulting expression vectors encoded germline amino acids in these positions (K94 in VH, and Q1, S2, A11, Q37, and L39 in VL). The CD730010 IgG1-TM protein variants were expressed, purified and tested for binding to CD73-expressing MD-MB-231 cells by flow cytometry. All 5 non-germline amino acids in VL could be changed to their germline residues without impairing binding. However, R94 in VH is important for binding and changing it to K impairs binding. The nucleotide sequence of CD730010 GL9 was used as template for generating affinity-optimized antibody variants.

For CD730002, the closest germline genes were IGHV3-23 and IGHJ3 for the VH domain, and IGLV3-1 and IGLJ3 for the VL domain. Four non-germline residues outside the CDR regions were identified: R94 in VH, and T20, R57, L81 and F87 in VL (Kabat numbering). Nucleotides in the CD730002 IgG1-TM expression vector were back-mutated by standard molecular biology techniques, so that the resulting expression vectors encoded germline amino acids in these positions (K94 in VH, and S20, G57, M81, and Y87 in VL). The CD730002 IgG1-TM protein variants were expressed, purified and tested for binding to recombinant human and murine CD73 by flow cytometry. All 4 non-germline amino acids in VL could be changed to their germline residues without impairing binding. However, R94 in VH is important for binding and changing it to K impairs binding. Variant CD730002 SGMY (non-germlined V, fully germlined VL) was used as a template for generating affinity-optimized antibody variants.

Example 9: Affinity-Optimization of Anti-CD73 Antibodies CD730010GL9

CD730010GL9 IgG1-TM was enhanced by screening Fab libraries comprising variant CDR sequences with single amino acid mutations. Each of the 61 positions in the six CDRs was individually randomized to 19 amino acids (all natural amino acids except Cysteine), generating a library with a theoretical diversity of 1159 unique clones (19 amino acids per position times 61 positions). Bacterial Fab fragments were produced from 4224 clones of the library and screened for binding to human and murine CD73 protein by capture ELISA (Assay 2). 180 clones with increased binding signal compared to parental CD730010 GL9 IgG1-TM were selected and the mutations in the VH or VL domain were identified by DNA sequencing. The Fab concentration in the bacterial supernatants was normalized and the binding of the normalized supernatants to human and murine CD73 protein was evaluated by direct ELISA (Assay 1). Table 11 lists selected beneficial single amino acid substitutions and their effect on binding to recombinant CD73 protein.

TABLE 11

Single amino acid variants of CD730010 GL9 with improved affinity.

| CDR | Amino acid change | ELISA signal, fold improvement over parental antibody | |
|---|---|---|---|
| | | huCD73 | muCD73 |
| L1 | P32E | 27.7 | 6.7 |
| L1 | P32D | 11.7 | 6.5 |
| H3 | Y102K | 9.9 | 7.4 |
| L2 | N51D | 8.9 | 4.5 |
| H2 | G54N | 8.9 | 7.1 |
| H2 | S52W | 8.9 | 4.4 |
| H3 | Y102M | 7.9 | 6.3 |
| H3 | Y102L | 7.3 | 5.8 |
| L2 | S56G | 7.1 | 5.6 |
| L2 | N51A | 6.7 | 2.5 |
| H3 | Y102A | 6.6 | 5.0 |
| L1 | P32G | 6.1 | 5.8 |
| L1 | P32A | 6.0 | 5.5 |
| L2 | Q53L | 6.0 | 3.8 |
| L2 | Q53Y | 5.8 | 2.3 |
| L2 | P55L | 5.7 | 4.3 |
| H2 | S56R | 5.6 | 4.9 |
| L2 | N51Q | 4.2 | 2.3 |
| H2 | G54W | 4.2 | 3.7 |
| H2 | A50L | 4.2 | 3.0 |
| L2 | Q53F | 4.1 | 2.7 |
| H1 | M34Y | 3.9 | 2.9 |
| L2 | P55I | 3.7 | 3.2 |
| H3 | Y102Q | 3.6 | 3.0 |

TABLE 11-continued

Single amino acid variants of CD730010 GL9 with improved affinity.

| CDR | Amino acid change | ELISA signal, fold improvement over parental antibody | |
|---|---|---|---|
| | | huCD73 | muCD73 |
| L2 | Q53W | 3.1 | 2.7 |
| L2 | Q53H | 2.4 | 1.9 |
| L2 | L50F | 2.2 | 1.4 |
| H1 | S35H | 1.8 | 1.1 |
| H1 | M34I | 1.5 | 1.1 |

To further improve the affinity of the anti-CD73 antibody, several single amino acid changes which improved binding when compared to parental CD730010 GL9 were combined to create a combinatorial Fab library (Assay 4). Fab fragments of 4224 clones of the combinatorial library were produced in E. coli and screened for binding to human and murine CD73 protein by capture ELISA. The top 20 clones from each screening assay were selected for further characterization. The Fab concentration in the supernatants was normalized and serial dilutions of normalized supernatants were tested for binding to human and murine CD73 by capture ELISA and direct ELISA. Clones C1, C2, D3 and G10 showed strong binding to human and murine CD73 and were selected for further characterization.

Antigen-binding of CD730010 GL9 was also enhanced using affinity-based phage selections. Large scFv libraries derived from the lead CD730010 GL9 sequence were created by oligonucleotide-directed mutagenesis of the variable heavy (VH) complementarity determining region 3 (CDR3) or variable light (VL) chain CDR3 using standard molecular biology techniques as described (Finch et al., JMB 411, 791-807 (2011)). The libraries were panned in a series of repeated alternate selection cycles with biotinylated human and murine CD73 extracellular domain protein. ScFv genes from round 3 of the selection output were batch-converted into a bacterial IgG expression vector. Bacterial culture supernatants containing soluble IgG were screened for their binding to human and murine CD73. IgG variants with significantly improved binding to CD73 compared to parental CD730010 GL9 were subjected to DNA sequencing. Two variants, GRVE and HPT, were selected for further characterization.

To generate further affinity improvements, beneficial mutations identified from the combinatorial Fab library and from the affinity-based phage selection were combined creating variants 73combo1 to 73combo6.

Example 10: Affinity-Optimization of Anti-CD73 Antibodies CD730002SGMY

CD730002SGMY IgG1-TM was enhanced by screening Fab libraries comprising variant CDR sequences with single amino acid mutations as described for CD730010GL9. Five amino acid mutations in the VH domain and four amino acid mutations in the VL domain were identified that resulted in increased binding signal to recombinant CD73. Table 12 lists beneficial single amino acid substitutions and their effect on binding to recombinant CD73.

TABLE 12

Single amino acid variants of CD730002SGMY with improved affinity.

| CDR | Amino acid change | FACS signal, fold improvement over parental antibody MDA-MB-231 cells |
|---|---|---|
| H1 | Y32V | 1.2 |
| H1 | M34R | 1.1 |
| H2 | T57P | 1.5 |
| H2 | A60G | 1.3 |
| H2 | G65R | 1.3 |
| L2 | T52S | 1.5 |
| L2 | R54Y | 1.2 |
| L2 | P55L | 1.9 |
| L2 | P55H | 1.5 |

To further improve the affinity of the anti-CD73 antibody CD730002SGMY, IgG variants were prepared that harbored one beneficial amino acid change in the VH domain and one beneficial amino acid change in the VL domain. Antibody variants were prepared by transient transfection of 293F cells and were screened for binding to MDA-MB-231 cells by flow cytometry. Clone 2C5 had a 3-fold lower EC50 value than parental CD730002SGMY.

Example 11: Affinity of Enhanced Anti-CD73 Antibodies

The affinity of enhanced anti-CD73 antibodies (in IgG1-TM format) to human, murine, and cynomolgus CD73 was determined by flow cytometry and surface plasmon resonsance (SPR) (Table 13). The enhanced antibodies had pM affinity to cellular and recombinant CD73 from the three species.

TABLE 13

Affinity of anti-CD73 antibodies to human, murine, and cynomolgus CD73

| | KD [pM] | | | | | |
|---|---|---|---|---|---|---|
| | flow cytometry | | | SPR (Proteon) | | |
| | MB-MDA-231 (human) | 4T1 (murine) | MK-1 (cyno) | human CD73 | murine CD73 | cyno CD73 |
| CD730010 | 8000 | 6100 | ND | 3580 | 2470 | 1920 |
| CD730010GL9 | 8949 | 16365 | 16460 | 1640 | ND | ND |
| P32E | 178 | 145 | 110 | 63 | 35 | 27 |
| C1 | 179 | 95 | 160 | 29 | 6 | 12 |
| C2 | 158 | 67 | 105 | 23 | | |
| G10 | 354 | 259 | 258 | 9 | | |

TABLE 13-continued

Affinity of anti-CD73 antibodies to human, murine, and cynomolgus CD73

| | KD [pM] | | | | | |
|---|---|---|---|---|---|---|
| | flow cytometry | | | SPR (Proteon) | | |
| | MB-MDA-231 (human) | 4T1 (murine) | MK-1 (cyno) | human CD73 | murine CD73 | cyno CD73 |
| HPT | 739 | 5812 | 1138 | 548 | | |
| GRVE | 125 | 88 | 101 | 29 | | |
| 73combo1 (C1 + GRVE + HPT) | 157 | 150 | 90 | 7 | 2 | 8 |
| 73combo2 (C2 + GRVE + HPT) | 166 | 64 | 74 | 5 | | |
| 73combo3(D3 + GRVE + HPT) | 154 | 113 | 84 | 4 | 1 | 7 |
| 73combo5 (G10 + GRVE + HPT) | 169 | 205 | 78 | 7 | | |
| 73combo6(GRVE + HPT) | 166 | 82 | 107 | 15 | | |
| CD730002 | 52 | 50 | 52 | 7 | 40 | 15 |
| CD730002 2C5 | 84 | 55 | 63 | 9 | 22 | 9 |

Example 12: The Anti-Human CD73 Antibody, Phen0203 hIgG1, Inhibited AMP-Mediated Suppression of CD4+CD25− T Cell Proliferation In Vitro, in a Concentration Dependent-Manner A study was conducted to determine the ability of an anti-CD73 antibody (Phen0203) to relieve AMP-mediated T-cell suppression in vitro. In this in vitro study, the ability of an anti-human CD73 antibody (Phen0203 hIgG1) to inhibit the catalysis of adenosine monophosphate to adenosine and organic phosphate by CD73 and the subsequent impact on T-cell function was examined. Phen0203 hIgG1 has similar functional properties to MEDI9447, including the ability to inhibit the cellular and biochemical enzymatic activity of CD73 in vitro).

Phen0203 hIgG1 antibody is a human IgG1 mAb with no engineering in the heavy chain constant region. Similar to MEDI9447, it also selectively binds to and inhibits production of immunosuppressive adenosine by the ectonucleotidase activity of human CD73. However, Phen0203 lacks cross-reactivity against mouse CD73.

In an assay for AMP-mediated T-cell suppression, primary human CD4+ T cells depleted of CD25+ cells were isolated from the content of leukocyte cones and used as effector cells; each cone was processed separately. Briefly, the content from a leukocyte cone was diluted in PBS, then layered over FICOLL-PAQUE® Plus (GE Healthcare, Chalfont St Giles, UK) and centrifuged at 400×g for 40 minutes with brakes turned off. Peripheral blood mononuclear cells (PBMC) were then isolated from the interface and washed with PBS by centrifugation at 200×g for 10 minutes. Supernatant was discarded and cells were suspended in PBS. Viable cells were determined, then pelleted at 350×g for 5 minutes and suspended in RoboSep buffer (Stem Cell, Grenoble, France) at a concentration of $5 \times 10^7$ per mL. CD4+ T cells were isolated from PBMCs by negative selection using the EasySep human CD4+ T cell enrichment kit (Stem Cell, Grenoble, France) and the RoboSep (Stem Cell, Grenoble, France). Purified CD4+ T cells were pelleted and resuspended at $1.5 \times 10^7$ per mL in RoboSep buffer. DynaBeads CD25 (a component of Dynabeads Regulatory CD4+ CD25+ T cell kit; Life Technologies, Paisley, UK) were added at 200 μL per $1.5 \times 10^7$ cells and incubated for 25 minutes at 4° C. with continuous mixing. Cells were then placed into a DynaMag-15 magnet (Life Technologies, Paisley, UK) for 1 minute and the supernatant containing the CD4+CD25− effector cells were transferred into a new tube.

Isolated effector cells were labeled with CFSE probe (3 μM) using the CellTrace CFSE cell proliferation kit (Life Technologies, Paisley, UK) at a cell density of $1 \times 10^6$ cells per mL in PBS containing 0.1% BSA with an incubation period of 15 minutes at 37° C. Cells were washed twice with warm X-Vivo 15 media and suspended at $5 \times 10^5$ cells per mL in the same media. Labeled effector cells were activated for 1 hour at 37° C. by adding 25 μL of anti-CD3 and anti-CD28 coated microbeads (Dynabeads human T-activator CD3/CD28; Life Technologies, Paisley, UK) per $1 \times 10^6$ cells and 60 IU/mL of rhIL-2. Thereafter, activated CD4+CD25− cells (approximately 50,000 in 100 μL) were added to wells of sterile round-bottom 96-well plates. Serial dilutions of the following reagents were performed in X-Vivo 15 media (Lonza, Slough, UK): the test article Phen0203 hIgG1; R347 control antibody; APCP as a positive control; and SCH58261 a selective antagonist for adenosine receptor A2A. Phen0203 hIgG1 was received as a ready-to-use formulation (MedImmune, Gaithersburg, Md.) and was diluted in phosphate-buffered saline (PBS). R347 was received as a ready-to-use formulation (MedImmune, Gaithersburg, Md.) and was diluted in PBS.

To the cells in the plate, 50 μL of diluted reagents were added followed by 50 μL of X-Vivo 15 (Lonza, Slough, UK) containing 400 μM or 800 μM of AMP (Sigma-Aldrich, Gillingham, UK). The following control wells were also included: activated CFSE-labeled CD4+CD25− cells with no AMP (activated control); CFSE-labeled CD4+CD25− cells with AMP but no test/control articles (untreated control); and un-activated (resting control) CF SE-labeled CD4+ CD25− cells with no AMP. Cells in the assay were gently pelleted by centrifugation, at 100×g for 2 minutes, and placed in a 37° C. humidified tissue culture incubator with 5% $CO_2$ for 72 hours.

After 72 hours of incubation, cells were pelleted by centrifugation at 380 g for 4 minutes, washed once with 100 μL of FACS buffer (eBioscience, Hatfield, UK) and finally suspended in 100 μL of PBS containing 3.7% of formaldehyde for flow cytometry analysis on a BD FACSCanto II (BD Biosciences, Oxford, UK). Resting CFSE+CD4+CD25− cells with no AMP well was used to identify cells that have undergone cellular division (divided cells).

CD73 was found to be expressed on a subset of CD4+ T cells. In the presence of extracellular AMP, CD73+ T cells have the potential to enable paracrine/autocrine pathways which involves the metabolism of AMP to adenosine by CD73, followed by the activation of the adenosine receptors and the subsequent regulation of T cell function. This CD73/adenosine pathway was modeled in vitro by using purified $CD4^+CD25^-$ primary human T cells activated by TCR-signaling and rhIL-2. T-cell proliferation was suppressed in the presence of 100 or 200 μM of extracellular AMP.

The in vitro capacity for an anti-CD73 antibody (Phen0203 hIgG1) to inhibit AMP-mediated T cell suppression was evaluated. Addition of Phen0203 hIgG1, in the presence of AMP, increased T cell proliferation in a concentration-dependent manner (FIG. 9). In contrast, R347 isotype control antibody had no effect. Without intending to be bound by theory, this indicates that the binding of an anti-CD73 antibody to CD73 was able to block or decrease the generation of adenosine and the subsequent inhibitory effect on T cell function via adenosine receptor signaling.

APCP and SCH58261 are known small molecule inhibitors of CD73 (Hausler et al., Cancer Immunol Immunother. 2011 60(10):1405-18) and adenosine receptor A2A (Marcoli et al., Neuropharmacology 2003 45(2):201-10), respectively. The addition of these molecules also resulted in the increase of T-cell proliferation in the presence of AMP (FIGS. 9 and 10). Without intending to be bound by theory, this indicates a role for CD73, adenosine and adenosine receptor A2A signaling in mediating T-cell suppression in this in vitro primary human cell assay system.

Phen0203 hIgG1, an anti-human CD73 antibody, was capable of inhibiting AMP-mediated suppression of $CD4^+CD25^-$ T cell proliferation in vitro, in a concentration dependent-manner. The data provide a scientific rationale for an anti-CD73 antibody approach targeting the immunosuppressive effects of the AMP/CD73/adenosine pathway.

Example 13: A Combination of Anti-CD73 Antibody and Adenosine Receptor Inhibitor had Synergistic Effects on TNF-Alpha Secretion Studies have shown that molecular inhibition of CD73 and its production of adenosine using anti-CD73 antibodies can inhibit tumor formation, growth, and metastasis. Adenosine receptor A2A is hypothesized to play a role in negatively regulating immune cells. Thus, the antitumor effect of anti-CD73 antibody, MEDI9447 (mIgG1), could be increased by administering it in combination with an adenosine receptor inhibitor (A2ARi) was examined.

The release of immune activating cytokines IFNγ and TNFα was evaluated in human mixed leukocyte cultures with anti-CD73 monoclonal antibody alone and in combination with an adenosine receptor inhibitor (A2ARi). The levels of IFNγ and TNFα in supernatants were detected by ELISA. Human peripheral blood lymphocytes were set up in a mixed leukocyte reaction for 72 hours and stimulated with anti-CD73 alone, A2AR inhibitor alone or both agents. Peripheral blood mononuclear cells from pairwise combinations of 8 donors were incubated for 72 hours in the presence of 1 μM anti-CD73 antibody MEDI9447 and 1 μM A2ARi SCH58261, either alone or in combination. After incubation, supernatant levels of Interferon gamma (IFNγ) and Tumor Necrosis Factor Alpha (TNFα) were measured using a Mesoscale ELISA plate. The levels of IFNγ and TNFα observed after incubation with each compound were plotted as duplicate fold-control values using levels from incubation with an isotype control antibody as a negative control.

The anti-CD73 antibody MEDI9447 (mIgG1) and adenosine receptor inhibitor (A2ARi) were capable of inducing these cytokines to different extents in human cells, as varying levels of IFNγ and TNFα were detected in the supernatants (FIGS. 11 and 12). Anti-CD73 antibody, MEDI9447 (mIgG1), when combined with an adenosine receptor inhibitor (A2ARi), demonstrated enhanced TNFα levels in the in vitro human mixed lymphocyte stimulation assay across all donor pairs tested (FIG. 12). Indeed, administration of the combination of MEDI9447 and SCH58261 showed a synergistic effect on TNFα secretion in the human mixed lymphocyte stimulation assay in all donor pairs.

Example 15: Methods and Assays Used

The following assays and methods were used to perform the preceding examples.

Assay 1: Direct ELISA 384-well ELISA plates were coated with about 1.5 ng/well recombinant CD73 protein, blocked with 1% BSA/0.1% Tween20/PBS and incubating with antibody samples for 90 minutes at room temperature. This was followed by incubation with goat-anti-Iglambda-horseradish peroxidase (HRP) conjugate for 30 min at room temperature. HRP activity was detected with tetra methyl benzidine (TMB) substrate and the reaction was stopped with 1 M HCl. Plates were read at 450 nm.

Assay 2: Capture ELISA 384-well ELISA plates were coated with about 3 ng/well sheep-anti-human Fd antibody (for screening antibodies in Fab format), blocked with 1% BSA/0.1% Tween20/PBS and incubating with samples for 90 minutes at room temperature. Biotinylated CD73 protein was then added for 1 h at room temperature. This was followed by incubation with streptavidin-horseradish peroxidase (HRP) conjugate for 30 min at room temperature. HRP activity was detected with tetra methyl benzidine (TMB) substrate and the reaction was stopped with 1 M HCl. Plates were read at 450 nm.

About 50 ng/well biotinylated recombinant CD73 was used to screen clones with single amino acid mutations. For the screening of clones from the combinatorial library, 10 ng/well biotinylated recombinant CD73 were used.

Assay 3: Flow Cytometry Binding Assay

All flow cytometry experiments were run at 4C and reagents were prepared in PBS/1% FBS buffer. 10,000 cells were incubated with test antibody in 50 uL volume for 4 hours. Cells were washed twice and incubated in 50 uL goat anti-human IgGFc-AlexaFluor647 conjugate for 15 minutes. Cells were washed, resuspended in buffer supplemented with Dapi, and analyzed on a flow cytometer. Dead cells, identified by high Dapi staining, were excluded from the analysis. For the determination of $K_D$ values, a plot of the median fluorescence intensity as a function of test antibody concentration was fitted nonlinearly using a one site binding isotherm model.

Assay 4: Generation of the Antibody Library with Single Amino Acid Changes

Site-directed mutagenesis of the CDR codons of CD730010 or CD730002 was performed using a QuikChange Lightning Multi Site-Directed Mutagenesis Kit (Agilent) and primers. Each codon was mutagenized with a primer which replaced the wild-type codon with codon NNS. Mutagenized VH and VL genes were cloned into a Fab vector for bacterial expression. E. coli strain BL21(DE3) was transformed with the antibody library, individual colonies were picked and cultured in Magic Media (Invitrogen) for 24 hours at room temperature to produce bacterial Fab fragments. Bacterial supernatant was prepared and used to screen the antibody library in ELISA binding assays.

Assay 5: Generation of the Antibody Library with Combinatorial Amino Acid Changes CD730010GL9 VH and VL genes were cloned into a vector for bacterial Fab expression. Site-directed mutagenesis of the CDR codons of CD730010GL9 was performed using either QuikChange Lightning Multi Site-Directed Mutagenesis Kit (Agilent) or overlapping PCR and degenerate primers. The degenerate primers were designed to encode selected amino acid changes as well as the parental amino acid at the same position. E. coli strain BL21(DE3) was transformed with the Fab library, individual colonies were cultured in Magic Media (Invitrogen) for 24 hours at room temperature to produce bacterial Fab fragments. Bacterial supernatants were used to screen the antibody library in ELISA binding assays.

Assay 6: FabZAP Assay 1,000 cells/well were cultured in 96 well plates in RPMI/10% FBS. Serial dilutions of anti-CD73 antibodies starting at 5 nM were mixed with FabZAP reagent (Advanced Targeting Systems, San Diego Calif.) and added to the cells. After 3 days incubation at 37C, the cell proliferation was measured using the CELLTITER-GLO® assay (Promega, Madison Wis.).

The preceding description of the specific aspects will so fully reveal the general nature of the invention that others can, by applying knowledge within the skill of the art, readily modify and/or adapt for various applications such specific aspects, without undue experimentation, without departing from the general concept of the present invention. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

SEQUENCE LISTING

>SEQ ID NO: 1 CD730002 VL
QSVLTQPPSVSVSPGQTATITCSGDKVGDKYASWYQQKPGQSPVLVIYED
TKRPSRIPERFSGSNSGNTATLTISGTQALDEADYFCQAWDTSFWVFGGG
TKLTVL

>SEQ ID NO: 2 CD730002 VH
EVQLLESGGGLVQPGGSLRLSCAASGFTFSSYAMSWVRQAPGKGLEWVSA
ISGSGGSTYYADSVKGRFTISRDNSKNTLYLQMNSLRAEDTAVYYCARDK
GYYWYMDVWGQGTMVTSS

>SEQ ID NO: 3 CD730010 VL
LPVLTQPPSVSGTPGQRVTISCSGSLSNIGRNPVNWYKQVPGTAPKLLIY
LNNQRPSGVPDRFSGSKSGTSASLAISGLQSEDEADYYCATWDDSLNGWL
EGGGTKLTVL

>SEQ ID NO: 4 CD730010 VH
EVQLLESGGGLVQPGGSLRLSCAASGFTESSYAMSWVRQAPGKGLEWVSA
ISGSGGSTYYADSVKGRFTISRDNSKNTLYLQMNSLRAEDTAVYYCARLG
YSTIDYWGRGTEVTVSS

>SEQ ID NO: 5 CD730011 VL
NFMLTQPHSVSESPGKTVTISCTRSSGSIASKYVQWYQQRPGSSPMAVIY
KDNQRSSGVPDRFSGSIDSSSNSASLTISGLKPEDEADYYCQSYDASNYY
VFGTGTKVTVL

>SEQ ID NO: 6 CD730011 VH
EVQLLESGGGLVQPGGSLRLSCAASGFTESSYAMSWVRQAPGKGLEWVSA
ISGSGGSTYYADSVKGRFTISRDNSKNTLYLQMNSLRAEDTAVYYCARRG
HGLYFDLWGQGTTVTVSS

>SEQ ID NO: 7 CD730021 VL
QSVUFQPPSASGTPGQRVTISCSGSRPNIGCNINNWYQQLPGAAPKIATV
SNSQRPSGVPDRESGSKYGTSASLAISGLQSDDEADYYCGTWDDSLNGPV
EGRGTKLTVL

>SEQ ID NO: 8 CD730021 VH
QVQLQESGPGLVRPSETLSLIVINSGGSISSSSYYWAWVRQSPGKGLEWI
GNIYYRGSTYYNPSLKSRVTMSVDMSKHQESLKLSSLNAADTAVYYCASL
YSGTYVFDYWGRGTLVTVSS

>SEQ ID NO: 9 CD730042 VL
QSVLTQPASVSGSPGQSITISCAGTSSDVGGYNYVSWYQQHPGKAPKLMI
YEGSKRPSGVSNRFSGSKSGNTASLTISGLQAEDEADYYCSSYTTRSTRV
FGGGTKLTVL

>SEQ ID NO: 10 CD730042 VH
GVQLVQSGGGLVQPGGSLRLSCAASGFTFSSYGMHWVRQAPGKGLEWVAV
ISYDGSIKYYADSVKGRFTISRDDSKNALYLQMINSLRAEDTAVYYCSTL
SGSYGYEDYWGRGTLVTVSS

>SEQ ID NO: 11 CD730046 VL
QSVLTQPPSASGTPGQRVTISCSGSSSIGSNTVSWYQHLPGTAPQLLIYT
NNHRPSGVPDRSGSKSGTSASLAISGLQSEDEADYYCAAWDDSLSGYVFG
TGTKVTVL

>SEQ ID NO: 12 CD730046 VH
QVQLVQSGGGVVQPGRSLRLSCAASGFTFSSYGMHWVRQAIPGKGLEWVA
VISYDGSIKYYADSVKGRFTISRDNSKNSLFLQMNSLRDDDTATYYCARG
HLLRIGDIFYYSLDVWGQGTLVTVSS

>SEQ ID NO: 13 CD730047 VL
QSVLTQPPSASGAPGQRVTISCSGSSSNIGSNTVNWYQRLPGAAPQLLIY
NNDQRPSGIPDRFSGSKSGTSGSLVISGLQSEDEADYYCAAWDDSLSGNV
FGTGTKVTVL

>SEQ ID NO: 14 CD730047 VH
EVQLVQSGGGVVQPGRSLRLSCAASGFTFSSYGMHWVRQAPGKGLEWVAV
ISYDGSIKYYADSVKGRFAISRDNAKNTLYLQMNSLRREDTAMYYCASGL
TGVAGALGVWGRGTLVTVSS

>SEQ ID NO: 15 CD730058 VL
QSVLTQPPSVSVSPGQTATITCSGDRLRNEFVSWYQQRPGQSPVVVIYQD
IYRPSGIPDRFSGSKSGNTATLTISGPQTVDEADYYCQAWDSNTVVFGGG
TKLTVL

>SEQ ID NO: 16 CD730058 VH
QLQLQESGSGLYKPSQTLSLICAVSGGSITSGGNAWNWIRQSPGAGLEWI
GYWSNGATYYNPSLESRVTISADTSKNQFSLTLTSVTAADTAVYYCARGD
FWTGKGVFDPWGQGTLVTVSS

>SEQ ID NO: 17 10.3AA_HC
EVQLLESGGGLVQPGGSLRLSCAASGFTFSSYAYSWVRQAPGKGLEWVSA

ISGSGGRTYYADSVKGRFTISRDNSKNTLYLQMNSLRAEDTAVYYCARLG

YGRVDEWGRGTLVTVSSASTKGPSVFPLAPSSKSTSGGTAALGCLVKDYF

PEPVTVSWNSGALTSGVHTFPAVLQSSGLYSLSSVVTVPSSSLGTQTYIC

NVNHKPSNTKVDKRVEPKSCDKTHTCPPCPAPEFEGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPASIEKTISKAKGQPREPQVYT

LPPSREEMTKNQVSLTCLVKGFYPSDIAVEWESNGQPENNYKTTPPVLDS

DGSFFLYSKLTVDKSRWQQGNVFSCSVMHEALHNHYTQKSLSLSPGK

>SEQ ID NO: 18 10.3Nt_HC
GAGGTGCAGCTGTTGGAGTCTGGGGGAGGCCTTGGTACAGCCTGGGGGT

CCCTGGACTCTCCTGTGCAGCCTCTGGATTCACCTTTAGCAGCTATGCCT

ATAGCTGGGTCCGCCAGGCTCCAGGGAAGGGGCTGGAGTGGGTCTCAGCT

ATTAGTGGTAGTGGTGGTAGAACATACTACGCAGACTCCGTGAAGGGCCG

GTTCACCATTTCCAGAGACAATTCCAAGAACACGCTGTATCTGCAAATGA

ACAGCCTGAGAGCCGAGGACACGGCCGTGTATTACTGTGCGAGATTAGGG

TATGGGCGGGTGGACGAGTGGGGCAGGGGAACCCTGGTCACCGTCTCGAG

TGCGTCGACCAAGGGCCCATCCGTCTTCCCCCTGGCACCCTCCTCCAAGA

GCACCTCTGGGGGCACAGCGGCCCTGGGCTGCCTGGTCAAGGACTACTTC

CCCGAACCGGTGACGGTGTCcTGGAACTCAGGCGCtCTACCAGCGGCGTG

CACACCTTCCCGGCTGTCCTACAGTCCTCAGGACTCTACTCCCTCAGCAG

CCAGGTGACCGTGCCCTCCAGCAGCTTGGGCACCCAGACCTACATCTGCA

ACGTGAATCACAAGCCCAGCAACACCAAGGTGGACAAGAGAGTTGAGCCC

AAATcTTGTGACAAAACTCACACATGcCCAcCGTGCCCAGCACCTGAATT

CGAGGGGGGAcCGTCAGTCTTCCTCTTCCCCCCAAAACCCaaGgACACCC

TCATGATCTCCCGGACCCCTGAGGTCACTTGCGTGGTGGTGGACGTGAGC

CACGAAGACCCTGAGGTCAAGTTCAACTGGTACGTGGACGGCGTGGAGGT

GCATAATGCCAAGACAAAGCCGCGGGAGGAGCAGTACAACAGCACGTACC

GTGTGGTCAGCGTCCTCACCGTCCTGCACCAGGACTGGCTGAATGGCAAG

GAGTACAATTTGCAAGGTCTCCAACAAAGCCCTCCCAGCCTCCATcGAGA

AAACCATCTCCAAAGCCAAAGGGCAGCCCCGAGAACCACAGGTcTACACC

CTGCCCCCATCCCGGGAGGAGATGACCAAGAACCAGGTCAGCCTGACCTG

CCTGGTCAAAGGCTTCTATCCCAGCGACATCGCCGTGGAGTGGGAGAGCA

ATGGGCAGCCGGAGAACAACTACAAGACCACGCCTCCCGTGCTGGACTCC

GACGGCTCCTTCTTCCTCTATAGCAAGCTCACCGTGGACAAGAGCAGGTG

GCAGCAGGGGAACGTCTTCTCATGCTCCGTGATGCATGAGGCTCTGCACA

ACCACTAGACGCAGAAGAGCCTCTCCCTGTCTCCGGGTAAA

>SEQ. ID NO: 19 10.3AA_LC
QSVLTQPPSASGTPGQRVTISCSGSLSNIGRNPVNWYQQLPGTAPKLLIY
LDNLRLSGVPDRFSGSKSGTSASLAISGLQSEDEADYYATWDDSHPGWTF
GGGTKLTVLGQPKAAPSVTLFPPSSEELQANKATLVCLISDFYPGAVTVA
WKADSSPVKAGVETTTPSKQSNNKYAASSYLSLTPEQWKSHRSYSCQVTH
EGSTVEKTVAPTECS

>SEQ ID NO: 20 10.3Nt-LC
CAGTCTGTGCTGACTCAGCCACCCTCAGCGTCTGGGACCCCCGGGCAGAG

GGTCACCATCTCTTGTTCTGGAAGCCTCTCCAACATCGGAAGGAATCCTG

TTAACTGGTATCAGCAGCTCCCAGGGACGGCCCCCAAACTCCTCATCTAT

CTTGATAATCTACGGCTAAGTGGGGTCCCTGACCGATTTCTCTGGCTCCA

AGTCTGGAACCTCAGCCTCCCTGGCCATCAGTGGGCTCCAGTCTGAGGATG

AGGCTGATTATTACTGTGCAACATGGGATGACAGCCACCCCGGGTGGACG

TTCGGCGGAGGGACCAAGCTGACCGTCCTAGGTCAGCCCAAGGCGGCGCTC

CTCGGTCACTCTGTTCCCGCCCTCCTCTGAGGAGCTTCAAGCCAACAAGG

CCACACTGGTGTGTCTCATAAGTGACTTCTACCCGGGAGCCGTGACAGTG

GCCTGGAAGGCAGATAGCAGCCCCGTCAAGGCGGGAGTGGAGACCACCAC

ACCCTCCAAACAAAGCAACAACAAGTACGCGGCCAGCAGCTACCTGAGCC

TGACGCCTGAGCAGTGGAAGTCCCACAGAAGCTACAGCTGCCAGGTCACG

CATGAAGGGAGCACCGTGGAGAAGAGAGTGGCCCCTACAGAATGTTCA

>SEQ ID NO: 21 10.3AA_VH
EVQLLESGGGLVQPGGSLRLSCAASGFTFSSYAYSWVRQAPGKGLEWVSA
ISGSGGRTYYADSVKGRITISRDNSKNTLYLQMNSIRAEDTAVYYCARLG
YGRVDEWGRGTLVTVSS

>SEQ ID NO: 22 10.3Nt_VH
GAGGTGCAGCTGTTGGAGTCTGGGGGAGGCTTGGTACAGCCTGGGGGGTC

CCTGAGACTCTCCTGTGCAGCCTCTGGATTCACCTTTAGCAGCTATGCCT

ATAGCTGGGTCCGCCAGGCTCCAGGGAAGGGGCTGGAGTGGGTCTCAGCT

ATTAGTGGTAGTGGTGCTTAGAACATACTACGCAGACTCCGTGAAGGGCC

GGTTCACCATCTCCAGAGACAATTCCAAGAACACGCTGTATCTGCAAATG

AACAGCCTGAGAGCCGAGGACACGGCCGTGTATTACTGTGCGAGATTAGG

GTATGGGCGGGTGGACGAGTGGGGCAGGGGAACCCTTGGTCACCGTCTCG

AGT

>SEQ ID NO: 23 10.3AA_VL
QSVLTQPPSASGTPGQRVTISCSGSLSNIGRNPVNWQQLPGTAPKLLIYL
DNLRLSGVPDRFSGSKSGTSASLAISGLQSEDEADYYCATWDDSHPGWTF
GGGTKLTVL

>SEQ ID NO: 24 10.3Nt-VL
CAGTCTGTGCTGACTCAGCCACCCTCAGCGTCGGGACCCCCGGGCAGAG

GGTCACCATCTCTTGTTCTGGAAGCCTCTCCAACATCGGAAGGAATCCTG

TTAACTGGTATCAGCAGCTCCCAGGGACGGCCCCCAAACTCCTCATCTAT

CTTGATAATCTACGGCTAAGTGGGGTCCCTGACCGATTTCTCTGGCTCCA

AGTCTGGAACCTCAGCCTCCCTGGCCATCAGTGGGCTCCAGTCTGAGGAT

GAGGCTGATTATTACTGTGCAACATGGGATGACAGCCACCCCGGGTGGAC

GTTCGGCGGAGGGACCAAGCTGAGCGTCCTA

>SEQ ID NO: 25 CD7300010 parent FW1-VL
LPVLTQPPSVSGTPGQRVTISC

>SEQ ID NO: 26 CD7300010 GL FW1-VL
QSVLTQPPSASGTPGQRVTISC

>SEQ ID NO: 27 CD7300010 parent FW2-VL
WYKQVPGTAPKWY

>SEQ ID NO: 28 CD7300010 GL FW2-VL
WYQQLPGTARKLIAY

>SEQ ID NO: 29 CD7300010 parent/GL FW3-VL
GVPDRFSGSKSGTSASLAISGLQSEDEADYYC

>SEQ ID NO: 30 CD7300010 parent/GL FW4-VL (also
CD370002 and 2C5)
FGGGTKLTVL

>SEQ ID NO: 31 CD7300010 parent/GL FW2-VH (also
CD370002 and 2C5)
EVQLLESGGGLVQPGGSLRLSCAASGFTFS >SEQ ID NO: 32 CD7300010 parent/GL FW2-VH (also
CD370002 and 2C5)
WVRQAPGKGLEWVS

SEQUENCE LISTING

>SEQ ID NO: 33 CD7300010 parent/GL FW3-VH (also CD370002 and 2C5)
RFTISRDNSKNTLYLQMNSLRAEDTAVYYCAR >SEQ ID NO: 34 CD7300010 parent/GL FW4-VH
WGRGTLVTVSS >SEQ ID NO: 35 CD7300010 CDR1-VH (also CD370002 and 2C5)
SYAMS

>SEQ ID NO: 36 10.3 CDR1-VH
SYAYS

>SEQ ID NO: 37 CDR2-VH (also CD370002)
AISGSGGSTYYADSVKG

>SEQ ID NO: 38 CDR2-VH
LIWGSWGSTYYADSVICG

>SEQ ID NO: 39 CDR2-VH
AISGSGGRTYYADSVKG

>SEQ ID NO: 40 CDR2-VH
AISGSWGRTYYADSVKG

>SEQ ID NO: 41 CDR3-VH
LGYSTIDY

>SEQ ID NO: 42 CDR3-VH
LGYSTIDK

>SEQ ID NO: 43 CDR3-VH
LGYSTIDM

>SEQ ID NO: 44 CDR3-VH
LGYSTIDL

>SEQ ID NO: 45 CDR3-VH
LGYGRVDE

>SEQ ID NO: 46 CDR1-VL
SGSLSNIGRNMIN

>SEQ ID NO: 47 CDR1-VL
SGSLSNIGRNEVN

>SEQ ID NO: 48 CDR1-VL
SGSLSNIGRNDVN

>SEQ ID NO: 49 CDR2-VL
LNNQRPS

>SEQ ID NO: 50 CDR2-VL
LDNLRLG

>SEQ ID NO: 51 CDR2-VL
LIDNLRLS

>SEQ ID NO: 52 CDR2-VL
LNNQRLG

>SEQ ID NO: 53 CDR3-VL
ATWDDSLNGWL

>SEQ ID NO: 54 CDR3-VL
ATWDDSLKGWL

>SEQ ID NO: 55 CDR3-VL
ATWDDSLIGWL

>SEQ ID NO: 56 CDR3-VL
AINVDDSEIPGWI

>SEQ ID NO: 57 CD7300110-VL
LPVLTQPPSVSGTPGQRVTISCSGSLSNIGRNPVNWYKQVPGTAPKLLIY
LNNQRPSGVPDRFSGSKSGTSASLAISGLQSEDEADYYCATWDDSLNGWL
FGGGIKLTNTL

>SEQ ID NO: 58 CD730010GL9-VL
QSVLTQPPSASGTPGQRVTISCSGSLSNIGRNPVNWYQQLPGTAPKLLIY
LNNQRPSGVPDRFSGSKSGTSASLAISGLQSEDEADYYCATWDDSLNGWL
FGGGTKLTVL

>SEQ ID NO: 59 P32E-VL
QSVLTQPPSASGTPGQRVTISCSGSLSNIGRNEVNWYQQLPGTAPKLLIY
LNNQRPSGVPDRFSGSKSGTSASLAISGLQSEDEADYYCATWDDSLNGWL
FGGGTKLTVL

>SEQ ID NO: 60 C1-VL
QSNTLTQPPSASGTPGQRNTTISCSGSLSNIGRNEVNWYQQLPGTAPKLL
IYLNNQRPSGNTPDRFSGSKSGISASLAISGLQSEDEADYYCATWDDSLK
GWITGGGIKLIVL

>SEQ ID NO: 61 C2-VL
QVLTQPPSASGTPGQRVTISCSGSLSNIGRNPVNWYQQLPGTAPKLLIYL
DNLRLGGVPDRFSGSKSGTSASLAISGLQSEDEADYYCATWDDSLKGWLF
GGGTKLTNTL

>SEQ ID NO: 62 D3-VL
QSVLTQPPSASGTPGQRVTISCSGSLSNIGRNPVNWYQQLPGTAPKLLIY
LDNLRLSGATPDRFSGSKSGTSASLAISGLQSEDEADYYCATWDDSLIGW
LFGGGTKLTVL

>SEQ ID NO: 63 G10-VL
QSVLTQPPSASGTPGQRVTISCSGSLSNIGRNDVNWYQQLPGTAPKLLIY
LNNQRLGGVPDRFSGSKSGTSASLAISGLQSEDEADYYCATWDDSLKGWL
FGGGTKLTVL

>SEQ ID NO: 64 HPT-VL
QSVLTQPPSASGTPGQRVTISCSGSLSNIGRNPVNWYQQLPGTAPKLLIY
LNNQRPSGVPDRFSGSKSGTSASLAISGLQSEDEADYNCATWDDSHPGWT
FGGGTKLTVL

>SEQ ID NO: 65 GRVE-VL
QSVLTQPPSASGTPGQRVTISCSGSLSNIGRNPVNWYQQLPGTAPKLLIY
LNNQPSGVPDRFSGSKSGTSASLAISGLQSEDEADYYCATWDDSLNGWLF
GGGTKLTVL

>SEQ ID NO: 66 73combo1 (C1 + GRVE + HPT)-VL
QSVLTQPPSASGTPGQRVTISCSGSLSNIGRNEVNWYQQLPGTAPKLLIY
LNNQRPSGNTPDRFSGSKSGTSASLAISGLQSEDEADYYCATWDDSHPGW
TFGGGTKLTVL >SEQ ID NO: 67 73combo2 (C2 + GRVE + HPT)-VL
QSVLTQPPSASGTPGQRVTISCSGSLSNIGRNPVNWYQQLPGTAPKLLIY
LDNLRLGGVPDRFSGSKSGTSASLAISGLQSEDEADYYCATWDDSHIPGW
TFGGGTKLTVL >SEQ ID NO: 68 73combo3 (D3 + GRVE + HPT)-VL [10.3]
QSVLTQPPSASGTPGQRVTISCSGSLSNIGRNPVNWYQQLPGTAPKLLIY
LDNLRLSGVPDRFSGSKSGTSASLAISGLQSEDEADYNCATWDDSHPGWT
FGGGTKLTVL >SEQ ID NO: 69 73combo5 (G10 + GRVE + HPT)-VL
QSVLTQPPSASGTPGQRVTISCSGSLSNIGRNDVNWYQQLPGTAPKLLIY
LNNQRLGGVPDRFSGSKSGTSASLAISGLQSEDEADYYCATWDDSHPGWT
FGGGTKLTVL >SEQ ID NO: 70 73combo6 (GRVE + HPT)-VL
QSVLTQPPSASGTPGQRVTISCSGSLSNIGRNPVNWYQQLPGTAPKLLI
YLNNQRPSGVPDRFSGSKSGTSASLAISGLQSEDEADYYCATWDDSHPGW
TFGGGTKLTVL >SEQ ID NO: 71 CD730010-VH
EVQLLESGGGLVQPGGSLRLSCAASGFIFSSYAMSWVRQAPGKGLEWVSA
ISGSGGSTYYADSVKGRFTISRDNSKNTLYLQMNSLRAEDTAVYYCARLG
YSTIDYWGRGTLVTVSS

```
>SEQ ID NO: 72 CD730010GL9-VH
EVQLLESGGGLVQPGGSLRLSCAASGFTFSSYAMSWVRQAPGKGLEWVSA
ISGSGGSTYYADSVKGRFTISRDNSKNTLYLQMNSLRAEDTAVYYCARLG
YSTIDYWGRGTLVTVSS

>SEQ ID NO: 73 P32E-VH
EVQLLESGGGLVQPGGSRLRSCAASGFTFSSYAMSWVRQAPGKGLEWVSAI
SGSGGGSTYYADSVKGRFTISRDNSKNTLYLQMNSLRAEDTAVYYCARLGY
STIDYWGRGTLVTVSS

>SEQ ID NO: 74 C1-VH
EVQLLESGGGLVQPGGSLRLSCAASGFTFSSYAYSWVRQAPGKGLEWVSA
ISGSGGGSTYYADSVKGRFTISRDNSKNTLYLQMNSLRAEDTAVYYCARLG
YSTIDKNATGRGTLVTVSS

>SEQ. ID NO: 75 C2-VH
EVQLLESGGGLVQPGGSLRLSCAASGFTFSSYAYSWVRQAPGKGLEWVSL
IWGSWGSTYYADSVKGRFTISRDNSKNTLYLQMNSLRAEDTAVYYCARLG
YSTIDMWGRGTLVTVSS

>SEQ ID NO: 76 D3-VH
EVQLLESGGGLVQPGGSLRLSCAASGFTFSSYAYSWVRQAPGKGLEWVSA
ISGSGGRTYYADSVKGRFTISRDNSKNTLYLQMNSLRAEDTAVYYCARLG
YSTIDLWGRGTLVTVSS

>SEQ ID NO: 77 G10-VH
EVQLLESGGGLVQPGGSLRLSCAASGFTFSSYAYSWVRQAPGKGLEWVSA
ISGSWGRTYYADSVKGRFTISRDNSKNTLYLQMNSLRAEDTAVYYCARLG
YSTIDLWGRGTLVTVSS

>SEQ ID NO: 78 HPT-VH
EVQLLESGGGLVQPGGSLRLSCAASGFTFSSYAMSWVRQAPGKGLEWVSA
ISGSGGSTYYADSVKGRFTISRDNSKNTLYLQMNSLRAEDTAVYYCARLG
YSTIDYWGRGTLVTVSS

>SEQ ID NO: 79 GRVE-VH
EVQLLESGGGLVQPGGSLRLSCAASGFTFSSYAMSWVRQAPGKGLEWVSA
ISGSGGSTYYADSVKGRFTISRDNSKNTLYLQMNSLRAEDTAVYYCARLG
YGRVDEWGRGTLVTVSS

>SEQ ID NO: 80 73combo1 (C + GRVE + HPT)-VH
EVQLLESGGGLVQPGGSLRLSCAASGFTFSSYAYSWVRQAPGKGLEWVSA
ISGSGGSTYYADSVKGRFTISRDNSKNTLYLQMNSLRAEDTAVYYCARLG
YGRVDEWGRGTLVTVSS >SEQ ID NO: 81 73combo2 (C4 + GRVE + HPT)-VH
EVQLLESGGGLATQPGGSLRLSCAASGFTFSSYAYSWVRQAPGKGLEWVS
LIWGSWGSTYYADSVKGRFTISRDNSKNTLYLQMNSLRAEDTAVYYCARL
GYGRVDEWGRGTLVTVSS >SEQ ID NO: 82 73combo3 (D3 + GRVE + HPT)-VH
EVQLLESGGGLVQPGGSLRLSCAASGFTFSSYAYSWVRQAPGKGLEWVSAI
SGSGGRTYYADSVKGRFTISRDNSKNTLYLQMNSLRAEDTAVYYCARLGY
GRVDEWGRGTLVTVSS >SEQ ID No: 83 73combo5 (G10 + GRVE + HPT)-VH
EVQLLESGGGLVQPGGSLRLSCAASGFTFSSYAYSWVRQAPGKGLEWVSA
ISGSWGRTYYADSVKGRFTISRDNSKNTLYLQMNSLRAEDTAVYYCARLG
YGRVDEWGRGTLVTVSS >SEQ ID NO: 84 73combo6 (GRVE + HPT)-VH
EVQLLESGGGLVQPGGSLRLSCAASGFTFSSYAMSWVRQAPGKEILEWVS
AISGSGGSTYYADSVKGRFTISRDNSKNTLYLQMNSLRAEDTAVYYCARL
GYGRVDEWGRGTLVTVSS >SEQ ID NO: 85 CD730002VH
EVQLLESGGGLVQPGGSLRLSCAASGFTFSSYAMSWVRQAPGKGLEWVSA
ISGSGGSTYYADSVKGRFTISRDNSKNTLYLQMNSLRAEDTAVYYCARDK
GYYWYMDVWGQGTMVTVSS >SEQ ID NO: 86 CD730002VL
QSVLTQPPSVSVSPGQTATITCSGDKVGDKYASWYQQKPGQSPVLVIYED
TKRPSRIPERFSGSNSGNTATLTISGTQALDEADYFCQAWDTSFWVFGGG
TKLTVL >SEQ ID NO: 87 2C5VH
EVQLLESGGGLVQPGGSLRLSCAASGFTFSSYAMSWVRQAPGKGLEWVSA
ISGSGGSTYYADSVKRRFTISRDNSKNTLYLQMNSLRAEDTAVYYCARDK
GYYWYMDVWGQGTMVTVSS >SEQ ID NO: 88 2C5VL
QSVLTQPPSVSVSPGQTASLTCSGDKVGDKYASWYQQKPGQSPVLVIYED
TKRLSGIPERFSGSNSGNTATLTISGTQAMDEADYYCQAWDTSFWVFGGG
TKLTVL >SEQ ID NO: 89 CD730002 parent/2C5 FW4-VH
WGQGTMVTVSS >SEQ ID NO: 90 CD730002 parent FW1-VL
QSVLTQPPSVSVSPGQTATITC

>SEQ ID NO: 91 CD7300002 2C5 FW1-VL
QSVLTQPPSVSVSPGQTASITC

>SEQ ID NO: 92 CD730002 parent/2C5 FW2-VL
WYQQKPGQSPVLVIY

>SEQ ID NO: 93 CD730002 parent FW3-VL
RIPERFSGSNSGNTATLTISGTQALDEADYFC

>SEQ ID NO: 94 CD730002/2C5 FW3-VL
GIPERFSGSNSGNTATLTISGTQAMDEADYYC

>SEQ ID NO: 95 CD730002/2C5 CDR2-VH
AISGSGGSTYYADSVKR

>SEQ ID NO: 96 CD730002 parent/2C5 CDR3-VH
DKGYYWYNIDV

>SEQ ID NO: 97 CD730002 parent/2C5 CDR1-VL
SGDKVGDKYAS

>SEQ ID NO: 98 CD730002 parent CDR2-VL
EDTKRPS

>SEQ ID NO: 99 CD730002 2C5 CDR2-VL
EDTKRLS

>SEQ ID NO: 100 CD730002 parent/2C5 CDR3-VL
QAWDTSFWV

>SEQ ID NO: 101 Phen0203-VH
EVQLVESGGGVVQPGRSLRLSCAASGFRFSDFAMHWVRQAPGKGLEWVAG
ISYDGGNKYYADSVKGRFTISRDNSNNTLYLQMNSLRAEDTAVYYCAKDH
GYSGYYGHLDYWGRGTLVTVSS >SEQ ID NO: 102 Phen0203-VL
QSVVTQPPSASGTPGQRVTISCSGSSSNIGSNTVNWYQQLPGTAPKLLIY
SNNQRPSGVPDRFSGSKSGTSASLAISGLQSEDEADYYCAAWDDSLNGRV
FGTGTKLTVL >SEQ ID NO: 103 CD730004-VH
EVQLLESGGGLVQPGGSLRLSCAASGFTFSSYAMSWVRQAPGKGLEWVSA
ISGSGGSTYYADSVKGRFTISRDNSKNTLYLQMNSLRAEDTAVYYCAKDR
PNYYGASGSYYKQGGDHWGQGTMVTVSS >SEQ ID NO: 104 CD730004-VL
NFMLTQPHSVSESPGQTVTISCTRSSGSIASKYVQWYQKRPGSSPTTVIY
EDTQRPSGVPDRFSGSIDISSNSASLTISGLRTEDEADYYCQSYDSTNWV
FGGGTKVTVL >SEQ ID NO: 105 CD730008-VH
EVQLLETGGGLVQPGGSLRLSCAASGFTFSSYAMSWVRQAPGKGLEWVSA
ISGSGGSTYYADSVKGRFTISRDNSKNTLYLQMNSLRAEDTAVYYCARGN
YGNLDHWGKGTLVTVSS >SEQ ID NO: 106 CD730008-VL
QSVLTQPPSVSVSPGQTASITCSGDKVGDKYASWYQQKPGQSPVLVIYQD
RKRPSGIPERFSGSNSGNTATLTISGTQPMDEADYYCQAWDSSHWVFGGG
TKLTVL
```

SEQUENCE LISTING

```
>SEQ ID NO: 107 CD730068-VH
EVQLLESGGGLVQPGGSLRLSCAASGFTFSNYIMGWVRQAPGKGLEWVSS
ISSSGGATIYADSVKGRFTISRDNSKNTLYLQMNSLRAEDMAVYYCAKDH
LGGHGMDVWGQGTTVTSS

>SEQ ID NO: 108 CD730068-VE
DIQMTQSPSSLSASVGDRVTITCRASQDISNYLAWFQQKPGKAPKSLIFA
ASSLESGVPSKFSGSGSGTDFTLTISSLQPEDSATYYCQQYNSYPLTFGG
GTKVEIK

>SEQ ID NO: 109 CD730069-VH
EVQLLESGGGLVQPGGSLRLSCAASGFTFSEYQMGWVRQAPGKGLEWVSY
IRSSGGQIYADSVKGRFTISRDNSKNTLYLQMNSLRAEDTAVYYCARRTY
SSGWHIDYWGQGTLVTSS

>SEQ ID NO: 110 CD730069-VL
DIQMTQSPDSLSASVGDRVTITCRASQSISRYLNWYQQKPGKAPKLLIYG
ASSLQSGVPSRFSGSGSGTDFSLTISSLQLEDFATYYCQQSYRTPLTFGG
GTKVEIQ

>SEQ ID NO: 111 Clone 2 SGMY-VH
EVQLLESGGGLVQPGGSLRLSCAASGFTFSSYAMSWVRQAPGKGLEWVSA
ISGSGGSTYYADSVKGRFTISRDNSKNTLYLQMNSLRAEDTAVYYCARDK
GYYWYMDVWGQGTMVTVSS >SEQ ID NO: 112 Clone 2 SGMY-VL
QSVLTQPPSVSVSPGQTASITCSGDKVGDKYASWYQQKPGQSPVLVIYED
TKRPSGIPERFSGSNSGNTATLTISGTQAMDEADYYCQAWDTSFWVFGGG
TKLTVL >SEQ ID NO: 113 CDRH1 Y32V-VH
EVQLLESGGGLVQPGGSLRLSCAASGFTFSSVAMSWVRQAPGKGLEWVSA
ISGSGGSTYYADSVKGRFTISRDNSKNTLYLQMNSLRAEDTAVYYCARDK
GYYWYMDVWGQGTMVTVSS >SEQ ID NO: 114 CDRH1 M34R-VH
EVQLLESGGGLVQPGGSLRLSCAASGFTFSSYARSWVRQAPGKGLEWVSA
ISGSGGSTYYADSVKGRFTISRDNSKNTLYLQMNSLRAEDTAVYYCARDK
GYYWYMDVWGQGTMVTVSS >SEQ ID NO: 115 CDRH2 T57P-VH
EVQLLESGGGLVQPGGSLRLSCAASGFTFSSYAMSWVRQAPGKGLEWVSA
ISGSGGSPYYADSVKGRFTISRDNSKNTLYLQMNSLRAEDTAVYYCARDK
GYYWYMDVWGQGTMVTVSS >SEQ ID NO: 116 CDRH2 A60G-VH
EVQLLESGGGLVQPGGSLRLSCAASGFTFSSYAMSWVRQAPGKGLEWVSA
ISGSGGSTYYGDSVKGRFTISRDNSKNTLYLQMNSLRAEDTAVYYCARDK
GYYWYMDVWGQGTMVTVSS >SEQ ID NO: 117 CDRH2 G65R-VH
EVQLLESGGGLVQPGGSLRLSCAASGFTFSSYAMSWVRQAPGKGLEWVSA
ISGSGGSTYYADSVKRRFTISRDNSKNTLYLQMNSLRAEDTAVYYCARDK
GYYWYMDVWGQGTMVTVSS >SEQ ID NO: 118 CDRL2 T52S-VL
QSVLTQPPSVSVSPGQTASITCSGDKVGDKYASWYQQKPGQSPVLVIYED
SKRPSGIPERFSGSNSGNTATLTISGTQAMDEADYNCQAWDTSFWVFGGG
TKLTVLL >SEQ ID NO: 119 CDRL2 R54Y-VL
QSVLTQPPSVSVSPGQTASPTCSGDKVGDKYASWYQQKPGQSPVLVIYED
TKYPSGIPERFSGSNSGNTATLTISGTQAMDEADYYCQAWDTSFWVFGGG
TKLTVLVL >SEQ ID NO: 120 CDRL2 P55H-VL
QSVLTQPPSVSVSPGQTASITCSGDKVGDKYASWYQQKPGQSVLVIYEDT
KRHSGIPERFSGSNSGNTATLTISGTQAMDEADYYCQAWDTSFWVFGGGT
KLTVLVL >SEQ ID NO: 121 CDRL2 P55L-NTL
QSVLTQPPSVSVSPGQTASITCSGDKVGDKYASWYQQKPGQSPVLVIYED
TKRLSGIPERFSGSNRGNTATLTISGTQAMDEADYYCQAWDTSFWVFGGG
TKLTVLVL

>SEQ ID NO: 122 2SGMY FW3-VL
GIPERFSGSNRGNTATLTISGTQAIVEDEADYYC

>SEQ ID NO: 123 CDRH1 Y32V CDR1-VH
SVAMS

>SEQ ID NO: 124 CDRH1 M34R CDR1-VH
SYARS

>SEQ ID NO: 125 CDRH2 T57P CDR2-VH
ALSGSGGSPYYADSVKG

>SEQ ID NO: 126 CDRH2 A60G CDR2-VH
AISGSGGSTYYGDSVKG

>SEQ ID NO: 127 CDRL2 T52S CDR2-VL
EDSKRPS

>SEQ ID NO: 128 CDRL2 R54H CDR2-VL
EIYIKYPS

>SEQ ID NO: 129 CDRL2 P55H CDR2-VL
EDTKRLS
```

What is claimed is:

1. A method of inhibiting tumor growth in a subject comprising administering an anti-CD73 antibody, wherein the anti-CD73 antibody is MEDI9447 or an antigen-binding fragment thereof, and an adenosine receptor inhibitor (A2Ari) for inhibiting tumor growth to the subject.

2. A method of increasing an anti-tumor immune response comprising administering an anti-CD73 antibody, wherein the anti-CD73 antibody is MEDI9447 or an antigen-binding fragment thereof, and an adenosine receptor inhibitor (A2Ari) to a subject in need thereof.

3. A method of treating a tumor in a subject comprising administering to the subject an anti-CD73 antibody, wherein the anti-CD73 antibody is MEDI9447 or an antigen-binding fragment thereof, and an adenosine receptor inhibitor (A2Ari).

4. The method of claim 3, wherein the A2A receptor inhibitor is SCH58261.

5. The method of claim 3, wherein the anti-CD73 antibody or antigen-binding fragment thereof and the A2Ari are administered concurrently.

6. The method of claim 3, wherein the anti-CD73 antibody or antigen-binding fragment thereof is administered prior to the A2Ari.

7. The method of claim 3, wherein the A2Ari is administered prior to the anti-CD73 antibody or antigen-binding fragment thereof.

8. The method of claim 3, wherein the tumor is a lung cancer.

9. The method of claim 3, wherein said method results in an increase in overall survival as compared to the administration of any one of the anti-CD73 antibody or the A2Ari alone.

10. The method of claim 3, wherein the said method induces or increases a tumor-specific immune response.

11. The method of claim 3, wherein the said method reduces the immunosuppressive effects of a AMP/CD73/adenosine pathway.

12. The method of claim 3, wherein the said method reduces metastasis or reduces the propensity of the tumor to metastasize relative to the administration of either the anti-CD73 antibody or the A2Ari alone.

13. The method of claim 3, wherein the said method reduces the number of metastases within the subject.

14. The method of claim 3, wherein the subject is a human patient.

15. The method of claim 3, wherein the tumor is a CD73 overexpressing tumor.

* * * * *